United States Patent [19]
Greenlee et al.

[11] Patent Number: 5,395,931
[45] Date of Patent: Mar. 7, 1995

[54] 6-AMIDO-1-METHYL-2-(SUBSTITUTED-THIO)CARBAPENEMS

[75] Inventors: Mark L. Greenlee, Rahway; Frank P. DiNinno, Old Bridge; Thomas N. Salzmann, No. Plainfield, all of N.J.

[73] Assignee: Merck & Co., Inc., Rahway, N.J.

[21] Appl. No.: 887,417

[22] Filed: May 20, 1992

Related U.S. Application Data

[63] Continuation of Ser. No. 768,471, Sep. 30, 1991, abandoned, which is a continuation of Ser. No. 371,490, Jun. 26, 1989, abandoned, which is a continuation-in-part of Ser. No. 213,579, Jun. 30, 1988, abandoned.

[51] Int. Cl.⁶ ............... C07D 498/04; C07D 205/085
[52] U.S. Cl. ................................ 540/300; 540/364
[58] Field of Search ...................... 540/300, 304

[56] References Cited

U.S. PATENT DOCUMENTS

| | | | |
|---|---|---|---|
| 4,206,219 | 6/1980 | Christensen et al. | 540/364 |
| 4,217,453 | 8/1988 | Christensen et al. | 540/364 |
| 4,218,459 | 8/1988 | Cama et al. | 540/364 |
| 4,218,463 | 8/1988 | Christensen et al. | 540/364 |
| 4,260,627 | 4/1981 | Christensen et al. | 540/364 |
| 4,277,482 | 7/1981 | Christensen et al. | 540/364 |
| 4,298,741 | 11/1981 | Christensen et al. | 540/364 |
| 4,347,355 | 8/1982 | Chu | 540/364 |
| 4,348,264 | 9/1982 | Rosati | 540/364 |
| 4,407,815 | 10/1983 | Pearson et al. | 540/364 |
| 4,771,135 | 9/1988 | Blaszczak | 540/360 |
| 4,841,042 | 6/1989 | Häbich | 540/200 |

FOREIGN PATENT DOCUMENTS

| | | |
|---|---|---|
| 0045198 | 2/1982 | European Pat. Off. |
| 0073100 | 3/1983 | European Pat. Off. |
| 116854A | 8/1984 | European Pat. Off. |
| 237027A | 9/1987 | European Pat. Off. |
| 3509769A | 9/1986 | Germany |
| 58-174382A | 10/1983 | Japan |
| 63-048274A | 2/1988 | Japan |

OTHER PUBLICATIONS

Shih, D. H., et al., Heterocycles, vol.21, No.1, 1984 pp. 29–40.
Hakimelakhi, G. H., et al., Helvetica Chem. Acta, vol.65,1982, pp. 1374–1377.
Herdewin, P. et al., Can. J. Chem., vol.60, 1982, pp. 2903–2907.
Sharma, R., et al., J. Chem. Soc. Perkin Trans.1, 1987, pp. 2361–2369.
Bateson, J. H., et al., J.C.S. Chem. Comm., 1980, pp. 1084–1085.
Bateson, J. H., et al., J.C.S. Chem. Comm., 1980, pp. 185–186.
Koller, W., et al., Tetrahedron Ltt. Vo.23, No. 15, 1982, pp. 1545–1548.
Yamamoto, K., et al,. Tetrahedron Ltt. vol.23, No.50,1982, pp.5339–5343.
Branch, C. L., et al., J. Chem Soc. Perkin Trans.1, 1982 pp. 2123–2129.
Hakimelahi, G. H., Helvetica Chimica Agta, Vo.65,1982, pp. 1378–1384.
Rosati, R. L. et al., J. Am. Chem. Soc., vol.104, No.15, 1982 pp. 4262–4264.
Kametani, T., et al. Chem. Pharm. Bull, vol.31, 1983, pp. 2578–2583.
Narisada, S., et al., MEDI, Tues. Afternoon–Gen.–Antibiotics, No.13.
Herdewijn, P., et al., Nouveau J. De Chimie, vol.7-,No.12,1983,pp. 691–695.

Primary Examiner—Robert Gerstl
Attorney, Agent, or Firm—Richard C. Billups; Mark R. Daniel; Joseph F. DiPrima

[57] ABSTRACT

New antibacterial 6-amido-1-methyl-2-(substituted-thio)-carbapenems and process for their synthesis involving new azetidinone intermediates.

3 Claims, No Drawings

6-AMIDO-1-METHYL-2-(SUBSTITUTED-THIO)-CARBAPENEMS

This is a continuation of application Ser. No. 07/768,471, filed Sept. 30, 1991, which is continuation of application Ser. No. 371,490, filed Jun. 26, 1989, which is continuation-in-part of the application Ser. No. 213,579, filed on Jun. 30, 1988, all now abandoned.

BACKGROUND OF THE INVENTION

1) Field of the Invention

This invention relates to new antibacterial 6-amido-1-methyl-2-(substituted-thio)-carbapenems and a process for their synthesis involving new azetidinone intermediates.

2) Brief Description of Disclosures in the Art

Carbapenem antibiotics, particularly imipenem (see U.S. Pat. Nos. 3,950,377 and 4,194,047) is well known for treating a broad spectrum of gram-negative and gram-positive bacterial infections.

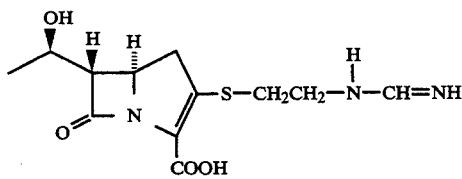

Imipenem

1-β-Methylcarbapenems, as described in the reference *Heterocycles*, 1984, Vol. 21, pp. 29-40 by D. H. Shih, F. Baker, L. Cama and B. G. Christensen, are extremely useful and effective broad spectrum antibiotics, useful against a wide variety of bacteria including gram-positive bacteria such as *S. aureus*, Strep. sp., *B. subtilis*, and gram-negative bacteria such as *E. coli*, Shigella sp., Enterobacter sp., Klebsiella sp., Proteus, Serratia and Pseudomonas sp.

However, all of the above antibacterial carbapenems utilize 6-substituents other than amido or substituted amido which are the 6-substituents of choice in penicillin, e.g.

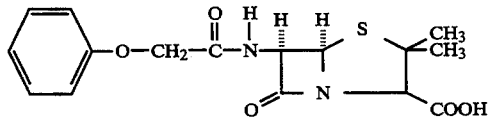

Penicillin V or the cephalosporins, e.g.

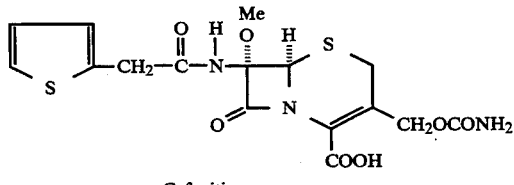

Cefoxitin

6-Amidocarbapenems and penams are known in the art as exemplified in the following references: U.S. Pat. No. 4,260,627; U.S. Pat. No. 4,206,219; U.S. Pat. No. 4,217,453; U.S. Pat. No. 4,218,459; U.S. Pat. No. 4,218,463; U.S. Pat. No. 4,277,482; and U.S. Pat. No. 4,298,741 to Merck & Co., Inc. which describe 1-H-6-amidocarbapenems and 1-methyl-6-aminocarbapenems; BE 887,618 and U.S. Pat. No. 4,347,355 to Abbott which describe 1,1-diloweralkyl-6-amidocarbapenems; EPO Publication No. 040,494 and U.S. Pat. No. 4,348,264 to Pfizer which describes 1-hydroxy, acetoxy or 1,1-oxocarbapenems with 6-position conventional penicillin sidechains; EPO Publication Nos. 634,443 and 073,100 and U.S. Pat. No. 4,407,815 to Beecham which describe 1-H-6-amidocarbapenems and penams; Japanese Kokai 58 174 382 to Sanraku-Ocean Co. Ltd. which discloses 6-phthalimido-2-SR carbapenems; EPO Publication No. 045,198 to Takeda Chem. Ind. Ltd which discloses 1-alkyl-1-alkoxycarbonyl, cyano or COR-substituted-6-amidocarbapenems; and EPO Publication No. 116,854 to Hoffmann-LaRoche AG which discloses new azetidinone derivatives which can be used to prepare 1-H carbapenems; Sanraku EP 0,237,027 and Japanese Patent J6 3048-274A; and Bayer AG DE 3,509,769.

Literature articles relating to 1-H-6-amidocarbapenems discussing problems in ring closures and ester deblocking reactions include: *Tetrahedron Letters*, 1982, 23 (15), 1545-1548; *Tetrahedron Letters*, 1982, 23 (50), 5339-5342; L. C. Blaszczak, Eli Lilly Co. Report "Joint Great Lakes and Central Regional Meeting", Western Michigan University, May 23-24, 1984; *J. Chem. Soc., Perkins Trans. I*, 1982, 2123-2129; *Helv. Chim. Acta*, 1982, 65, 1378-1384; *J.A.C.S.*, 1982, 104, 4262-4264; *Chem. Pharm. Bull.* 31 2578 (1983); N. Narisada et. al. 176th ACS National Meeting, Miami, Fla. 1978.; and *Nouv. J. Chim.* 7 691 (1983).

New antibacterial compounds are constantly being searched for to enhance the potency and decrease the side effects of current existing carbapenem antibiotics. Thus far, 1-methyl-6-amidocarbapenems have not been disclosed in the art.

SUMMARY OF THE INVENTION

It has been found that a new class of compounds, 6-amido-1-methyl-2-(substituted-thio)-carbapenems exhibit antibacterial activity and can be synthesized from new 3-phthalimido- and 3-azido-azetidinone intermediates.

By this invention there is provided a compound of the structural formula:

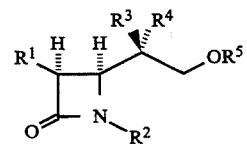

wherein $R^1$ is selected from:

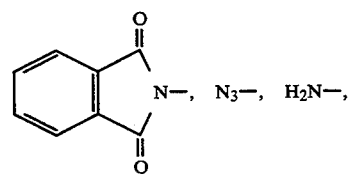

-continued

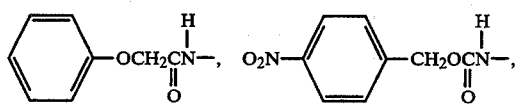

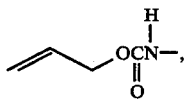

$R^2$ is hydrogen or a conventional nitrogen protecting group, removable by acid or basic hydrolysis, catalytic hydrogenation or oxidative cleavage; $R^5$ is hydrogen or a conventional hydroxyl protecting group, removable by acid or basic hydrolysis, catalytic hydrogenation or oxidative cleavage; $R^3/R^4$ is $CH_3/H$ or $H/CH_3$; and wherein $R^2$ and $R^5$ taken together can comprise a six-membered nitrogen, oxygen-containing heterocyclic ring.

Also provided is a compound of the structure:

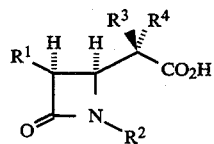

wherein $R^1$ is selected from:

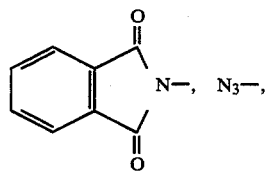

$R^2$ is hydrogen or a nitrogen protecting group; and $R^3/R^4$ is $CH_3/H$ or $H/CH_3$.

Further provided is a compound of the formula:

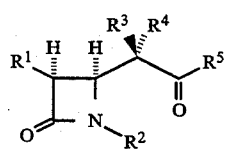

wherein $R^1$ is selected from:

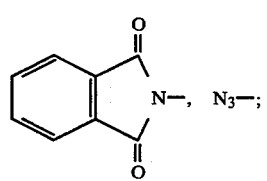

$R^2$ is hydrogen or a removable nitrogen protecting group; $R^5$ is

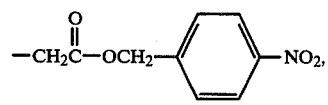

and wherein $R^3/R^4$ is $CH_3/H$ or $H/CH_3$.

Furthermore, there is provided a compound of the structure:

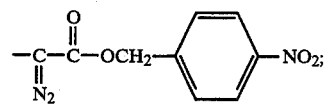

wherein $R^1$ is selected from:

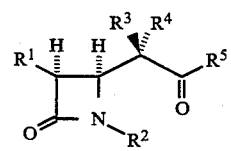

$R^2$ is hydrogen, a nitrogen protecting group, or one of the following groups:

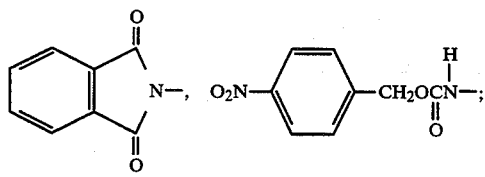

$R^5$ is selected from:

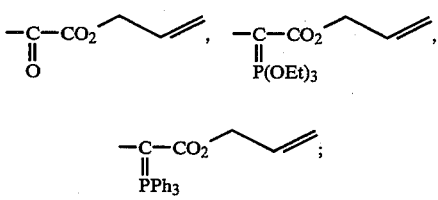

and $R^3/R^4$ is $CH_3/H$ or $H/CH_3$.

In addition, there is provided a compound of the structure:

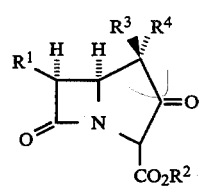

wherein $R^1$ is selected from the following groups:

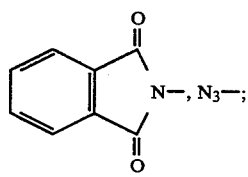

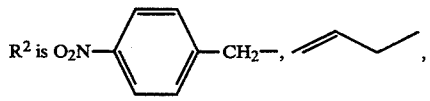

unsubstituted or substituted $C_1$–$C_4$ alkyl, the substituents being conventional in the carbapenem art; wherein $R^3/R^4$ is $CH_3$/H or H/$CH_3$.

There is further provided a compound of the structure:

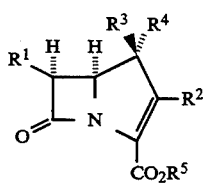

wherein $R^1$ is

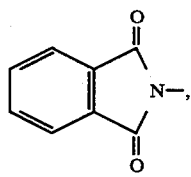

$R^2$ is selected from:

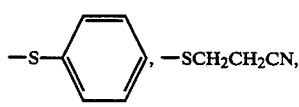

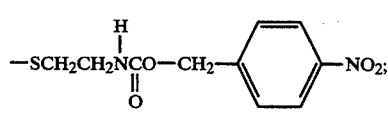

$R^5$ is selected from radicals conventional in the carbapenem art including:

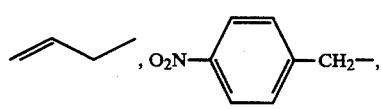

$C_1$–$C_4$ alkyl, substituted $C_1$–$C_4$ alkyl, pharmaceutically acceptable salt, conventional biolabile ester or blocking ester groups; wherein $R^3/R^4$ is $CH_3$/H or H/$CH_3$.

Also by this invention there is provided a compound of the formula:

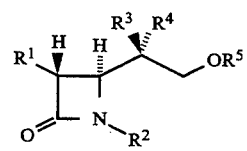

wherein $R^1$ is selected from:

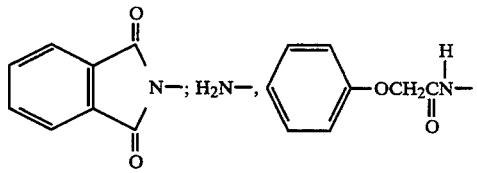

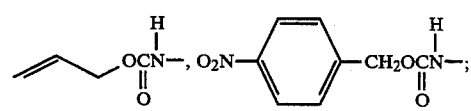

$R^2$ is hydrogen or a conventional nitrogen protecting group; $R^5$ is hydrogen or a conventional hydroxyl protecting group; wherein $R^3/R^4$ is $CH_3$/H or H/CH3; and wherein $R^2$ and $R^5$ taken together can comprise a six-membered nitrogen, oxygen-containing heterocyclic ring.

Also provided is a compound of the formula;

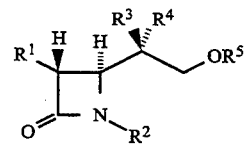

wherein $R^1$ is selected from the following:

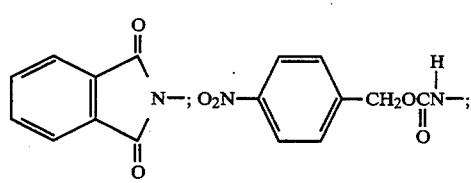

$R^2$ is selected from

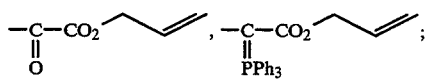

$R^5$ is hydrogen or a hydroxy protecting group; and wherein $R^3/R^4$ is $CH_3$/H or H/$CH_3$.

Further provided is a compound of the formula:

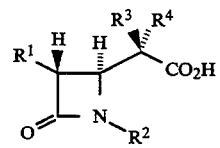

wherein $R^1$ is selected from:

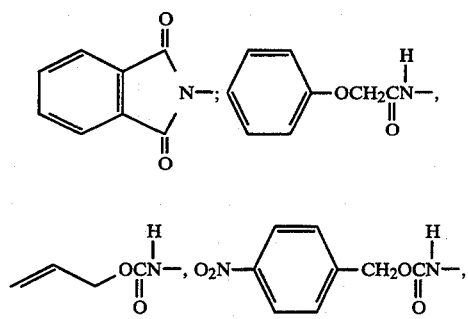

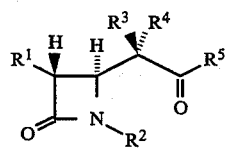

$H_2N-$; and $R^2$ is hydrogen or a removable nitrogen protecting group; and wherein $R^3/R^4$ is $CH_3/H$ or $H/CH_3$.

Furthermore, there is provided a compound of the structure:

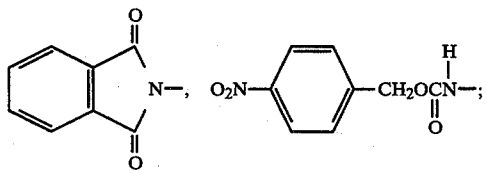

wherein $R^1$ is selected from

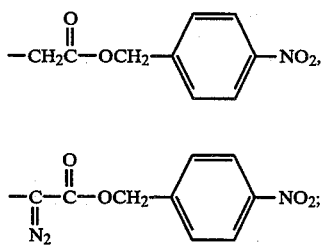

$R^2$ is hydrogen or a nitrogen protecting group; $R^5$ is

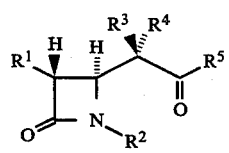

and wherein $R^3/R^4$ is $CH_3/H$ or $H/CH_3$.

In addition, there is provided a compound of the structure:

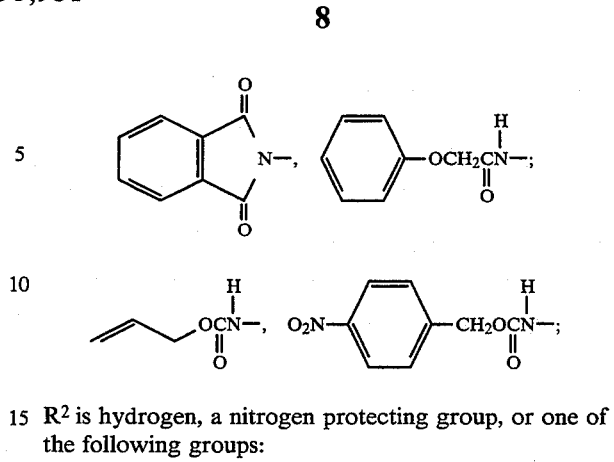

wherein $R^1$ is selected from:

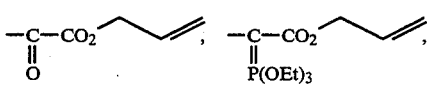

$R^2$ is hydrogen, a nitrogen protecting group, or one of the following groups:

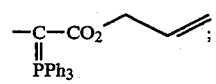

$R^5$ is selected from:

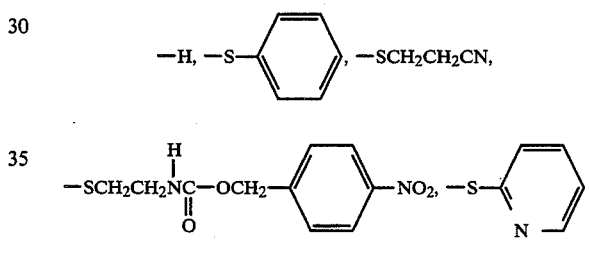

and wherein $R^3/R^4$ is $CH_3/H$ or $H/CH_3$.

Also provided are compounds of the formulae:

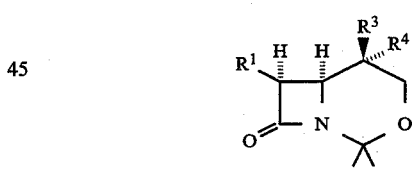

and

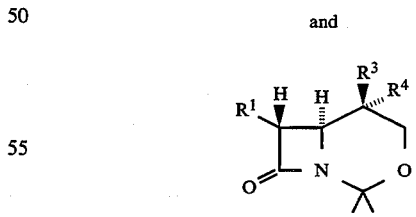

wherein $R^1$ is $H_2N-$,

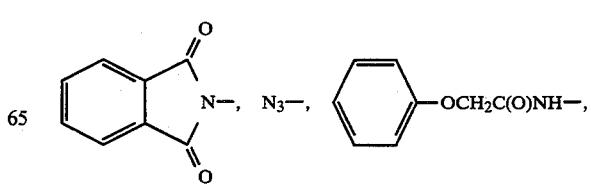

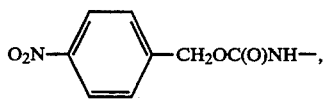

or

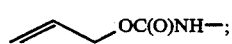

and $R^3/R^4$ is $CH_3/H$ or $H/CH_3$.

There is further provided a compound of the structure:

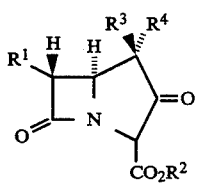

wherein $R^1$ is selected from:

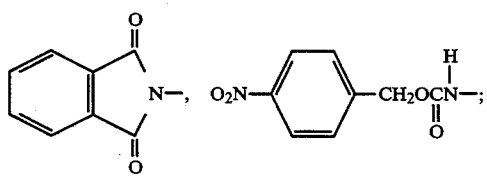

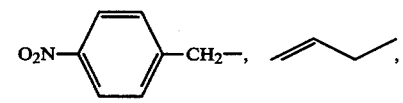

$C_1-C_4$ alkyl, substituted $C_1-C_4$ alkyl; and wherein $R^3/R^4$ is $CH_3/H$ or $H/CH_3$.

There is furthermore provided a compound of the structure:

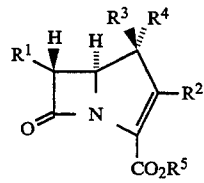

wherein $R^1$ is selected from:

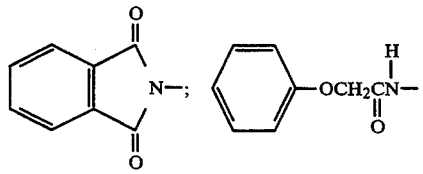

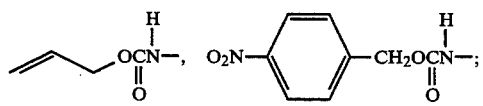

$R^2$ is selected from:

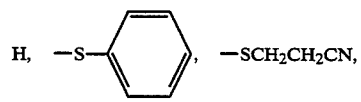

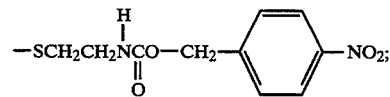

$R^5$ is selected from

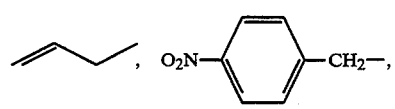

$C_1-C_4$ alkyl, substituted $C_1-C_4$ alkyl, pharmaceutically acceptable salt, biolabile ester or blocking ester groups; and wherein $R^3/R^4$ is $CH_3/H$ or $H/CH_3$.

BRIEF DESCRIPTION OF THE INVENTION AND PREFERRED EMBODIMENTS

The invention can be readily understood by reference to the following flow sheets which exhibit the processes for the synthesis of the instantly claimed compounds.

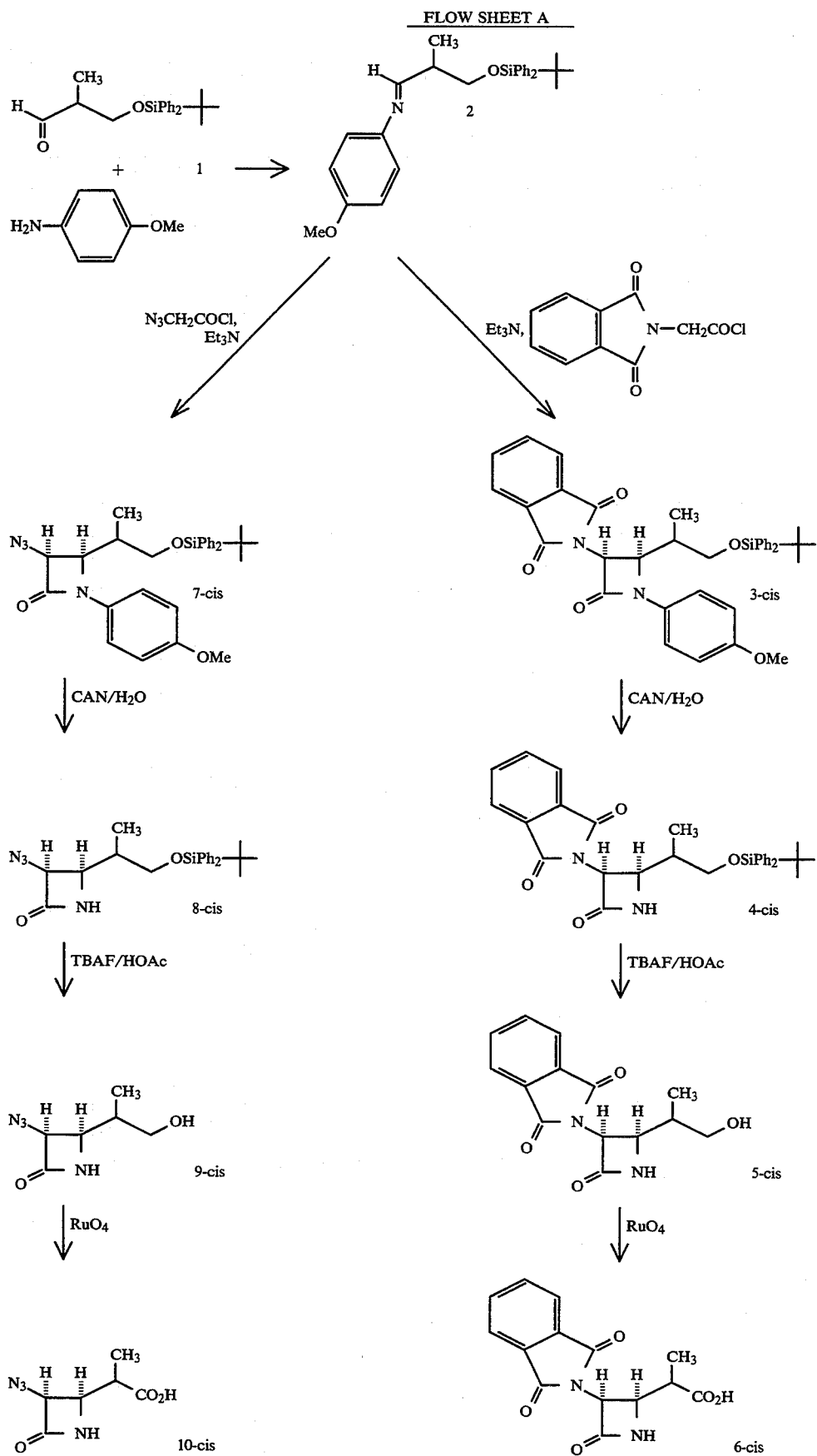

FLOW SHEET B
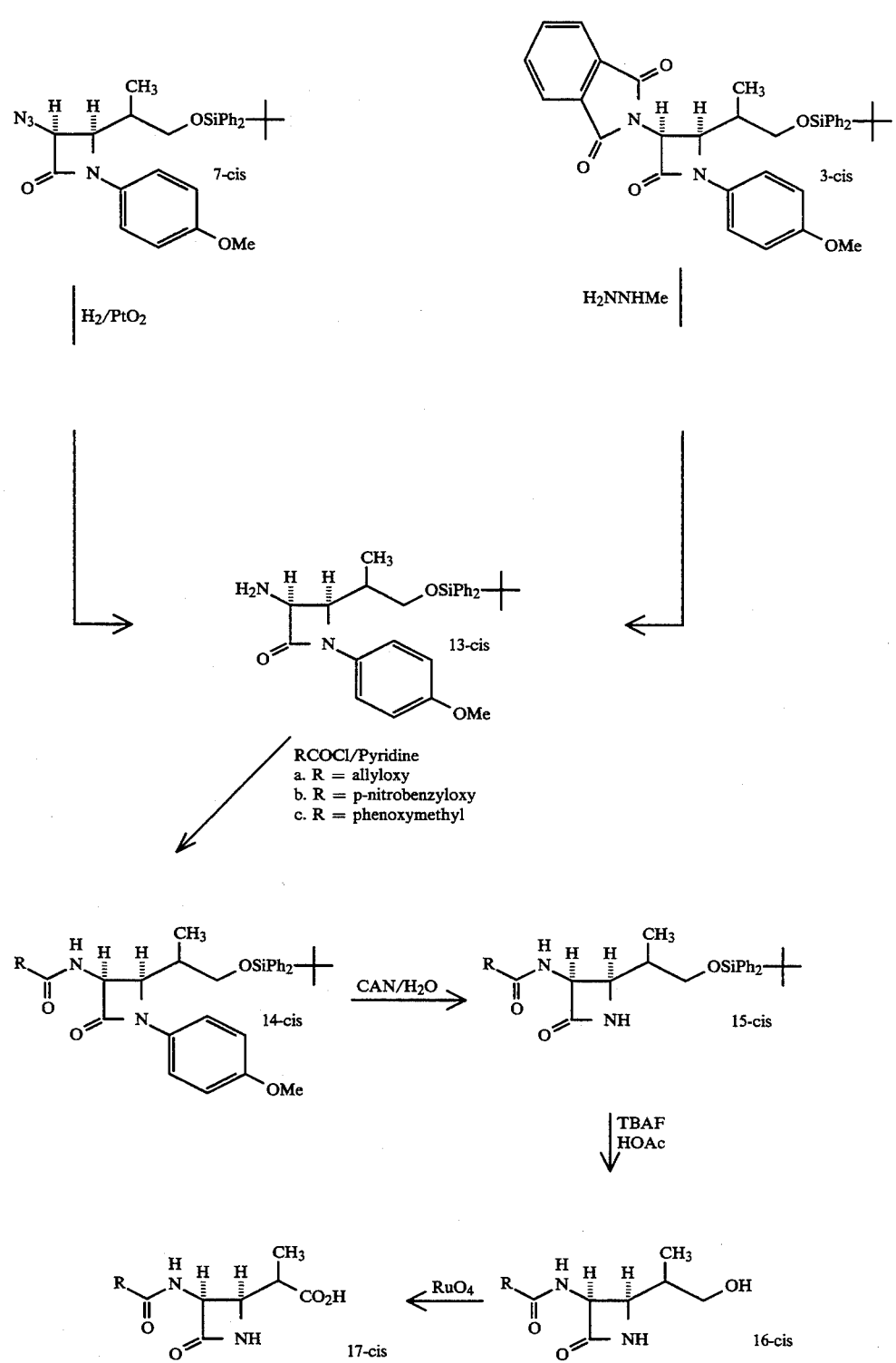

FLOW SHEET C
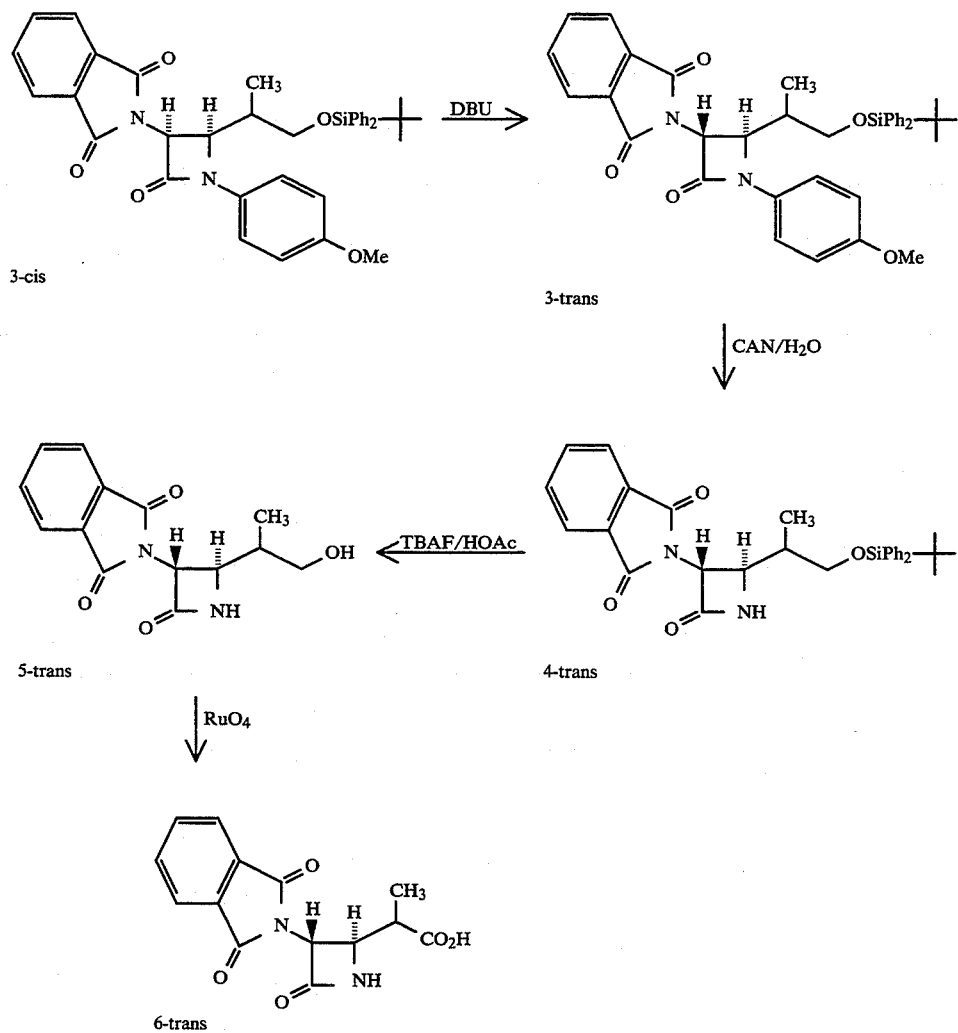
FLOW SHEET D
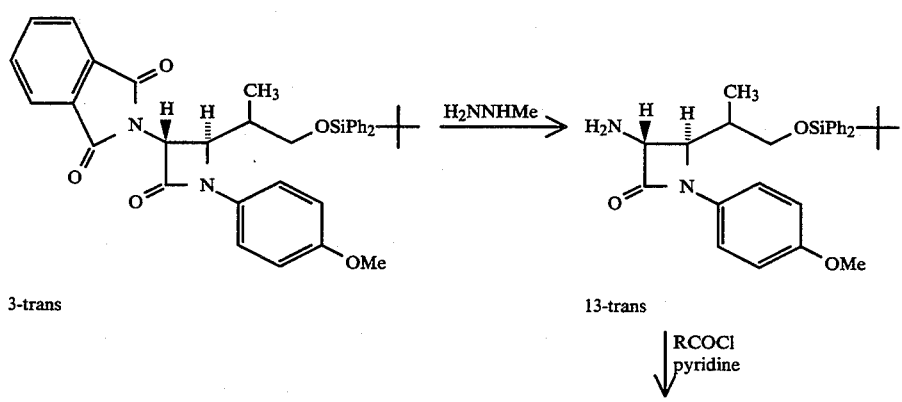

FLOW SHEET D
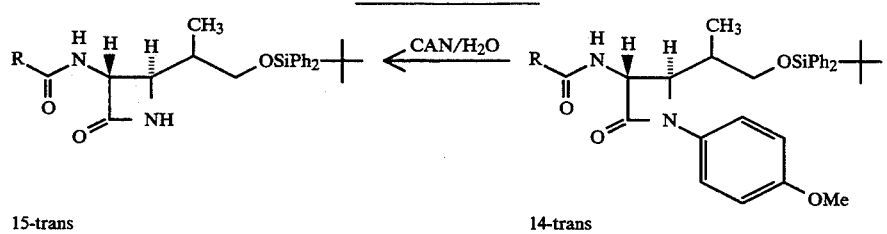
15-trans 14-trans
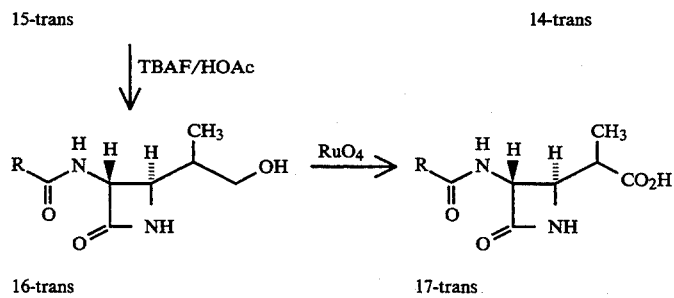
16-trans 17-trans
a. R = Allyloxy
b. R = p-nitrobenzyloxy
c. R = phenoxymethyl
FLOW SHEET E
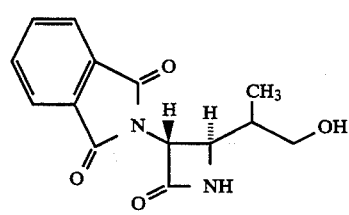
5-trans
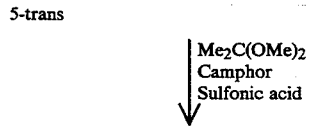
11-trans
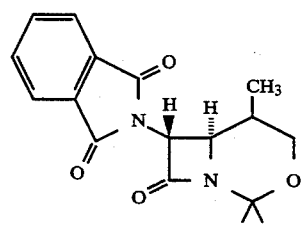
12-trans
-continued
FLOW SHEET E
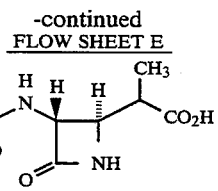
17-trans
a. R = Allyloxy
b. R = p-nitrobenzyloxy
c. R = phenoxymethyl
FLOW SHEET F
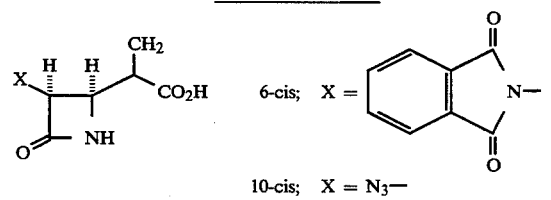
6-cis; X = 
10-cis; X = $N_3-$
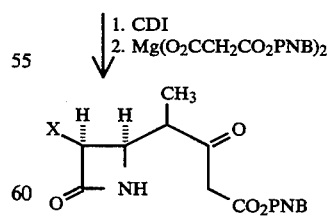
18-cis
a. X =
b. X = $N_3-$

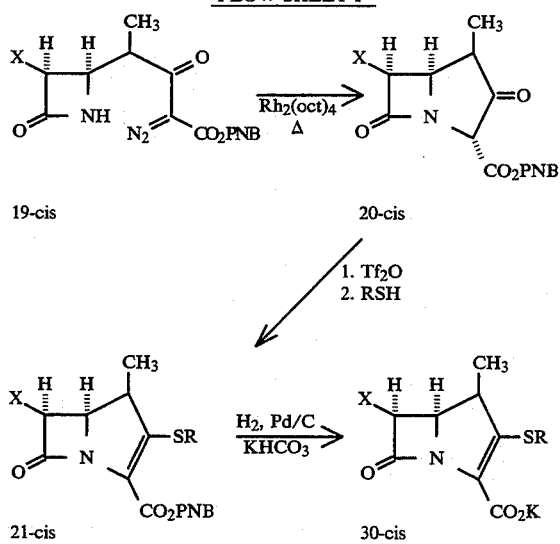
FLOW SHEET G
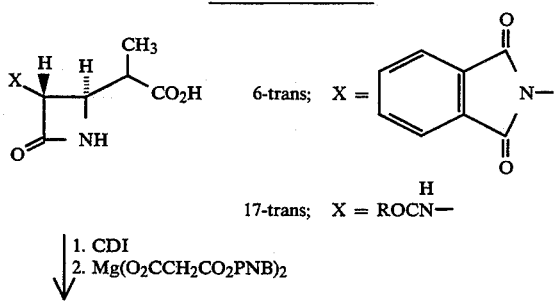
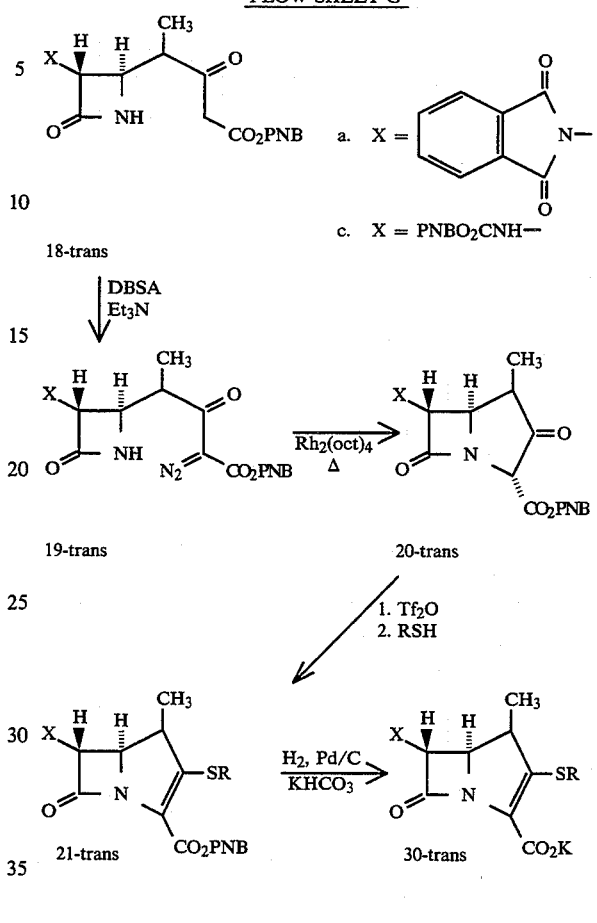

5,395,931
-continued
FLOW SHEET H
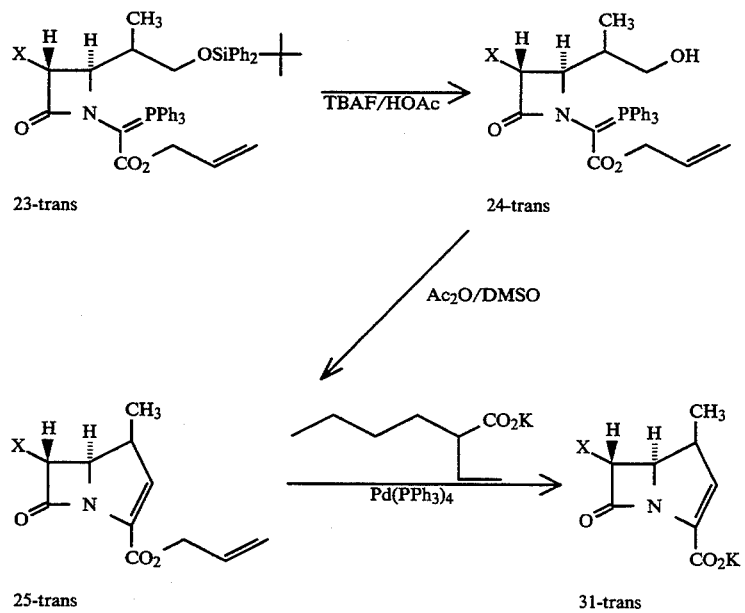
FLOW SHEET I
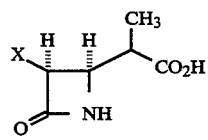
SR¹ = SPh
SR² = SCH$_2$CH$_2$CN
SR³ = SCH$_2$CH$_2$NHCO$_2$PNB
6-cis
17-cis
↓ HSR/DCC
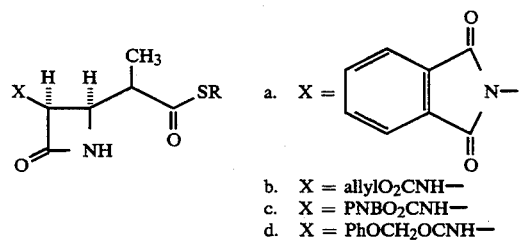
a. X = (phthalimido)
b. X = allylO$_2$CNH—
c. X = PNBO$_2$CNH—
d. X = PhOCH$_2$OCNH—
26-cis
↓ ClCOCO$_2$allyl
Pyridine
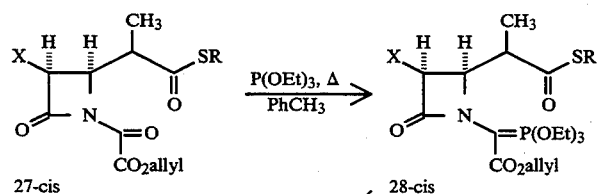
27-cis    28-cis
↓ p-xylene/138°

FLOW SHEET I

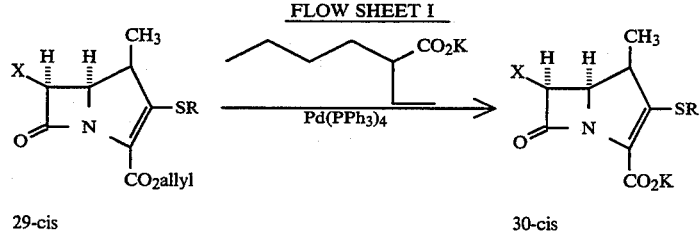

29-cis → 30-cis

FLOW SHEET J

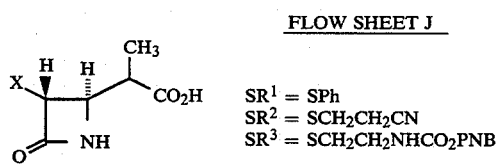

6-trans
17-trans

↓ HSR/DCC

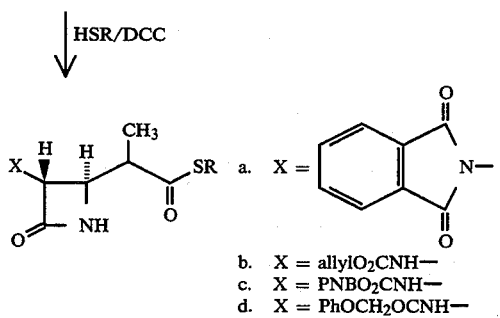

a. X = phthalimido
b. X = allylO₂CNH—
c. X = PNBO₂CNH—
d. X = PhOCH₂OCNH—

26-trans

↓ ClCOCO₂allyl / Pyridine

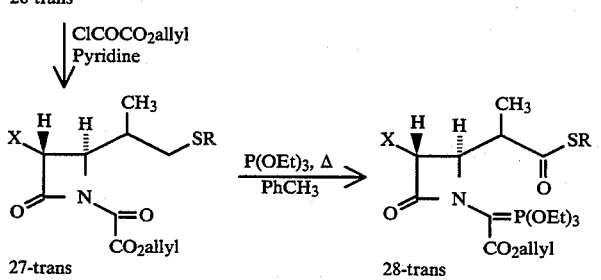

27-trans → 28-trans

↓ p-xylene/138°

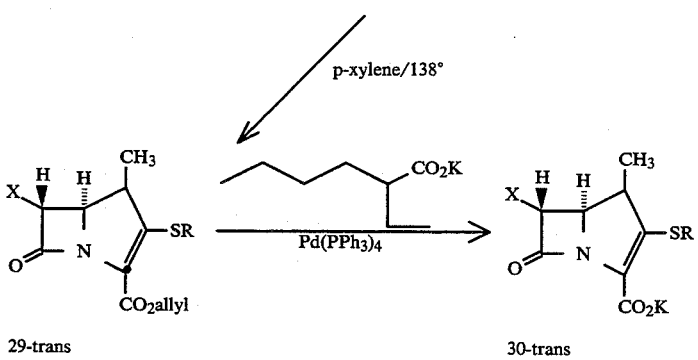

29-trans → 30-trans

The nomenclature used herein is as follows. The Arabic number refers to a specific compound as designated in the Flow Sheet. A letter following the number refers to a specific nitrogen substituent on the 3-position of the azetidinone zing, as designated in the Flow Sheet. The cis or trans designation refers to the 3H, 4H configuration on the azetidinone ring. Finally, the alpha- or beta-methyl designation refers to the orientation of the methyl substituent on the alkyl side-chain at the 4-position of the azetidinone ring, or the 1-methyl substituent on the carbapenem or carbapenem ring system. Thus, in Flow Sheet B, 14a-cis-βMe is the structure:

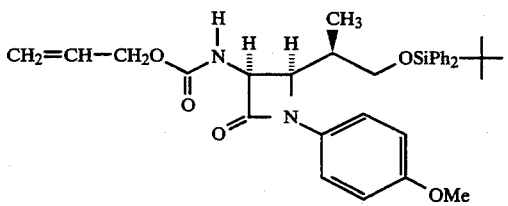

and in Flow Sheet D, 14a-trans-αMe is the structure:

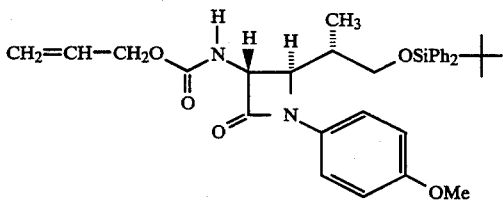

The compounds of this invention are generally provided as racemic mixtures. The optical isomer depicted in the flow sheets is that which is believed to lead to the greatest antibacterial activity.

Flow Sheets A-E illustrate the synthesis of the azetidinone intermediates used in the ring closure processes of Flow Sheets F,G,H,I and J to synthesize the antibacterial carbapenems of the invention.

Flow Sheet A illustrates the synthesis of the azido- and phthalimido-substituted cis-azetidinones 10-cis and 6-cis respectively and Flow Sheet B describes the amido-substituted cis-azetidinones 17-cis. Flow Sheets C,D, and E illustrate the synthesis of the corresponding trans-azetidinone intermediates.

Referring to Flow Sheet A, the starting aldehyde intermediate 1 is made according to Examples 1-3. Therein, methallyl alcohol is first protected with a conventional hydroxyl protecting group, e.g. silylation with t-butyldiphenylsilyl chloride. Then the protected methallyl alcohol is hydroxylated by reacting with borane-tetrahydrofuran followed by hydrogen peroxide-sodium hydroxide in tetrahydrofuran (THF). Finally, the resultant material is oxidized to the corresponding aldehyde with oxalyl chloride-dimethylsulfoxide in methylene chloride in the presence of triethylamine.

Other hydroxyl protecting groups known in the art (See for example T. W. Greene, *Protective Groups in Organic Synthesis*, John Wiley & Sons, Inc., 1981; Chapter 2) which can be used include: t-butyldimethylsilyl, benzyl, p-methoxybenzyl, methoxymethyl, benzyloxycarbonyl, and the like.

The imine 2 is prepared according to Example 4, by treating aldehyde 1 with p-anisidine in methylene chloride at room temperature for from 1 to 3 hours in the presence of a drying agent, e.g., MgSO4. The imine 2 can be subsequently ring closed to the 3-azidoazetidinones, the 7-to 10-cis series, or the 3-phthalimidoazetidinones, the 3-to 6-cis series. Other amines which can also be used in this reaction for the purpose of generating an N-blocked azetidinone group include: benzylamine, p-methoxybenzylamine, 3,4-dimethoxybenzylamine, 2,4-dimethoxybenzylamine, allylamine, and the like.

The 3-to 6-cis series of compounds is made, as shown in Flow Sheet A by treating imine 2 with phthalimidoacetyl chloride and triethylamine in methylene chloride at 0° C. to room temperature for from 12 to 24 hours to produce a mixture of 3-cis-αMe and 3-cis-βMe isomers (See Ex. 4).

The 4-cis α-Me and β-Me compounds, which can be separated chromatographically, are produced by removing the p-methoxyphenyl protecting group from the azetidinone nitrogen with cerium ammonium nitrate (CAN) in acetonitrile-water at 0° C. for about 30 minutes (See Ex. 6).

Removal of the silyl protecting group with tetra-n-butylammonium fluoride (TBAF)-acetic acid in THF at 55° C. for about 18 hours provides the 5-cis α-Me and β-Me compounds (See Exs. 9,10).

The 6-cis α- and β- methyl isomers are obtained by ruthenium tetroxide (RuO4) oxidation of the alcohol to the acid in CH3CN—H2O)—CCl4 at room temperature for from 1 to 4 hours as seen in Exs. 13,14.

The 7- to 10-cis series of compounds is produced by the treatment of imine 2 with azidoacetyl chloride and triethylamine in methylene chloride at −70° C. to 0° C. for from 3 to 12 hours (See Ex. 16). Oxidative removal of the p-methoxyphenyl group with CAN at 0° C. produces the free NH 8-cis α-Me and β-Me compounds which can be separated chromatographically (See Ex. 17). Treatment with TBAF-HOAc at room temperature removes the silyl protecting group (see Ex. 18, 19) and RuO4 oxidation yields at room temperature the 10-cis beta-methyl and alpha-methyl compounds (see Exs. 20, 21).

Flow Sheet B illustrates the synthesis of 3-amido cis-azetidinones based on the 13-cis intermediate which can be prepared by the catalytic hydrogenation of 7-cis (See Ex. 28 Method A) or the N-methylhydrazine deacylation of 3-cis (See Ex 28, Method B). In the case of the catalytic hydrogenation of 7-cis, a solution of 7-cis in an organic solvent e.g., EtOH/EtOAc, may be hydrogenated over platinum oxide under hydrogen pressure at room temperature. In the case of the deacylation of 3-cis, N-methylhydrazine may be added to a solution of 3-cis in methylene chloride and allowed to react at room temperature for from 48 to 96 hours.

The 3-amino azetidinone, 13-cis, can be acylated with conventional acylating agents known in the penicillin and cephalosporin arts, but not generally known in the carbapenem series, to enhance antibacterial effectiveness. Such agents are well known to produce amido-substituted azetidinones, e.g. the 14-cis compounds, where R is a conventional group as described in the Merck Index, Tenth Edition, Published 1983 by Merck & Co. Inc., hereby incorporated by reference for this particular purpose. Representative examples include 2-amino-phenylacetamido, 2-amino-p-hydroxyphenylacetamido, mandelamido, 3,5-dichloro-4-pyridon-1-yl-acetamido, 1-H-tetrazolylacetamido, 2-amino-4-thiazolyl-alpha-methoxyimino-acetamido, cyanomethylthioacetamido, 4-ethyl-2,3-dioxo-1-piperazinylcarbonylamino-alpha-p-hydroxyphenyl-acetamido, 2-aminomethyl-phenylacetamido, carbamoylcarboxymethylene-1,3-dithietane carboxamide, 2-thienylacetamido, butylmercaptoacetamido, phenylacetamido, 4-amino-4-carboxybutyramido-, allylmercaptoacetamido, gamma-chlorocrotylmercaptoacetamido, phenoxyacetamido, 2-(1,4-cyclohexadien-1-yl)-2-aminoacetamido, alpha-sulfoacetamido, 2-amino-4-thiazolyl-alpha-carboxyisopropoxyiminoacetamido, 2-furyl-α-methoxyimino-acetamido and the like. Preferred as R: (a) allyloxy; (b) p-nitrobenzyloxy; and (c) phenoxymethyl.

The acylation can be conducted in methylene chloride solvent at 0° C. in the presence of an HX acceptor such as pyridine to produce the 14a-cis α-Me and β-Me allyloxycarbonylamino compounds (see Exs. 36, 34); 14b-cis α-Me and β-Me p-nitrobenzyloxy carbonylamino compounds (See Ex. 37); and 14c-cis α-Me and β-Me phenoxyacetamino compounds (See Exs. 38, 35).

The 14-cis amido compounds can then be converted to the carboxylic acid intermediates 17-cis by the same series of reactions as for the 7-cis and 3-cis compounds of Flow Sheet A; e.g., removal of the N-protecting group by CAN leads to the 15-cis compounds (See Exs. 39,40,41); desilylation with TBAF produces the 16-cis compounds (See Exs. 45,46); and oxidation with $RuO_4$ provides the 17-cis compounds (See Exs. 53,54).

Flow Sheets C–E illustrate the preparation of the corresponding trans forms of the above azetidinone intermediates.

The 3- to 6-trans series, as shown in Flow Sheet C, can be produced by the same series of reactions described above in Flow Sheet A, but first the 3-cis must be epimerized to 3-trans by refluxing in a solvent such as benzene with a base, e.g., 1,8-diazabicyclo[5.4.0]undec-7-ene (DBU), to form the 3-trans mixture (See Ex. 5). Removal of the N-protecting group with CAN yields the 4-trans α-Me and β-Me compounds which as in the cis case can be separated chromatographically (See Ex. 7). Removal of the O-silyl group with TBAF-HOAc provides the 5-trans compounds (See Exs 8 and 11); and $RuO_4$ oxidation produces the 6-trans carboxylic acids (see Exs. 12,15).

As shown in Flow Sheet D, the amido compounds, 17-trans, can be produced by a parallel series of reactions starting with the removal of the phthalimido group of 3-trans by N-methylhydrazine in methylene chloride at room temperature to yield the 13-trans amino compounds (See Ex. 29) followed by chromatographic separation into the faster eluting α-Me isomer and the slower β-Me isomer.

The free amine of the 13-trans compounds can be acylated with the conventional penicillin/cephalosporin amido side chains described above to provide the 14-trans compounds (See Exs. 30,31,32,33).

The 14-trans compounds can then be N-deprotected with can to the 15-trans compounds (See Exs. 42,43,44); desilylated with TBAF-HOAc to the 16-trans series (see Exs. 47,48); and oxidized with $RuO_4$ to the 17-trans compounds (See Ex. 49, Method B, Ex. 55).

The 17-trans amido compounds can also be produced by a route off of the previously described 3- to 6-trans phthalimido series starting with 5-trans (see Flow Sheet E). 5-trans is first converted to the 11-trans acetonide by acid catalyzed ring closure with dimethoxypropane in THF at 50° C. for from 24 to 48 hours (See Ex. 22, 23). Suitable acid catalysts for this reaction include (±)-10-camphorsulfonic acid, p-toluenesulfonic acid and the like. This step is followed by removal of the phthalimido group of 11-trans with N-methylhydrazine in methylene chloride at room temperature to give the free amine side chain and acylation with conventional acylating agents as described above to give 12-trans (See Exs. 24,25,26,27). Finally, 12-trans is oxidized by Jones Reagent in acetone at room temperature for from 1 to 3 hours to the corresponding 17-trans compounds (See Exs. 49, Method A, 50,51,52).

Flow Sheet F illustrates the conversion of the 6-cis phthalimido and 10-cis azido azetidinone intermediates to the corresponding 2-(substituted-thio)-carbapenems, 30-cis.

Treatment of either 6-cis or 10-cis with carbonyldiimidazole (CDI) followed by anhydrous magnesium p-nitrobenzyl malonate yields the corresponding 18-cis compounds (See Exs. 57,58,60,61). This reaction is carried-out by first adding CDI to a solution of 6-cis or 10-cis in a polar solvent such as acetonitrile or N,N-dimethylformamide at room temperature followed after about 30 minutes by the addition of the magnesium p-nitrobenzyl malonate; the reaction mixture is then heated at between 50° C. and 80° C. for from 6 to 24 hours. Treatment of 18-cis with dodecylbenzenesulfonyl azide and triethylamine in acetonitrile at room temperature for from 1 to 4 hours yields the diazo-β-ketoester 19-cis materials (See Exs. 63,64,66,67). Compounds 19-cis may be cyclized to the bicyclic β-ketoesters 20-cis by heating with a catalytic amount of rhodium octanoate in an organic solvent at temperatures of from 40° C. to 80° C. for from 15 to 75 minutes (See Exs. 68,69,72). Suitable organic solvents include benzene, chloroform and ethyl acetate. Treating a solution of 20-cis in acetonitrile at −20° C. with diisopropylethylamine and trifluoromethanesulfonic anhydride followed by reaction in situ of the resulting enol trifluoromethanesulfonate with an appropriate thiol and diisopropylethylamine at −20° C. to 0° C. yields carbapenem esters 21-cis (see Ex. 73,74). Appropriate thiols, RSH, include such where R can be a conventional side chain group in the carbapenem antibiotic art including phenyl, cyanoethyl, p-nitrobenzyloxycarbonylaminoethyl, and the like. These thiols are further illustrated in U.S. Pat. No. 4,748,162 by Leanza, et al., assigned to Merck & Company, Inc., which is hereby incorporated by reference. Finally, removal of the p-nitrobenzyl protecting group from the carboxyl by hydrogenation at one atmosphere over palladium on carbon in the presence of potassium bicarbonate in tetrahydrofuran-ethanol-water at room temperature for from 1 to 4 hours provides the carbapenems 30-cis (See Ex. 135, Method B).

Flow Sheet G illustrates the corresponding parallel process for converting the 6-trans phthalimido and 17-trans-amido intermediates into the corresponding 2-(substituted-thio) carbapenems, 30-trans. Firstly, the 18-trans compounds are produced, like the cis materials, by treating 6-trans and 17-trans with CDI and magnesium p-nitrobenzyl malonate (See Exs. 56, 59). 18-trans is converted to the diazo-β ketoesters, 19-trans compounds, by treatment with dodecylbenzenesulfonylazide and triethylamine (See Exs. 62,65). Rhodium octanoate catalyzes 19-trans ring closure to the 20-trans (See Exs. 70,71). Subsequently, 20-trans many be converted to the 2-thio-substituted compounds, 21-trans, by treating with diisopropylethylamine and trifluoromethanesulfonic anhydride followed by a thiol (See Ex. 75,76,77). Finally compound 21-trans is deprotected to the carbapenems 30-trans (See Ex. 37, Method B).

Flow Sheet H illustrates the synthesis of trans-6-amido-1-methyl-2-H-carbapenems via Wittig cyclization of phosphorane intermediates 23-trans. Phosphoranes 23-trans are prepared from azetidinone intermediates 4-trans or 15-trans by one of two methods. The first method calls for acylation of the azetidinone nitrogen with allyl oxalyl chloride-pyridine in methylene chloride at −30° C. to room temperature for from 1 to 8 hours to produce the oxalimide intermediates 22-trans (See Exs. 78,79,80,81). Reduction of 22-trans with triethylphosphite in the presence of excess triphenylphosphine by heating in toluene at 90° C. to 110° C. for from 12 to 24 hours provides the ylides 23-trans (see Exs. 82 Method A, 83 Method A, 84,85). The second method calls for condensation of the azetidinone with allyl glyoxylate in methylene chloride promoted by triethylamine in the presence of a drying agent such as 4A molecular sieves. Chlorination of the resulting hemiaminal intermediate with thionyl chloride-2,6-lutidine in THF at −30° C., followed by reaction with triphenylphosphine and 2,6-lutidine in N,N-dimethylformamide at 80° C. for from 12 to 36 hours to produces the ylides 23-trans (See Ex. 82 Method B and 83 Method B).

The 23-trans materials are then desilylated TBAF-HOAc in THF at room temperature to 50° C. for from 12 to 48 hours to yield 24-trans (See Exs. 86,87,88,89). The alcohol 24-trans is oxidized with acetic anhydride/dimethylsulfoxide at room temperature to 50° C. for from 4 to 24 hours with concomitant ring closure of the intermediate aldehyde to produce the allyl-protected carbapenems, 25-trans (See Exs. 90,91,92,93). Finally, 25-trans is deprotected (See Ex. 142) by treatment with tetrakis(triphenylphosphine)-palladium and potassium 2-ethylhexanoate in ethyl acetate-methylene chloride at 0° C. to yield the 31-trans compounds.

Flow Sheet I illustrates the conversion of 6-cis and 17-cis azetidinone carboxylic acids to the title compounds, 30-cis. The first step involves forming the thioesters 26-cis by reacting the above mentioned carboxylic acids with an appropriate thiol, RSH, where R can be a conventional side-chain in the carbapenem art as delineated above, in a suitable inert solvent, e.g. acetonitrile, with a dehydrating agent such as dicylohexylcarbodiimide (DCC) present (See Exs. 94,95,96,107,108).

The next step involves attaching the alloxalyl group to the azetidinone nitrogen through acylation with allyl oxalyl chloride in a solvent, e.g. methylene chloride, in the presence of a base such as pyridine at 0° C. to room temperature for from 1–8 hours to produce the 27-cis compounds (See Ex. 109,110,115,122,123).

This step is followed by a one-step conversion of the 27-cis compounds to the 28-cis phosphorane compounds by treatment with excess triethyl phosphite in toluene at 90° C. to 110° C. for from 1 to 4 hours. The phosphorane 28-cis is cyclized by heating in refluxing p-xylene in the presence of hydroquinone for from 1 to 12 hours to produce the 29-cis compounds (See Exs. 124,125).

In a final step, the 29-cis compounds are carboxyl deprotected with tetrakis(triphenylphosphine)palladium and potassium 2-ethylhexanoate in ethyl acetate-methylene chloride at 0° C. to yield the 30-cis compounds (See Exs. 135 Method A, 138).

Flow Sheet J is a substantially identical process flow sheet for the analogous trans compounds. The 6-trans and 17-trans intermediates are converted to the 26-trans thioester compounds (See Exs, 97,98,99,100,101,102,103,104,105) and then to the N-alloxalyl derivatives 27-trans (See Exs. 111,112,113,114,116,117,118,119,120,121). As before a one step conversion to the phosphorane compounds 28-trans is followed by cyclization and to the 29-trans 2-(substituted-thio)carbapenems (See Exs. 126,127,128,129,130,131,132,133,134). Finally, removed of the allyl ester yields the title compounds 30-trans (See Exs. 136,137 Method A, 139,140,141).

The novel compounds in the different chemical classes of the present disclosure are believed to be valuable antibacterials active against various Gram-positive and Gram-negative bacteria and accordingly find utility in human and veterinary medicine. Representative pathogens which are sensitive to antibacterials herein: *Staphylococcus aureus* and *Escherichia coli*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium. phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semisolid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg. to about 1500 mg. of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The following examples are illustrative of the invention and should not be construed as being limits on the scope and spirit of the instant invention.

EXAMPLE 1

3-(t-Butyldiphenylsilyloxy)-2-methyl-1-propene

To solution of methallyl alcohol (12.6 ml, 150 mmol) and imidazole (15.3 g, 225 mmol) in 55 ml of dry DMF was added t-butyldiphenylsilyl chloride (39.0 ml, 15 mmol) dropwise with ice-bath cooling. After stirring at room temperature for 48 hrs the reaction mixture was poured into hexane-ether (50:1) and washed successively with water, saturated $NaHCO_3$, and brine. Drying ($Na_2SO_4$) and evaporation under reduced pressure gave 50.5 g of a pale yellow oil which was purified by flash chromatography through 600 g of silica gel ( 50:1 hexane/ether) to yield 41.10 g (88%) of the title compound as a colorless oil.

EXAMPLE 2

(±)-3-(t-Butyldiphenylsilyloxy)-2-methyl-1-propanol

To a solution of the above olefin (41.10 g, 132.4 mmol) in 170 ml of THF at 0° C., was added dropwise a solution of $BH_3$ THF (1.0M, 53.0 ml, 53.0 mmol). After stirring at room temperature for 3 hrs, the reaction mixture was re-cooled to 0° C. and 2N NaOH (42 ml) was added followed by dropwise addition of 30% $H_2O_2$ (21 ml). The resulting mixture was stirred at room temperature for 2 hrs before being poured into hexane-ether (6:4) and washed successively with water (3×) and brine. Drying ($MgSO_4$) and evaporation under reduced pressure gave 43.5 g (100%) of the title compound as a colorless oil which was used in the next reaction without purification.

EXAMPLE 3

(±)-3-(t-Butyldiphenylsilyloxy)-2-methylpropanal (1)

To a solution of oxalyl chloride (12.7 ml, 146 mmol) in 730 ml of dry $CH_2Cl_2$ at −70° C. was added a solution of DMSO (14.1 ml, 199 mmol) in 35 ml of $CH_2Cl_2$. After stirring 5 min., a solution of the alcohol prepared above (43.5 g, 132 mmol) in 65 ml of $CH_2Cl_2$ was added dropwise. After stirring 15 min at −70° C., $Et_3N$ (55 ml, 395 mmol) was added and the solution allowed to stir an additional 5 min before warming to room temperature. After 1 hr, the reaction mixture was concentrate by evaporation under reduced pressure and the concentrated poured into hexane-ether (8:2) and washed successively with water (3×), saturated $NH_4Cl$, saturated $NaHCO_3$ and brine. Drying ($MgSO_4$) and evaporation under reduced pressure gave 42.3 g of pale yellow oil which was purified by flash chromotagraphy through 650 g of silica gel (10% $Et_2O$/hexane) to yield 37.1 g of the aldehyde (1) as a white oily solid (86% yield).

| $^1$H NMR (200 MHz,$CDCl_3$): | | |
|---|---|---|
| δ | 1.04 | (Sit-Bu, s) |
| | 1.11 | ($CH_3$, d, J = 7.55 Hz) |
| | 2.55 | (CH—$CH_3$, m) |
| | 3.87 | ($CH_2$OSi, m) |
| | 7.4–7.7 | (—$SiPh_2$, m) |
| | 9.80 | (CHO, d, J = 1.56 Hz) |

IR (neat): 1770 cm$^{-1}$ (aldehyde)

EXAMPLE 4

(±)-1-(p-methoxyphenyl)-4R-(1S and 1R-methyl-2-t-butyldiphenylsilyloxyethyl)-3S-phthalimido-azetidin-2-one (3-cis-αMe and 3-cis-βMe)

To a solution of the aldehyde 1 (2.598 g, 7.969 mmol) in 20 ml of $CH_2Cl_2$ was added freshly sublimed p-anisidine (0.980 g, 7.97 mmol) and $MgSO_4$ (5 g) and the mixture was stirred at room temperature. After 2 hrs the mixture was filtered, diluted with benzene, and evaporated to leave a yellow oil. Formation of the imine 2 was verified by the $^1$H NMR spectrum (200 MHz, $CDCl_3$) which showed complete disappearance of the aldehydic proton and the formation of a new doublet at δ7.87 (J=5.57 Hz). The crude imine was dissolved in 50 ml of $CH_2Cl_2$, cooled to 0° C., and $Et_3N$ (1.90 ml, 13.6 mmol) was added followed by slow dropwise addition of a solution of phthalimidoacetyl chloride (2.49 g, 11.2 mmol) in 10 ml of $CH_2Cl_2$ during 30 min. After 4 hrs at 0° C. the yellow solution was allowed to warm to room temperature and stir for 16 hrs. The solution was diluted into EtOAc and washed successively with 1N HCl, sat. $NaHCO_3$, and brine. Drying ($MgSO_4$) and evaporation gave 5.0 g of a brown oil. Flash chromatography through 500 g of silica gel (2:3 EtoAc/hexane) yielded 2.49 g (49.5%) of product as a pale yellow foam which was a mixture of α and β-methyl isomers (1:1 by NMR).

A larger scale reaction starting with 41.40 g of aldehyde produced 85 g of crude product. This material was dissolved in $Et_2O$ and after several minutes a tan precipitate deposited and was isolated by filtration (8.2 g). This solid consisted of nearly pure β-methyl isomer. The filtrate was flash chromatographed through 1300 g of silica gel (1:2:7 $Et_2O$/hexane/$CH_2Cl_2$) to yield an additional 36.7 of product as a white foam which was a mixture of α-and β-methyl isomers (3:2 by NMR). The total yield was thus 44.9 g (59%).

| α-methyl isomer: | | |
|---|---|---|
| $^1$H NMR (200 MHz, $CDCl_3$): | | |
| δ | 0.71 | (CH$CH_3$, d, J = 6.64 Hz) |
| | 1.10 | (Sit-Bu, s) |
| | 2.1 | (CH$CH_3$, m) |
| | 3.50 | ($CH_2$OSi, m) |
| | 3.77 | (O$CH_3$, s) |
| | 4.53 | ($H_4$, dd, J = 5.4, 10.8 Hz) |
| | 5.55 | ($H_3$, d, J = 5.4) |
| | 6.8–7.9 | (Aromatic, m) |

β-methyl isomer:
¹H NMR (200 MHz, CDCl₃):

| δ | | |
|---|---|---|
| 1.05 | CH-CH₃, Sit-Bu bs | |
| 2.1 | CH-CH₃, m | |
| 3.45 | CH₂OSi, m | |
| 3.81 | OCH₃, s | |
| 4.63 | H₄, dd, J = 5.29, 9.1 | |
| 5.53 | H₃, d, J = 5.29 Hz | |
| 6.9–7.9 | Aromatic, m | |

| IR (CHCl₃): | |
|---|---|
| 1780 | Phthalimide |
| 1750 | β-lactam |
| 1720 cm⁻¹ | Phthalimide |
| FAB-MS: | M/e = 619 (M + H) |

EXAMPLE 5

(±)-1-(p-methoxyphenyl)-4R-(1S and 1R-methyl-2-t-butyldiphenylsilyloxyethyl)-3R-phthalimido-azetidin-2-one (3-trans-αMe and 3-trans-βMe)

To a solution of the azetidinones 3-cis (2.41 g, 3.90 mmol. 1:1 ratio by NMR) in benzene was added 1,8-diazabicylo[5.4.0]undec-7-ene (0.58 ml, 3.9, mmol) and the solution was heated to reflux. After 40 h an aliquot was removed and analyzed by ¹H NMR which showed the equilibration to be complete (trans/cis=30:1). The solution was cooled to room temperature, diluted with Et₂, and washed successively with sat. NH₄Cl and brine. Drying (MgSO₄) and evaporation gave 2.41 g (100%) of product as a yellow foam which required no purification.

α-methyl isomer:
¹H NMR (200 MHz, CDCl₃):

| δ | | |
|---|---|---|
| 0.83 | (CHCH₃, Sit-Bu, bs) | |
| 2.50 | (CHCH₃, m) | |
| 3.5–3.8 | (CH₂OSi, ABX) | |
| 3.79 | (OCH₃, s) | |
| 4.85 | (H₄, dd, J = 2.9, 4.7) | |
| 5.29 | (H₃, d, J = 2.9 Hz) | |
| 6.9–7.9 | (Aromatic, m) | |

β-methyl isomer:
¹H NMR (200 MHz, CDCl₃):

| δ | | |
|---|---|---|
| 1.05 | (Sit-Bu, s) | |
| 1.15 | (CHCH₃, d, J = 6.91 Hz) | |
| 2.35 | (CHCH₃, m) | |
| 3.5–3.8 | (CH₂OSi, ABX) | |
| 3.8 | (OCH₃, s) | |
| 4.55 | (H₄, dd, J = 2.7, 5.0 Hz) | |
| 5.87 | (H₃, d, J = 2.7 Hz) | |
| 6.9–7.9 | (Aromatic, m) | |

| IR (CHCl₃): | |
|---|---|
| 1775 | (phthalimide) |
| 1750 | (β-lactam) |
| 1720 cm⁻¹ | (phthalimide) |
| FAB-MS: | M/e = 619 (M + H) |

EXAMPLE 6

(±)-4R-(1S-methyl-2-t-butyldimethylsilyloxyethyl)-3S-phthalimido-azetidin-2-one and
(±)-4R-(1R-methyl-2-t-butyldimethylsilyloxyethyl)-3S-phthalimido-azetidin-2-one (4-cis-αMe and 4-cis-βMe)

A solution of the azetidinones 3-cis (1.60 g, 2.59 mmol, α-Me/β-Me=3:2 by NMR) in 25 ml of CH₃CN and 10 ml of THF was cooled to 0° C. and a solution of ceric ammonium nitrate (4.26 g, 7.77 mmol) in 13 ml of H₂ was added dropwise. After 30 min, the orange reaction mixture was diluted with EtOAc and washed successively with H₂ (2×), 10% Na₂SO₃ (2×), sat. NaHCO₃, and brine. Drying (MgSO₄) and evaporation gave a brown foam which was separated by flash chromatography through 150 g of silica gel (4:1 CH₂Cl₂-Et₂O) to yield the faster running (α-methyl isomer (0.530 g, 40%) and the more polar β-methyl isomer (0.360 g, 27%) as colorless foams.

α-methyl isomer:
¹H NMR (200 MHz, CDCl₃):

| δ | | |
|---|---|---|
| 0.72 | (CHCH₃, d, J = 6.56) | |
| 1.08 | (Sit-Bu, s) | |
| 1.97 | (CHCH₃, m) | |
| 3.65 | (CH₂OSi, ABX) | |
| 3.82 | (H₄, dd, J = 5.65, 10.27 Hz) | |
| 5.42 | (H₃, dd, J = 5.65, 1.91 Hz) | |
| 5.74 | (NH, bs) | |
| 7.4–7.75 | (SiPh₂, m) | |
| 7.75–7.95 | (Phthalimido, m) | |
| IR (CHCl₃): | 3440 (NE), 1785 (phthalimido), 1765 (β-lactam), 1725 cm⁻¹ (phthalimido) | |
| FAB-MS: | M/e = 513 (M + H) | |

β-methyl isomer:
¹H NMR (200 MHz, CDCl₃):

| δ | | |
|---|---|---|
| 0.95 | (Sit-Bu, s) | |
| 1.14 | (CHCH₃, d, J = 6.63 Hz) | |
| 2.05 | (CHCH₃, m) | |
| 3.34 | (CH₂OSi, m) | |
| 3.97 | (H₄, dd, J = 5.08, 10.48) | |
| 5.42 | (H₃, dd, J = 5.08, 1.59 Hz) | |
| 6.17 | (NH, bs) | |
| 7.2–7.6 | (SiPh₂, m) | |
| 7.7–7.85 | (Phthalimido, m) | |
| IR (CHCl₃): | 3440 (NH), 1785 (phthalimido), 1765 (β-lactam), 1725 cm⁻¹ (phthalimido) | |
| FAB-MS: | M/e = 513 (M + H) | |

IR (CHCl₃): 3440 (NH), 1785 (phthalimido), 1765 (β-lactam), 1725 cm⁻¹ (phthalimido)

| FAB-MS: | M/e = 513 (M + H) |
|---|---|

EXAMPLE 7

(±)-4R-(1S-methyl-2-t-butyldimethylsilyloxyethyl)-3R-phthalimido-azetidin-2-one and
(±)-4R-(1R-methyl-2-t-butyldimethylsilyloxyethyl)-3R-phthalimido-azetidin-2-one (4-trans-αMe and 4-trans-βMe)

Following the procedure described above in Example 6 a mixture of the azetidinones 3-trans (2.41 g, 3.90 mmol, 1:1 ratio by NMR) gave 0.782 g (39%) of 4-trans-αMe and 0.738 g (37%) of 4-trans-βMe as pale yellow foams.

α-methyl isomer:
¹H NMR (200 MHz, CDCl₃):

| δ | | |
|---|---|---|
| 0.87 | (CH₃, d, J = 6.99 Hz) | |
| 1.05 | (SiPh₂, s) | |
| 1.98 | (CHCH₃, m) | |
| 3.5–3.7 | (CH₂OSi, ABX) | |
| 3.88 | (H₄, dd, J = 3.17, 9.52 Hz) | |
| 5.05 | (H₃, d, J = 3.17 Hz) | |
| 6.19 | (NH, bs) | |
| 7.4–7.7 | (SiPh₂, m) | |
| 7.7–7.9 | (Phthalimido, m) | |

IR (CHCl₃):

| 3440 | (NH) |
|---|---|
| 1780 | (Phthalimido) |
| 1765 | (β-lactam) |
| 1725 cm⁻¹ | (Phthalimido) |

FAB-MS:  M/e = 513 (M + H)

β-methyl isomer:
¹H NMR (200 MHz, CDCl₃):

| δ | | |
|---|---|---|
| 0.97 | (Sit-Bu, s) | |
| 1.11 | (CH₃, d, J = 6.98 Hz) | |
| 1.92 | (CHCH₃, m) | |
| 3.60 | (CH_AOSi, dd, J = 10.8, 3.8 Hz) | |
| 3.77 | (CH_BOSi, dd, J = 10.8, 4.45 Hz) | |
| 4.24 | (H₄, dd, J = 2.54, 6.98) | |
| 5.17 | (H₃, d, J = 2.54 Hz) | |
| 6.47 | (NH, bs) | |
| 7.3–7.7 | (SiPh₂, m) | |
| 7.7–7.9 | (Phthalimido, m) | |

IR (CHCl₃):

| 3440 | (NH) |
|---|---|
| 1780 | (Phthalimido) |
| 1765 | (β-lactam) |
| 1725 cm⁻¹ | (Phthalimido) |

EXAMPLE 8

(±)-4R-(1-hydroxy-2R-propyl)-3R-(N-phthalimido)-azetidin-2-one (5-trans,βMe)

To a solution of the silyl ether 4-trans-βMe (1.002 g, 1.957 mmol) in 6 ml of THF was added acetic acid (1.1, 20 mmol) followed by a solution of tetrabutylammonium fluoride in THF (1.0M 5.9 ml, 5.9 mmol). The solution was heated at 55° C. for 18 hrs and was then cooled to room temperature and evaporated in vacuo to leave a yellow solid. Purification by flash chromatography through 100 g of silica gel (30% THF/CH₂Cl₂) yielded 0.518 g (97%) of product as a white solid.

¹H NMR (200 MHz, d₆-acetone)

| δ | | | |
|---|---|---|---|
| | 1.05 | CH₃ | d, J = 6.98 Hz |
| | 1.95 | CHCH₃ | m |
| | 3.5–3.7 | CH₂O | m |
| | 4.02 | H₄ | dd, J = 2.54. 8.26 Hz |
| | 5.14 | H₃ | d, J = 2.54 Hz |
| | 7.9 | Phthalimido | s |

IR (nujol):

| 3400 | NH |
|---|---|
| 3300 | OH |
| 1765 | Phthalimido |
| 1755 | β-lactam |
| 1710 | Phthalimido |

EXAMPLE 9

(±)-4R-(1-hydroxy-2R-propyl)-3S-(N-Phthalimido)-azetidin-2-one (5-cis-βMe)

In manner analogous to that described above, the silyl ether 4-cis-βMe (0.645 g, 1.26 mmol) gave the title compound (0.215 g, 62%) as a white solid.

¹H NMR (200 MHz, d₆-DMSO):

| δ | | | |
|---|---|---|---|
| | 0.865 | CH₃ | d, J = 6.73 Hz |
| | 1.76 | CHCH₃ | m |
| | 3.04 | CH₂O | ABX |
| | 3.57 | H₄ | dd, J = 5.04, 10.52 Hz |
| | 4.37 | OH | t, J = 4.78 Hz |
| | 5.28 | H₃ | dd, J = 5.04, 1.3 Hz |
| | 7.85–7.95 | Phthalimido | m |
| | 8.59 | NH | bs |

EXAMPLE 10

(±)-4R-(1-hydroxy-2S-(propyl)-3S-(N-phthalimido)-azetidin-2-one (5-cis-αMe)

In a manner analogous to that describe above the silyl ether 4-cis-αMe (0.370 g, 0.723 mmol) gave the title compound (0.185 g, 93%) as a pale yellow solid.

¹H NMR (200 MHz, d₆-DMSO):

| δ | | | |
|---|---|---|---|
| | 0.581 | CH₃ | d, J = 6.56 |
| | 1.65 | CHCH₃ | m |
| | 3.2–3.5 | CH₂O | ABX |
| | 3.58 | H₄ | dd, J = 5, 10.9 Hz |
| | 4.52 | OH | t, J = 5.3 Hz |
| | 5.35 | H₃ | dd, J = 5.1, 1.3 Hz |
| | 7.9–8.0 | Phthalimido | m |
| | 8.61 | NH | bs |

EXAMPLE 11

(±)-4R-(1-hydroxy-2S-propyl)-3R-(N-phthalimido)-azetidin-2-one (5-trans-αMe)

In a manner analogous to that described above, the silyl ether 4-trans-αMe (0.782 g, 1.53 mmol) gave the title compound (0.380 g, 90%) as a white solid.

¹H NMR (200 MHz, d₆-DMSO):

| δ | | | |
|---|---|---|---|
| | 0.897 | CH₃ | d, J = 6.53 Hz |
| | 1.84 | CHCH₃ | m |
| | 3.3–3.5 | CH₂O | m |
| | 3.76 | H₄ | dd, J = 3.0, 8.57 Hz |
| | 4.63 | OH | t, J = 5.0 Hz |
| | 5.01 | H₃ | d, J = 3.0 Hz |
| | 7.9–8.0 | Phthalimido | m |
| | 8.6 | NH | bs |

EXAMPLE 12

(±)-4R-(1R-carboxyethyl)-3R-N-phthalimido-azetidin-2-one (6-trans-βMe)

To a solution of the alcohol 5-trans-βMe (145 mg, 0.529 mmol) in 11 ml of acetonitrile and 4 ml of water was added 4 ml of carbon tetrachloride followed by a solution of sodium metaperiodate (340 mg, 1.59 mmol, 3 eq.) in 2 ml of water and a solution of ruthenium trichloride hydrate (7 mg, 0.05 eq.) in 0.5 ml of water. The two phase mixture was vigorously stirred at room temperature for 3 hrs and was then partitioned between EtOAc/THF (1:1) and brine. The organic phase was diluted with toluene and evaporated to dryness in vacuo. The residual tan solid was extracted with THF and filtered and the filtrate was evaporated to yield 148.6 mg (97%) of product as an off-white solid. This material was difficult to purify due to its low solubility in most organic solvents and was thus used without purification in subsequent reactions.

| $^1$H NMR (200 MHz, d$_6$-DMSO): | | |
|---|---|---|
| δ | 1.15 | CH$_3$ | d, J = 6.99 Hz |
| | 2.76 | CHCH$_3$ | m |
| | 3.98 | H4 | dd, J = 2.54, 8.25 Hz |
| | 5.16 | H3 | d, J = 2.54 Hz |
| | 7.9–8.0 | Phthalimido | m |
| | 8.73 | NH | bs |
| | 2.45 | CO$_2$H | bs |

EXAMPLE 13

(±)-4R-(1R-carboxyethyl)-3S-N-phthalimido-azetidin-2-one (6-cis-βMe)

In a analogous manner to that described above, the alcohol 5-cis-βMe (0.102 g, 0,372 mmol) gave the title carboxylic acid (0.107 g, 99.8%) as a tan solid.

| $^1$H NMR (200 MHz, d$_6$-DMSO): | | |
|---|---|---|
| δ | 1.19 | CH$_3$ | d, J = 6.98 Hz |
| | 2.5 | CHCH$_3$ | m |
| | 3.90 | H4 | dd, J = 5.08, 10.33 Hz |
| | 5.44 | H3 | dd, J = 5.08, 1.12 Hz |
| | 7.9–8.0 | Phthalimido | m |
| | 8.8 | NH | bs |
| | 12.3 | CO$_2$H | bs |

EXAMPLE 14

(±)-4R-(1S-carboxyethyl)-3S-N-phthalimido-azetidin-2-one (6-cis-αMe)

In an analogous manner to that described above, the alcohol 5-cis-αMe (0.105 g, 0.381 mmol) gave the corresponding carboxylic acid (0.109 g, 98.8%) as a tan solid.

| $^1$H NMR (200 MHz, d$_6$-DMSO): | | |
|---|---|---|
| δ | 0.867 | CH$_3$ | d, J = 6.98 Hz |
| | 2.55 | CHCH$_3$ | m |
| | 3.95 | H4 | dd, J = 5.08, 10.79 Hz |
| | 5.45 | H3 | dd, J = 5.08, 1.34 Hz |
| | 7.95–8.05 | phthalimido | m |
| | 8.74 | NH | bs |

EXAMPLE 15

(±)-4R-(1S-carboxyethyl)-3R-N-phthalimido-azetidin-2-one (6-trans-αMe)

In an analogous manner to that described above, the alcohol 5-trans-αMe (0.109 g, 0.396 mmol) yielded the corresponding carboxylic acid (0.113 g, 99.1%) as a tan solid.

| $^1$H NMR (200 MHz, d$_6$-DMSO): | | |
|---|---|---|
| δ | 1.14 | CH$_3$ | d, J-6.91 Hz |
| | 2.77 | CHCH$_3$ | m |
| | 3.99 | H4 | dd, J = 2.54, 8.89 Hz |
| | 5.11 | H3 | d, J = 2.54 Hz |
| | 7.9–8.0 | Phthalimido | m |
| | 8.7 | NH | m |

EXAMPLE 16

(±)-3S-Azido-1-p-methoxyphenyl-4R-(1S and 1R-methyl-2-t-butyldiphenylsilyloxyethyl)-azetidin-2-one (7-cis-αMe and 7-cis-βMe)

To a solution of the aldehyde 1 (49.55 g, 151.8 mmol) in 100 ml of methylene chloride was added freshly sublimed p-anisidine (18.69, 151.8 mmol) followed by 50 g of magnesium sulfate. After stirring at room temperature for 2 hrs, the mixture was filtered and evaporated to leave a light yellow oil. Formation of the imine 2 was established by the $^1$H NMR spectrum (200 MHz, CDCl$_3$) which showed complete disappearance of the aldehydic proton and the formation of a new doublet at δ7.87 (J=5.57 Hz).

The crude imine was dissolved in 1000 ml of methylene chloride, cooled to −70° C., and triethylamine (34.2 ml, 245 mmol) was added followed by dropwise addition of azidoacetyl chloride (25.3 g, 212 mmol). The reaction mixture was stirred at −70° C. for 30 min and then the dry-ice bath was replaced with an ice bath and stirring was continued for an additional 3 hrs as the light orange solution became dark brown. The reaction mixture was washed sucessively with 1N HCl, sat. NaHCO$_3$ and brine. Drying (MgSO$_4$) and evaporation gave a brown tar which was purified flash chromatography though 1500 g of silica gel (2:3 Et$_2$O/hexane) to yield 60.0 g (76.8%) of cis-cycloadducts as a pale yellow foam (α-Me/β-Me ratio approximately 5:3 by 1H NMR).

| $^1$H NMR (300 MHz, CDCl$_3$): | |
|---|---|
| δ | 0.91 | (β-CH$_3$, d, J = 7.21 Hz) |
| | 0.94 | (α-CH$_3$, d, J = 7.32 Hz) |
| | 1.11 | (β Sit-Bu, s) |
| | 1.12 | (α Sit-Bu, s) |
| | 2.2–2.4 | (α + β CHCH$_3$, m) |
| | 3.5–3.8 | (α + β CH$_2$O, m) |
| | 3.78 | (α OCH$_3$, s) |
| | 3.79 | (β OCH$_3$, s) |
| | 4.40 | (α H4, dd, J = 5.5, 6.9 Hz) |
| | 4.70 | (α H3, d, J = 5.5 Hz) |
| | 4.6–4.7 | (β H3 + H4, m) |
| | 6.8–7.7 | (α + β Aromatic Protons, m) |

IR (CHCl$_3$): 2120 (azide), 1750 cm$^{-1}$ (β-lactam)
FAB-MS: M/e=515 (M+H)

EXAMPLE 17

(±)-3S-Azido-4R-(1S-methyl-2-t-butyldiphenylsilyoxyethyl)-azetidin-2-one and
(±)-3S-Azido-4R-(1R-methyl-2-t-butyldiphenylsilyloxyethyl)-azetidin-2-one (8-cis-αMe and 8-cis-βMe)

A solution of the azetidinones 7-cis (1.486 g, 2.887 mmol (α-Me/β-Me ratio approx. 5:3 by NMR) in 20 ml of acetonitrile was cooled to 0° C. and a solution of ceric ammonium nitrate (4.75 g, 8.67 mmol) in 10 ml of water was added dropwise. After 30 min the orange solution was diluted with ethyl acetate and washed successively with water (2×), 10% $Na_2SO_3$ (2×), sat. $NaHCO_3$. and brine. Drying ($MgSO_4$) and evaporation gave a brown oil which was separated by flash chromatography on 125 g of silica gel (1:6:3 $Et_2O/CH_2Cl_2$/hexane) to yield 0.509 g (43.2%) of the faster eluting α-methyl isomer and 0.267 g (22.6%) of the more polar β-methyl isomer as white solids.

α-methyl isomer:
$^1$H NMR (200 MHz, $CDCl_3$):

| δ | | |
|---|---|---|
| 0.94 | ($CH_3$, d, J = 6.56 Hz) | |
| 1.05 | (Sit-Bu, s) | |
| 1.9 | (C$\underline{H}$CH$_3$, m) | |
| 3.59 | (H4, dd, J = 5.01, 10.25 Hz) | |
| 3.63 | ($CH_2$OSi, d, J = 4.73) | |
| 4.68 | (H3, dd, J = 5.01, 2.25 Hz) | |
| 5.7 | (NH, bs) | |
| 7.4–7.7 | ($SiPh_2$ m) | |

β-methyl isomer:
$^1$H NMR (200 MHz, $CDCl_3$):

| δ | | |
|---|---|---|
| 1.05 | $CH_3$, d, J = 6.63 Hz | |
| 1.06 | (Sit-Bu, s) | |
| 1.95 | (C$\underline{H}$CH$_3$, m) | |
| 3.6–3.7 | ($CH_2$OSi, m) | |
| 3.76 | (H4, dd, J = 5.08, 7.69 Hz) | |
| 4.41 | (H3, dd, J = 5.08, 2.40 Hz) | |
| 5.85 | (NH, bs) | |
| 7.4–7.7 | ($SiPh_2$, m) | |

EXAMPLE 18

(±)-3S-Azido-4R-(1-hydroxy-2S-propyl)-azetidin-2-one (9-cis-(αMe)

In a manner analogous to that described in Example 8, except that the reaction was carried-out at room temperature for 27 hrs, the silyl ether 8-cis-αMe (0.509 g, 1.25 mmol) gave the corresponding alcohol (0.188 g, 88.5%) as a yellow solid.

$^1$H NMR ($CDCl_3$):

| δ | | | |
|---|---|---|---|
| 0.92 | $CH_3$ | d, J = 6.70 Hz | |
| 1.95 | C$\underline{H}$CH$_3$ | m | |
| 1.45–1.85 | $CH_2$O | m | |
| 3.57 | H4 | dd, J = 6, 10 Hz | |
| 4.7 | H3 | dd, J = 6, 2 Hz | |
| 6.4 | NH | bs | |

EXAMPLE 19

(±)-3S-Azido-4R-(1-hydroxy-2R-propyl)-azetidin-2-one (9-cis-βMe)

In a manner analogous to that described above, the silyl ether 8-cis-βMe (0.267 g, 0.654 mmol) gave the corresponding alcohol (0.0977 g, 88%) as a white solid.

$^1$H NMR (200 MHz, $CDCl_3$):

| δ | | |
|---|---|---|
| 0.99 | $CH_3$ | d, J = 6.92 Hz |
| 2.05 | C$\underline{H}$CH$_3$ | m |
| 3.5–3.8 | $CH_2$O | m |
| 3.76 | H4 | dd, J = 5.08, 8.32, Hz |
| 4.77 | H3 | dd, J = 5.08, 2.54 Hz |
| 6.2 | NH | bs |

EXAMPLE 20

(±)-3S-Azido-4R-(1R-carboxyethyl)-azetidin-2-one (10-cis-βMe)

In a analogous manner to that described in Example 12, the alcohol 9-cis-βMe (78.8 mg, 0.463 mmol) gave the title carboxylic acid (55.0 mg, 64.5%) as an off-white solid.

$^1$H NMR (200 MHz, $d_6$-acetone):

| δ | | |
|---|---|---|
| 1.27 | $CH_3$ | d, J = 7.30 Hz |
| 2.57 | C$\underline{H}$CH$_3$ | dq, J = 9.88, 7.30 Hz |
| 3.99 | H4 | dd, J = 4.98, 9.88 Hz |
| 5.01 | H3 | dd, J = 4.98, 2.44 Hz |
| 7.85 | NH | bs |

EXAMPLE 21

(±)-3S-Azido-4R-(1S-carboxyethyl)-azetidin-2-one (10-cis-αMe)

In a manner analogous to that described above, the alcohol 9-cis-αMe (122.1 mg, 0.718 mmol) gave the corresponding carboxylic acid (45.5 mg, 34.4%) as an off-white solid.

$^1$H NMR (200 MHz, $d_6$-acetone):

| δ | | |
|---|---|---|
| 1.21 | $CH_3$ | d, J = 7.06 Hz |
| 2.63 | C$\underline{H}$CH$_3$ | dq, J = 10.08, 7.06 Hz |
| 3.89 | H4 | dd, J = 5.00, 10.08 Hz |
| 5.00 | H3 | dd, J = 5.00, 1.83 Hz |
| 7.7 | NH | bs |

EXAMPLE 22

(±)-(5R,6R,7R)-7-N-phthalimido-2,2,5-trimethyl-3-oxa-1-azabicyclo[4.2.0]octan-8-one (11-trans-βMe)

To a suspension of the alcohol 5-trans-βMe (0.512 g, 1.87 mmol) in 25 ml of tetrahydrofuran and 10 ml of 2,2-dimethoxypropane was added (±)-10-camphorsulfonic acid (0.215 g, 0.927 mmol) and the mixture was heated to 50° C. After several hours the reaction mixture became a clear solution. After heating for 42 hrs, the solution was cooled to room temperature, diluted with ethyl ether, and washed with sat. $NaHCO_3$ and brine. Drying ($MgSO_4$) and evaporation left a yellow solid which was purified by flash chromatography on 60 g of silica gel (15:20:65 $EtOAc$/hexane/$CH_2Cl_2$) to yield 0.349 g (59.5%) of the acetonide as a white solid.

$^1$H NMR (200 MHz, $CDCl_3$):

| δ | | | |
|---|---|---|---|
| 1.25 | C$\underline{H}$CH$_3$ | d, J = 6.99 Hz | |
| 1.55, 1.79 | C($CH_3$)$_2$ | 2s | |
| 1.95 | CHC$\underline{H}_3$ | m | |
| 3.61 | O$\underline{CH}$-α | dd, J = 12.1, 2.85 Hz | |

| 3.96 | OCH-β | dd, J = 12.1, 2.23 Hz |
| 4.17 | H4 | dd, J = 2.22, 5.08 Hz |
| 5.24 | H3 | d, J = 2.22 |
| 7.7–7.9 | Aromatic | m |

IR (CHCl₃): 1780 (phthalimide), 1760(β-lactam), 1720 cm⁻¹ (phthalimide)

| FAB-MS: | M/e = 315 | (M + H) |

EXAMPLE 23

(±)-(5S,6R,7R)-7-N-phthalimido-2,2,5-trimethyl-3-oxa-1-azabicyclo[4.2.0]octan-8-one(11-trans-αMe)

In a manner analogous to that described above, the azetidinone 5-trans-αMe (13.8 mg, 0.0504 mmol) gave the title acetonide (9.6 mg, 61%) as a white solid.

¹H NMR (200 MHz, CDCl₃):
| δ | 0.93 | CHCH₃ | d, J = 6.99 Hz |
| | 1.56, 1.84 | C(CH₃)₂ | 2s |
| | 1.95 | CHCH₃ | m |
| | 3.50 | OCH-α | dd, J = 12.1, 12.1 Hz |
| | 3.53 | H4 | dd, J = 1.90, 12 Hz |
| | 3.78 | OCH-β | dd, J = 12.1, 4.55 Hz |
| | 5.05 | H3 | d, J = 1.90 Hz |
| | 7.7–7.9 | Aromatic | m |

IR (CHCl₃): 1780 (phthalimide), 1760 (β-lactam), 1720 cm⁻¹ (phthalimide)

| FAB-MS: | M/e = 315 | (M + H) |

EXAMPLE 24

(±)-(5R,6R,7R)-7-allyloxycarbonylamino-2,2,5-trimethyl-3-oxa-1-azabicyclo[4.2.0]octan-8-one (12a-trans-βMe)

To a solution of the phthalimide 11-trans-βMe (348.5 mg, 1.11 mmol) in 10 ml of methylene chloride was added methyl hydrazine (0.24 ml, 4.5 mmol). After stirring for 38 hrs at room temperature, the mixture was filtered and evaporated to give 271 mg of a pale yellow oil. The crude amine was dissolved in 11 ml of methylene chloride, cooled to 0° C., and diisopropylethylamine (0.48 ml, 2.8 mmol) and allylchloroformate (0.21 ml, 2.0 mmol) were added. After 2 hrs the reaction mixture was diluted with ethyl ether and washed successively with sat. NH₄Cl, sat. NaHCO₃, and brine. Drying (MgSO₄) and evaporation gave a yellow oil which was separated by flash chromatography through 35 g of silica gel (3:2 EtOAc/hexane) to yield 275 mg (92%) of product as a white solid.

¹H NMR (200 MHz, CDCl₃):
| δ | 1.16 | CHCH₃ | d, J = 6.98 Hz |
| | 1.43, 1.72 | C(CH₃)₂ | 2s |
| | 2.0 | CHCH₃ | m |
| | 3.55 | CH_AO | dd, J = 12.38, 2.80 Hz |
| | 3.73 | H4 | broad d, J = 4.76 Hz |
| | 3.91 | CH_BO | dd, J = 12.38, 2.54 Hz |
| | 4.63 | H3 | broad d, J = 7.62 Hz |
| | 4.5–4.6 | CH₂C = C | m |
| | 5.2–6.0 | NH, vinyl | m, 4H |

| | protons | |

IR (CHCl₃); 3450 (NH), 1750 (β-lactam), 1725 cm⁻¹ (carbamate)

EXAMPLE 25

(±)-(5R,6R,7R)-7-p-nitrobenzyloxycarbonylamino-2,2,5-trimethyl-3-oxa-1-azabicylo [4.2.0]octan-8-one (12b-trans-βMe)

In a manner analogous to that described above, except that acylation was performed with p-nitrobenzylchloroformate-pyridine, the phthalimide 11-trans-βMe (108.8 Mg, 0.346 mmol) gave 123 mg (98%) of the title compound as a white solid.

¹H NMR (200 MHz, CDCl₃):
| δ | 1.15 | CHCH₃ | d, J = 6.92 Hz |
| | 1.42, 1.71 | C(CH₃)₂ | 2s |
| | 2.0 | CHCH₃ | bs |
| | 3.55 | CH_AO | dd, J = 11.99, 2.47 Hz |
| | 3.74 | H4 | dd, J = 1.55, 4.73 Hz |
| | 3.91 | CH_BO | dd, J = 11.99, 2.22 Hz |
| | 4.66 | H3 | dd, J = 1.55, 7.65 Hz |
| | 5.19 | CO₂CH₂ | s |
| | 5.71 | NH | broad d, J = 7.65 Hz |
| | 7.48, 8.20 | Aromatic Protons | 2d, J = 9.0 Hz |

EXAMPLE 26

(±)-(5R,6R,7R)-7-phenoxyacetamido-2,2,5-trimethyl-3-oxa-1-azabicyclo[4.2.0]octan-8-one (12c-trans-βMe)

In a analogous manner to that described above, except that acylation was conducted with phenoxyacetyl chloride-pyridine, the phthalimide 11-trans-βMe (65.1 mg, 0.297 mmol) gave 40.7 mg (62%) of the title amide as a white solid.

¹H NMR (200 MHz, CDCl₃):
| δ | 1.22 | CHCH₃ | d, J = 6.92 Bz |
| | 1.45, 1.75 | C(CH₃)₂ | 2s |
| | 2.05 | CHCH₃ | m |
| | 3.58 | CH_AO | dd, J = 11.93, 2.40 Hz |
| | 3.74 | H4 | dd, J = 1.94, 4.55 Hz |
| | 3.93 | CH_BO | dd, J = 11.93, 2.0 Hz |
| | 4.50 | CH₂OPh | s |
| | 4.91 | H3 | dd, J = 1.94, 7.40 Hz |
| | 7.15 | NH | broad d, J = 7.4 Hz |
| | 6.9–7.4 | OPh | m |

IR (CHCl₃): 3430 (NH), 1750 (β-lactam), 1685 cm⁻¹ (amide)

| FAB-MS: | M/e = 319 | (M + H) |

EXAMPLE 27

(±)-(5S, 6R, 7R)-7-allyloxycarbonylamino-2,2,5-trimethyl-3-oxa-1-azabicyclo[4.2.0]octan-8-one (12a-trans-αMe)

In the same manner described in Example 24, the phthalimide 11-trans-αMe (16.5 mg, 0.0525 mmol ) yielded the title carbamate (11.5 mg, 82%) as a white solid.

¹H NMR (200 MHz, CDCl₃):

| δ | | |
|---|---|---|
| 1.01 | CHC$\underline{H}_3$ | d, J = 6.66 Hz |
| 1.85 | C$\underline{H}$CH₃ | m |
| 3.15 | H4 | broad, d, J = 10.16 Hz |
| 3.45 | CH$_A$O | dd, J = 12.06, 11.12 Hz |
| 3.73 | CH$_B$O | dd, J = 12.06, 4.44 Hz |
| 4.45 | H3 | broad, d, J = 6.98 Hz |
| 4.6 | CH₂C = C | m |
| 5.6 | NH | bs |
| 5.2–5.4, 5.9–6.1 | Vinyl Protons | m |

IR (CHCl₃): 3450 (NH), 1755 (β-lactam), 1725 cm⁻¹ (carbamate)

| FAB-MS: | M/e = 269 | (M + H) |
|---|---|---|

EXAMPLE 28

(±)-3S-amino-1-p-methoxyphenyl-4R-(1S-methyl-2-t-butyl diphenylsilyloxy-ethyl)azetidin-2-one and
(±)-3S-amino-1-p-methoxyphenyl-4R-(1R-methyl-2-t-butyl diphenylsilyloxyethyl)-azetidin-2-one
(13-cis-αMe and 13-cis-βMe)

Method A:

A solution of the azides 7-cis (59.00 g, 114.6 mmol, α-Me/β-Me ratio approx. 5:3) in 300 ml of ethyl acetate-ethanol (1:1) was hydrogenated over 6 g of platinum oxide at 40 psi in a Parr apparatus at room temperature. The vessel was vented and refilled with hydrogen occasionally to release the nitrogen which was generated in the reduction. After 6 hrs the mixture was filtered through celite and evaporated to leave a brown foam. Purification by flash chromatography through 1600 g of silica gel (1:1 EtOAc/CH₂Cl₂+1% MeOH) yielded 16.13 g (28.8%) of the faster eluting β-methyl isomer and 23.25 g (41.5%) of the more polar α-methyl isomer as pale yellow foams.

Method B:

To a solution of the phthalimido azetidinones 3-cis (14.43 g, 23.32 mmol, α-Me/β-Me=1:1 by NMR) in 230 ml of CH₂Cl₂ was added methyl hydrazine (1.86 ml, 35.0 mmol) and the solution was stirred at room temperature. After 48 hrs the reaction was not complete (by TLC) and another portion of methyl hydrazine (1.24 ml, 23.3 mmol) was added. The reaction mixture was stirred for an addition 48 hrs and was then filtered and evaporated to leave a yellow foam. Separation by flash chromatography through 700 g of silica gel (1:1 EtOAc/CH₂CH₂+1% MeOH) yielded the faster running β-methyl isomer (2.88 g, 25%) and the more polar α-methyl isomer (2.87 g, 25%) as pale yellow foams.

| α-methyl isomer: ¹H NMR (200 MHz, CDCl₃): | | |
|---|---|---|
| δ 1.02 | (CH₃, d, J=6.92Hz) | |
| 1.08 | (Sit-Bu, s) | |
| 1.6–1.7 | (NH₂, bs) | |
| 2.28 | (C$\underline{H}$CH₃, m) | |
| 3.66 | (CH₂OSi, ABX) | |
| 3.77 | (OCH₃), s) | |
| 4.22 | (H4, dd, J=5.6, 6.2Hz) | |
| 4.34 | (H3, d, J=5.6Hz) | |
| 6.8–7.7 | (Aromatic, m) | |

| IR (CHCl₃): | |
|---|---|
| 3400 | (NH₂) |
| 1740 cm⁻¹ | (β-lactam) |

| FAB-MS: | |
|---|---|
| M/e = 489 | (M + H) |

| β-methyl isomer: ¹H NMR (200 MHz, CDCl₃): | |
|---|---|
| δ 0.93 | (CH₃, d, J=6.99Hz) |
| 1.11 | (Sit-Bu, s) |
| 1.5–1.6 | (NH₂, bs) |
| 2.3 | (C$\underline{H}$CH₃, m) |
| 3.6–3.8 | (CH₂OSi, ABX) |
| 3.78 | (OCH₃, s) |
| 4.31 | (H3, d, J=5.57Hz) |
| 4.45 | (H4, dd, J=5.57, 5.43Hz) |
| 6.83, 7.35 | (methoxyphenyl, AB, J=8.75Hz) |
| 7.4–7.8 | (SiPh₂, m) |

| IR(CHCl₃): | |
|---|---|
| 3400 | (NH₂) |
| 1735 cm⁻¹ | (β-lactam) |

| FABS-MS: | |
|---|---|
| M/e = 489 | (M + H) |

EXAMPLE 29

(±)-3R-Amino-1-p-methoxyphenyl-4R-(1S-methyl-2-t-butyldiphenylsilyloxy-ethyl)-azetidin-2-one and
(±)-3R-Amino-1-p-methoxyphenyl-4R-(1R-methyl-2-t-butyl diphenylsilyloxyethyl)-azetidin-2-one
(13-trans-αMe and 13-trans-βMe)

To a solution of the phthalimidoazetidinones 3-trans (11.60 g, 18.75 mmol, α-Me/β-Me=3:2 by NMR) in 190 ml of CH₂Cl₂ was added methyl hydrazine (1.49 ml, 28.0 mmol). After stirring at room temperature for 48 hrs the reaction mixture was filtered to remove white precipatate that had formed and the filtrate was evaporated under reduced pressure to give a white foam. Separation by flash chromatography through 800 g of silica gel (1:1 EtOAc/CH₂Cl₂+1% MeOH) yielded 3.63 g (39.8%) of the faster running α-methyl isomer as a pale yellow oil and 2.33 g (25.5%) of the more polar β-methyl isomer as a white foam.

| α-methyl isomer: ¹H NMR (200 MHz, CDCl₃): | | |
|---|---|---|
| δ | 0.83 | (CH₃, d, J = 6.99 Hz) |
| | 1.11 | (Sit-Bu, s) |
| | 1.4–1.6 | (NH₂, bs) |
| | 2.38 | (C$\underline{H}$CH₃, m) |
| | 3.6–3.8 | (CH₂OSi, ABX) |
| | 3.79 | (OCH₃, s) |
| | 4.03 | (H4, dd, J = 2.33, 3.95 Hz) |
| | 4.08 | (H3, d, J = 2.33 Bz) |
| | 6.83, 7.27 | (Methoxyphenyl, AB, J = 9.35 Hz) |
| | 7.3–7.7 | (SiPh₂, m) |

| IR (CHCl₃): | |
|---|---|
| 3400 | (NH₂) |
| 1760 cm⁻¹ | (β-lactam) |

| FAB-MS: | M/e = 489 | (M + H) |
|---|---|---|

β-methyl isomer:
¹H NMR (200 MHz, CDCl₃):

| δ | 1.05 | (Sit-Bu, s,) |
|---|---|---|
| | 1.08 | (CH₃, d, J = 6.91 Hz) |
| | 1.6–1.8 | (NH₂, bs) |
| | 2.34 | (CHCH₃, m) |
| | 3.6 | (CH₂OSi, ABX) |
| | 3.78 | (OCH₃, s) |
| | 3.93 | (H4, dd, 3 = 2.2, 4.6 Hz) |
| | 4.29 | (H3, d, J = 2.2 Hz) |
| | 6.8–7.7 | (Aromatics, m) |

| IR(CHCl₃): | |
|---|---|
| 3400 | (NH₂) |
| 1740 cm⁻¹ | (β-lactam) |

| FAB-MS:p | | |
|---|---|---|
| M/e = 489 | | (M + H) |

EXAMPLE 30

(±)-4R-(1-t-butyldiphenylsilyloxy-2R-propyl)-1-p-methoxyphenyl-3R-p-nitrobenzyloxycarbonylamino-azetidin-2-one(14b-trans-βMe)

A solution of the amine 13-trans-βMe (2.33 g, 4.77 mmol) in 50 ml of methylene chloride was cooled to 0° C. and pyridine (0.58 ml, 7.2 mmol) was added followed by p-nitrobenzylchloroformate (1.34 g, 6.22 mmol). After 3 h the reaction mixture was diluted with ethyl acetate an washed successively with saturated NH₄Cl saturated NaHCO₃, and brine. Drying (MgSO₄) and evaporation gave an oil which was purified by flash chromatography through 200 g of silic gel (1:1 EtOAc/hexane) to yield 2.94 g (92.3%) of the carbamate as a light yellow foam.

| ¹H NMR (CDCl₃): | | |
|---|---|---|
| δ 1.03 | Sit-Bu | s |
| 1.15 | CH₃ | d, J=6.98 |
| 2.4 | CHCH₃ | m |
| 3.5–3.8 | CH₂OSi | m |
| 3.77 | OCH₃ | s |
| 4.27 | H4 | bs |
| 5.15 | H3 | broad d, J=8Hz |
| 5.25 | CO₂CH₂— | s |
| 5.6 | NH | broad d, J=8Hz |
| 6.8–8.4 | aromatic protons | m, 18H |

IR (CHCl₃): 3450(NH), 1745(β-lactam), 1730cm⁻¹(carbamate) FAB-MS: m/e=668 (M+H)

EXAMPLE 31

(±)-4R-(1-t-butyldiphenylsilyloxy-2R-propyl)-1-p-methoxyphenyl-3R-phenoxyacetamido-azetidin-2-one (14c-trans-βMe)

In an analogous manner to that described above, the amine 13-trans-βMe (47.9 mg, 0.0982 mmol) was reacted with phenoxyacetyl chloride to give the amide (51 mg, 83%) as a white solid.

| ¹H NMR (200 MHz, CDCl₃): | | |
|---|---|---|
| δ 1.05 | Sit-Bu | s |
| 1.10 | CH₃ | d, J=6.99Hz |
| 2.4 | CHCH₃ | m |
| 3.5–3.7 | CH₂OSi | ABXm |
| 3.78 | OCH₃ | s |
| 4.19 | E4 | dd, J=2.72, 4.52Hz |
| 4.53 | CH₂OPh | s |
| 5.42 | H₃ | dd, J=2.72, 8.61Hz |
| 7.15 | NH | broad d, J=8.6Hz |
| 6.8–7.7 | aromatic protons | m, 19H |

IR (CHCl₃): 3420(NH), 1750(β-lactam), 1695cm⁻¹(amide) FAB-MS: M/e=623 (M+H)

EXAMPLE 32

(±)-4R-(1-t-butyldiphenylsilyloxy-2S-propyl)-1-p-methoxyphenyl-3R-p-nitrobenzyloxycarbonylamino-azetidin-2-one (14b-trans-α-Me)

In a manner analogous to that described above, the amine 13-trans-αMe (3.45 g, 7.06 mmol) gave the title carbamate (4.53 g, 96.1%) as a pale yellow foam.

| ¹H NMR (200 MHz, CDCl₃): | | |
|---|---|---|
| δ 0.82 | CH₃ | d, J=6.99Hz |
| 1.07 | Sit-Bu | s |
| 2.44 | CHCH₃ | m |
| 3.6–3.75 | CH₂OSi | m |
| 3.78 | OCH₃ | s |
| 4.4 | H₄ | bs |
| 4.77 | H₃ | broad d, J=8.2Hz |
| 5.1–5.3 | CO₂CH₂— | AB |
| 5.8 | NH | broad d, J=8.2Hz |
| 6.8–8.2 | aromatic protons | m, 18H |

IR (CHCl₃): 3440(NH), 1740(β-lactam), 1730cm⁻¹(carbamate) FAB-MS: M/e=668 (M+H)

EXAMPLE 33

(±)-3R-allyloxycarbonylamino-4R-(1-t-butyldiphenyl-silyloxy-2S-propyl)-1-p-methoxyphenyl-azetidin-2-one (14a-trans-αMe)

In a manner analogous to that described above, the amine 13-trans-αMe (0.690 g, 1.41 mmol) was reacted with allyl chloroformate to give the title carbamate (666 mg, 83%) as a pale yellow foam.

| ¹H NMR (200 MHz, CDCl₃): | | |
|---|---|---|
| δ 0.82 | CH₃ | d, J=6.98Hz |
| 2.4 | CHCH₃ | m |
| 3.7–3.8 | CH₂OSi | m |
| 3.78 | OCH₃ | s |
| 4.4 | H₄ | broad s |
| 4.55 | CH₂C═C | m |
| 4.75 | H₃ | broad d, J=8Hz |
| 5.15–6.0 | NH, vinyl protons | m, 4H |
| 6.8–7.7 | aromatic protons | m, 14H |

IR (CHCl$_3$): 3450(NH), 1750($\beta$-lactam), 1725cm$^{-1}$(carbamate) FAB-MS: M/e=573 (M+H)

EXAMPLE 34

($\pm$)-3S-allyloxycarbonylamino-4R-(1-t-butyldiphenyl-silyloxy-2R-propyl)-1-p-methoxyphenyl-azetidin-2-one (14a-cis-$\beta$Me)

In a manner analogous to that described above, the amine 13-cis-$\beta$Me (0.805 g, 1.65 mmol) was reacted with allyl chloroformate to yield the title carbamate (0.863 g, 91.5%) as a colorless foam.

| $^1$H NMR (200 MHz, CDCl$_3$): | | |
|---|---|---|
| $\delta$ 1.02 | CH$_3$ | d, J=7.45Hz |
| 1.12 | Sit-Bu | s |
| 2.3 | CHCH$_3$ | m |
| 3.5-3.7 | CH$_2$OSi | ABx |
| 3.81 | OCH$_3$ | s |
| 4.5-4.7 | H$_4$, CH$_2$C=C | m, 3H |
| 5.2-6.1 | H$_3$, NH, vinyl protons | m, 5H |
| 6.8-7.7 | aromatic protons | m, 14H |

IR (CHCl$_3$): 3440(NH), 1740($\beta$-lactam), 1725cm$^{-1}$(carbamate) FAB-MS: M/e=573 (M+H)

EXAMPLE 35

($\pm$)-4R-(1-t-butyldiphenylsilyloxy-2-R-propyl)-1-p-methoxyphenyl-3S-phenoxyacetamido-azetidin-2-one 14c-cis-$\beta$Me)

In a manner analogous to that described above, the amine 13-cis-$\beta$Me (56.2 mg, 0.115 mmol) was reacted with phenoxyacetyl chloride to give the title amide (56.8 mg, 79%) as a colorless oil.

| $^1$H NMR (200 MHz, CDCl$_3$): | | |
|---|---|---|
| $\delta$ 0.74 | CH$_3$ | d, J=7.05Hz |
| 1.08 | Sit-Bu | s |
| 1.97 | CHCH$_3$ | m |
| 3.4-3.6 | CH$_2$OSi | m |
| 3.78 | OCH$_3$ | s |
| 4.4-4.6 | CO$_2$CH$_2$ | AB |
| 4.73 | H$_4$ | dd, J=5.85, 4.05Hz |
| 5.51 | H$_3$ | dd, J=5.85, 8.99Hz |
| 6.7-7.7 | NH, aromatic protons | m, 20H |

IR (CHCl$_3$): 3430(NH), 1750($\beta$-lactam), 1695cm$^{-1}$(amide) FAB-MS: M/e=623 (M+H)

EXAMPLE 36

($\pm$)-3S-allyloxycarbonylamino-4R-(1-t-butyldiphenyl-silyloxy-2S-propyl)-1-p-methoxyphenyl-azetidin-2-one (14a-cis-$\alpha$Me)

In a manner analogous to that described above, the amine 13-cis-$\beta$Me (5.00 g, 10.2 mmol) was reacted with allyl chloroformate to yield the title carbamate (5.82 g, 99%) as a white solid.

| $^1$H NMR (300 MHz, CDCl$_3$): | | |
|---|---|---|
| $\delta$ 0.98 | CH$_3$ | d, J=8.24Hz |
| 1.08 | Sit-Bu | s |
| 2.15 | CHCH$_3$ | m |
| 3.48 | CH$_2$OSi | d, J=6.05Hz |
| 3.78 | OCH$_3$ | s |
| 4.37 | H$_4$ | t, J=5.3Hz |
| 4.58 | CO$_2$CH$_2$— | d, J=4.39Hzs |
| 5.15-5.35 | C=CH$_2$ | m |
| 5.36 | H$_3$ | dd, J=5.3, 9.7Hz |
| 5.8-6.0 | CH=C | m |
| 6.17 | NH | d, J=9.7Hz |
| 6.8-7.6 | aromatic protons | m, 14H |

IR (CHCl$_3$): 3430(NH), 1750($\beta$-lactam), 1730cm$^{-1}$(carbamate) FAB-MS: M/e=573 (M+H)

EXAMPLE 37

($\pm$)-4R-(1-t-butyldiphenylsilyloxy-2S-propyl)-1-p-methoxyphenyl-3S-p-nitrobenzyloxycarbonylamino-azetidin-2-one(14b-cis-$\alpha$Me)

In an analogous manner to that described above, the amine 13-cis-$\alpha$Me (0.381 g, 0.781 mmol) gave the title carbamate (0.514 g, 99%) as a pale foam.

| $^1$NMR (200 MHz, CDCl$_3$): | | |
|---|---|---|
| $\delta$ 0.99 | CH$_3$ | d, J=7.30Hz |
| 1.06 | Sit-Bu | s |
| 2.2 | CHCH$_3$ | m |
| 3.48 | CH$_2$OSi | d, J=5.89Hz |
| 3.78 | OCH$_3$ | s |
| 4.39 | H$_4$ | dd, J=5.72, 3.43Hz |
| 5.17 | CO$_2$CH$_2$— | s |
| 5.36 | H$_3$ | dd, J=5.72, 10.13Hz |
| 6.47 | NH | d, J=10.13Hz |
| 6.81-8.16 | PNB aromatic | 2d, J=9.2Hz |
| 7.2-7.6 | SiPh$_2$ | m |

IR (CHCl$_3$): 3430,3360(NH), 1750($\beta$-lactam), 1730cm$^{-1}$(carbamate)

EXAMPLE 38

($\pm$)-4R-(1-t-butyldiphenylsilyloxy-2S-propyl)-1-p-methoxyphenyl-3S-phenoxyacetamido-azetidin-2-one (14c-cis-$\alpha$Me)

In an analogous manner to that described above, the amine 13-cis-$\alpha$Me (3.00 g, 6.14 mmol) was reacted with phenoxyacetyl chloride to yield the amide (3.55 g, 92.8%) as a white solid.

| $^1$H NMR (200 MHz, CDCl$_3$): | | |
|---|---|---|
| $\delta$ 0.84 | CH$_3$ | d, J=7.09Hz |
| 1.06 | Sit-Bu | s |
| 1.95 | CHCH$_3$ | m |
| 3.4-3.6 | CH$_2$OSi | m |
| 3.77 | OCH$_3$ | s |
| 4.38 | H$_4$ | dd, J=5.43, 7.27Hz |
| 4.35-4.55 | CH$_2$OPh | AB |
| 5.60 | H$_3$ | dd, J=5.43, 9.13Hz |
| 6.7-7.67 | NH, aromatic protons | m, 20H |

IR (CHCl$_3$): 3420, (NH), 1750($\beta$-lactam), 1695cm$^{-1}$(amide) FAB-MS: M/e=623 (M+H)

EXAMPLE 39

($\pm$)-3S-allyloxycarbonylamino-4R-(1-t-butyldiphenyl-silyloxy-2S-propyl)-azetidin-2-one (15a-cis-$\alpha$Me)

To a solution of the azetidinone 14a-cis-$\alpha$Me (4.91 g, 8.57 mmol) in 86 ml of acetonitrile cooled to $-20°$ C. was added dropwise a solution of ceric ammonium nitrate (14.14 g, 25.79 mmol) in 43 ml of water which had been buffered by the portionwise addition of sodium bicarbonate (2.17 g, 25.8 mmol). The orange reaction mixture was allowed to warm to 0° C. during 30 minutes and was then diluted with ethyl acetate and washed successively with water (2$\times$), 10% Na$_2$SO$_3$, saturated NaHCO₃, and brine. Drying (MgSO₄) and evaporation gave a brown foam which was purified by flash chromatography through 150 g of silica gel (1:1 EtOAc/hexane) to yield 3.21 g (80.2%) of the title compound as a white solid.

| ¹H NMR (200 MHz, CDCl₃): | | |
|---|---|---|
| δ 0.87 | CH₃ | d, J=6.63Hz |
| 1.07 | Sit-Bu | s |
| 1.7 | CHCH₃ | m |
| 3.5–3.7 | H₄, CH₂OSi | m, 3H |
| 4.55–4.65 | CH₂C=C | m |
| 5.1–6.0 | CH=CH₂, —O₂CNH, NH | m, 5H |
| 7.3–7.7 | SiPh₂ | m |

IR (CHCl₃): 3430,(NH), 1765(β-lactam), 1725cm⁻¹(carbamate) FAB-MS: M/e=467 (M+H)

EXAMPLE 40

(±)-4R-(1-t-butyldiphenylsilyloxy-2S-propyl)-3S-p-nitrobenzyloxycarbonylamino-azetidin-2-one (15b-cis-αMe)

In a manner analogous to that described above, except that buffering with sodium bicarbonate was not employed and the reaction temperature was 0° C. throughout, the azetidinone 14b-cis-αMe (0.506 g, 0.758 mmol) gave the title compound (0.350 g, 82.3%) as a pale yellow oil.

| ¹H NMR (200 MHz, CDCl₃): | | |
|---|---|---|
| δ 0.83 | CH₃ | d, J=6.59Hz |
| 1.06 | Sit-Bu | s |
| 1.7 | CHCH₃ | m |
| 3.5–3.7 | H₄, CH₂OSi | m, 3H |
| 5.1–5.3 | H₃, CO₂CH₂ | m, 3H |
| 5.76 | NE | bs |
| 6.01 | —O₂CNH | d, J=9.14Hz |
| 7.3–8.25 | aromatic protons | m, 14H |

EXAMPLE 41

(±)-4R-(1-t-butyldiphenylsilyloxy-2S-propyl)-3S-phenoxyacetamido-azetidin-2-one (15c-cis αMe)

In an analogous manner to that described above, the azetidinone 14c-cis-αMe (3.55 g, 5.70 mmol) gave the title compound (2.06 g, 69.9%) as a white solid.

| ¹H NMR (300 MHz, CDCl₃): | | |
|---|---|---|
| δ 0.79 | CH₃ | d, J=6.53Hz |
| 1.06 | Sit-Bu | s |
| 1.55 | CHCH₃ | m |
| 3.61 | CH₂OSi | d, J=4.21Hz |
| 3.67 | H₄ | dd, J=4.82, 10.38Hz |
| 4.53 | CO₂CH₂ | s |
| 5.41 | H₃ | ddd, J=9.64, 4.82, 2.0Hz |
| 5.64 | NH | s |
| 6.9–7.7 | O₂NH, ArH | m, 16H |

IR (CHCl₃): 3420,(NH), 1770(β-lactam), 1695cm⁻¹(amide) FAB-MS: M/e=517 (M+H)

EXAMPLE 42

(±)-4R-(1-t-butyldiphenylsilyloxy-2S-propyl)-3R-p-nitrobenzyloxycarbonylamino-azetidin-2-one (15b-trans-αMe)

In a manner analogous to that described above, the azetidinone 14b-trans-αMe (4.35 g, 6.51 mmol) gave the title compound (2.98 g, 81.4%) as a pale yellow foam.

| ¹H NMR (200 MHz, CDCl₃): | | |
|---|---|---|
| δ 0.93 | CH₃ | d, J=7.06Hz |
| 1.05 | Sit-Bu | s |
| 1.9 | CHCH₃ | m |
| 3.44 | H₄ | dd, J=2.15, 9.13Hz |
| 3.5–3.7 | CH₂OSi | m |
| 4.5 | H₃ | dd, J=2.15, 9.38Hz |
| 5.1–5.3 | CO₂CH₂— | AB |
| 5.4 | O₂CNH | broad d, J=9.4Hz |
| 5.95 | NH | bs |
| 7.3–8.3 | aromatic protons | m, 14H |

IR (CHCl₃): 3440,(NH), 1770(β-lactam), 1735cm⁻¹(carbamate) FAB-MS: M/e=562 (M+H)

EXAMPLE 43

(±)-3R-allyloxycarbonylamino-4R-(1-t-butyldiphenylsilyloxy-2S-propyl)-azetidin-2-one (15a-trans-αMe)

In a manner analogous to that described above, the azetidinone 14a-trans-αMe (0.656 g, 1.15 mmol) provided the title compound (0.386 g, 72.2%) as a pale yellow foam.

| ¹H NMR (200 MHz, CDCl₃): | | |
|---|---|---|
| δ 0.94 | CH₃ | d, J=6.64Hz |
| 1.9 | CHCH₃ | m |
| 3.47 | H₄ | dd, J=2.22, 9.52Hz |
| 3.5–3.7 | CH₂OSi | m |
| 4.45–4.65 | H₃, CH₂C=C | m, 3H |
| 5.1–6.0 | —O₂CNH, CH=CH₂ | m, 4H |
| 6.19 | NH | bs |
| 7.35–7.7 | SiPh₂ | m |

IR (CHCl₃): 3450,(NH), 1770(β-lactam), 1725cm⁻¹(carbamate) FAB-MS: M/e=467 (M+H)

EXAMPLE 44

(±)-4R-(1-t-butyldiphenylsilyloxy-2R-propyl)-3R-p-nitrobenzyloxycarbonylamino-azetidin-2-one 15b-trans-βMe)

In a manner analogous to that described above, the azetidinone 14b-trans-βMe (2.71 g, 4.06 mmol) Save the title compound (1.68 g, 73.7%) as a white foam.

| ¹H NMR (200 MHz, CDCl₃): | | |
|---|---|---|
| δ 0.97 | CH₃ | d, J=6.66Hz |
| 1.05 | Sit-Bu | s |
| 2.0 | CHCH₃ | m |
| 3.55–3.95 | H₄, CH₂OSi | m, 3H |
| 4.43 | H₃ | dd, J=2.54, 7.93Hz |
| 5.1–5.3 | CO₂CH₂— | AB |
| 5.34 | O₂CNH | d, J=7.93Hz |
| 5.97 | NH | bs |
| 7.3–8.3 | aromatic protons | m, 14H |

IR (CHCl₃): 3430,(NH), 1765(β-lactam), 1725cm⁻¹(carbamate) FAB-MS: M/e=562 (M+H)

EXAMPLE 45

(±)-4R-(1-hydroxy-2S-propyl)-3S-(p-nitrobenzyloxycarbonylamino)-azetidin-2-one (16b-cis-αMe)

To a solution of the silyl ether 15b-cis-αMe (0.350 g, 0.623 mmol) in 2 ml of tetrahydrofuran was added acetic acid (0.36 ml, 6.2 mmol) followed by a solution of tetrabutylammonium fluoride in tetrahydrofuran (1.0M, 1.90 ml, 1.90 mmol). The solution was heated at 55° C. for 14 h and was then cooled to RT and evaporated to leave a yellow oil. Purification by flash chromatography through 35 g of silica gel (1:1 THF/$CH_2Cl_2$) yielded 0.163 g, (80.9%) of the title compound as a white solid.

| $^1$H NMR (200 MHz, $d_6$-DMSO): | | |
|---|---|---|
| δ 0.76 | $CH_3$ | d, J=6.35Hz |
| 1.7 | C$\underline{H}$$CH_3$ | m |
| 3.2–3.6 | $H_4$, $CH_2O$ | m, 3H |
| 4.56 | OH | t, J=5Hz |
| 4.93 | $H_3$ | dd, J=4.20, 9.91Hz |
| 5.27 | $CO_2CH_2$— | s |
| 7.6–8.4 | ArH, 2NH | m, 6H |

FAB-MS: M/e=324 (M+H)

EXAMPLE 46

(±)-4R-(1-hydroxy-2R-propyl)-3S-(p-nitrobenzyloxycarbonylamino)-azetidin-2-one (16b-cis-βMe)

In a manner analogous to that described above the silyl ether 15b-cis-βMe (0.150 g, 0.267 mmol) gave the title alcohol (0.076 g, 88%) as a white solid.

| $^1$H NMR (200 MHz, $d_6$-DMSO): | | |
|---|---|---|
| δ 0.96 | $CH_3$ | d, J=6.67Hz |
| 1.8 | C$\underline{H}$$CH_3$ | m |
| 3.0–3.5 | $CH_2O$ | m |
| 3.45 | $H_4$ | dd, J=4.7, 9.8Hz |
| 4.55 | OH | t, J=5.4Hz |
| 4.87 | $H_3$ | ddd, J=1.5, 4.7, 9.5Hz |
| 5.27 | $CO_2CH_2$ | s |
| 7.6–8.4 | aromatic, 2NH | m, 6H |

FAB-MS: M/e=324 (M+H)

EXAMPLE 47

(±)-4R-(1-hydroxy-2R-propyl)-3R-(p-nitrobenzyloxycarbonylamino)-azetidin-2-one (16b-trans-βMe)

In a manner analogous to that described above, except that the reaction was carried-out at RT for 65 h, the silyl ether 15b-trans-βMe (0.214 g, 0.381 mmol) gave the title alcohol (0.112 g, 91%) as a pale yellow foam.

| $^1$H NMR (200 MHz, $CDCl_3$): | | |
|---|---|---|
| δ 0.92 | $CH_3$ | d, J=6.99Hz |
| 1.85 | C$\underline{H}$$CH_3$ | m |
| 3.35–3.70 | $H_4$, $CH_2O$ | m, 3H |
| 4.59 | $H_3$ | dd, J=1.27, 6.67Hz |
| 5.20 | $CO_2CH_2$ | s |
| 6.10 | $O_2CNH$ | d, J=6.67Hz |
| 6.60 | NH | bs |
| 7.48, 8.20 | aromatic | 2d, J=8.7Hz |

EXAMPLE 48

(±)-4R-(1-hydroxy-2S-propyl)-3S-(p-nitrobenzyloxycarbonylamino)-azetidin-2-one (16b-trans-αMe)

In a manner analogous to that described above, the silyl ether 15b-trans-αMe (0.242 g, 0.431 mmol) gave the corresponding alcohol (0.131 g, 88%) as a white solid.

| $^1$H NMR (200 MHz, $d_6$-acetone): | | |
|---|---|---|
| δ 0.98 | $CH_3$ | d, J=7.09Hz |
| 1.8 | C$\underline{H}$$CH_3$ | m |
| 3.48 | $H_4$ | dd, J=2.61, 8.89Hz |
| 3.5–3.6 | $CH_2O$ | m |
| 4.52 | $H_3$ | dd, J=2.61, 9.21Hz |
| 5.27 | $CO_2CH_2$ | s |
| 7.66, 8.25 | aromatic | 2d, J=8.7Hz |

EXAMPLE 49

(±)-4R-(1R-carboxyethyl)-3R-p-nitrobenzyloxycarbonylaminoazetidin-2-one (17b-trans-βMe)

Method A:

To a solution of the acetonide 12b-trans-βMe (113.3 mg, 0.312 mmol) in 2 ml of acetone at RT was added excess 2N Jones reagent (1.1 ml). After stirring for 1 h, isopropanol (0.5 ml) was added to consume the excess oxidant. After several minutes a large excess of anhydrous sodium sulfate was added and the mixture was vigorously stirred and then filtered, washing the salts with EtOAc-THF (3:1). Evaporation of the filtrate gave 110 mg of a yellow solid which was purified by flash chromatography through 5 g of silica gel (elution with 1:1 EtOAc/THF +0.5% HOAc) to yield 82 mg (78%) of the title carboxylic acid as a white solid.

Method B:

To a solution of the alcohol 16b-trans-βMe (0.101 g, 0.312 mmol) in 2 ml of acetonitrile and 2 ml of carbon tetrachloride were added a solution of sodium metaperiodate (0.201 g, 0.94 mmol) in 2.5 ml of water followed by a solution of ruthenium trichloride hydrate (3 mg, 0.01 mmol) in 0.5 ml of water. The two phase reaction mixture was vigorously stirred at RT for 1.5 h and was then partitioned between EtOAc/THF (1:1) and brine. The organic phase was diluted with toluene and evaporated to dryness in vacuo. The dark residue was flash chromatographed through 10 g of silica gel (100:100:1 EtOAc/THF/HOAc) to yield 91.8 mg (87%) of the carboxylic acid as a white solid.

| $^1$H NMR (200 MHz, $d_6$-acetone): | | |
|---|---|---|
| δ 1.32 | $CH_3$ | d, J=6.99Hz |
| 2.9 | C$\underline{H}$$CH_3$ | m |
| 3.93 | $H_4$ | dd, J=2.54, 7.3Hz |
| 4.73 | $H_3$ | dd, J=2.54, 8.89Hz |
| 5.33 | $CH_2O$ | s |
| 7.26 | $O_2CNH$ | broad d, J=9Hz |
| 7.54 | NH | bs |
| 7.73, 8.32 | aromatic | 2d, J=8.5Hz |

FAB-MS: M/e=388 (M+H)

EXAMPLE 50

(±)-3R-allyloxycarbonylamino-4R-(1R-carboxyethyl)-azetidin-2-one (17a-trans-βMe)

According to Method A described above, acetonide 12a-trans-βMe (54.0 mg, 0.201 mmol) gave the title carboxylic acid (42.8 mg, 88%) as a white solid.

| $^1$H NMR (200 MHz, d$_6$-acetone): | | | |
|---|---|---|---|
| δ | 1.31 | CH$_3$ | d, J=7.3Hz |
| | 2.8 | CHCH$_3$ | m |
| | 3.92 | H$_4$ | dd, J=2.54, 7.62Hz |
| | 4.6 | CH$_2$C=C | m |
| | 4.70 | H$_3$ | dd, J=2.54, 8.88Hz |
| | 5.2–6.1 | vinyl protons | m |
| | 7.09 | O$_2$CNH | broad d, J=8.9Hz |
| | 7.52 | NH | bs |

IR(Nujol): 3400 (NH), 3280 (OH), 1750 (β-lactam), 1720 (carbamate), 1690cm$^{-1}$ (carboxylic acid) FAB-MS: M/e=243 (M+H)

EXAMPLE 51

(±)-3R-allyloxycarbonylamino-4R-(1S-carboxyethyl)-azetidin-2-one (17a-trans-αMe)

According to Method A described above, the acetonide 12a-trans-αMe (5.1 mg, 0.019 mmol), gave the title carboxylic acid (4.5 mg, 97%) as a white solid.

| $^1$H NMR (200 MHz, d$_6$-acetone): | | | |
|---|---|---|---|
| δ | 1.33 | CH$_3$ | d, J=7.30Hz |
| | 2.8 | CHCH$_3$ | m |
| | 3.76 | H$_4$ | dd, J=2.54, 9.52Hz |
| | 4.6–4.7 | H$_3$, CH$_2$C=C | m, 3H |
| | 5.2–6.2 | vinyl protons | m |
| | 7.2 | —O$_2$CNH | broad d |
| | 7.5 | NH | bs |

EXAMPLE 52

(±)-4R-(1R-carboxyethyl)-3R-phenoxyacetamidoazetidin-2-one (17c-trans-β-Me)

Following Method A described above, except that no chromatography was carried-out, 40.7 mg (0.128 mmol) of acetonide 12c-trans-βMe yielded 33.5 mg (90%) of crude acid as a brown solid. This material was a single component by TLC on silica gel (3:1 EtOAc/THF) but satisfactory spectral data could not be obtained due to its insoluble nature. Thus it was used directly in subsequent reactions without characterization.

EXAMPLE 53

(±)-4R-(1S-carboxyethyl)-3S-p-nitrobenzyloxycarbonylamino-azetidin-2-one (17b-cis-αMe)

To a solution of the alcohol 16b-cis-αMe (79.0 mg, 0.244 mmol) in 4 ml of acetonitrile and 1 ml of water was added 3 ml of carbon tetrachloride followed by a solution of sodium metaperiodate (157 mg, 0.734 mmol) in 2 ml of water which had been adjusted to neutral pH with 1M NaHCO$_3$ (0.1 ml), and finally a solution of ruthenium trichloride hydrate (3 mg, 0.01 mmol, 0.05 equiv.) in 0.5 ml of water. The two-phase reaction mixture was vigorously stirred at RT for 4.5 h and was then partioned between EtOAc/THF (1:1) and brine. The organic phase was diluted with toluene and evaporated to dryness in vacuo. The dark residual solid was flash chromatographed through 5 g of silica gel (100:100:1 EtOAc/THF/HOAc) to yield 62.0 mg (75.2%) of the title carboxylic acid as a white solid.

| $^1$H NMR (200 MHz, d$_6$-DMSO): | | | |
|---|---|---|---|
| δ | 0.97 | CH$_3$ | d, J=7.06Hz |
| | 2.6 | CHCH$_3$ | m |
| | 3.69 | H$_4$ | dd, J=4.69, 10.48 Bz |
| | 4.97 | H$_3$ | dd, J=4.69, 9.45Hz |
| | 5.28 | CO$_2$CH$_2$ | s |
| | 7.6–8.5 | aromatic, 2 NH | m, 6H |

EXAMPLE 54

(±)-4R-(1R-carboxyethyl)-3S-p-nitrobenzyloxycarbonylamino-azetidin-2-one (17b-cis-βMe)

In a manner analogous to that described above except that buffering with NaHCO$_3$ was not employed, the alcohol 16b-cis-βMe (21.5 mg, 0.0666 mmol) gave the title carboxylic acid (19.3 mg, 86%) as a tan solid.

| $^1$H NMR (200 MHz, d$_6$-acetone): | | | |
|---|---|---|---|
| δ | 1.36 | CH$_3$ | d, J=7.41Hz |
| | 2.85 | CHCH$_3$ | m |
| | 4.03 | H$_4$ | dd, J=5.08, 9.77Hz |
| | 5.16 | H$_3$ | dd, J=5.08, 10Hz |
| | 5.25–5.35 | CO$_2$CH$_2$ | AB |
| | 6.35 | O$_2$CNH | d, J=10Hz |
| | 7.6–8.4 | aromatic | m |

EXAMPLE 55

(±)-4R-(1S-carboxyethyl)-3R-p-nitrobenzyloxycarbonylamino-azetidin-2-one (17b-trans-αMe)

In a manner analogous to that described above, the alcohol 16b-trans-αMe (0.122 g, 0.377 mmol) gave the title carboxylic acid (0.104 g, 81.67.) as a tan solid.

| $^1$H NMR (200 MHz, d$_6$-acetone): | | | |
|---|---|---|---|
| δ | 1.27 | CH$_3$ | d, J=7.44Hz |
| | 2.7 | CHCH$_3$ | m |
| | 3.72 | H$_4$ | dd, J=2.61, 9.59Hz |
| | 4.57 | H$_3$ | dd, J=2.61, 9.27Hz |
| | 5.28 | CO$_2$CH$_2$ | s |
| | 7.35 | O$_2$CNH | broad d, J=9.3Hz |
| | 7.43 | NE | bs |
| | 7.67, 8.26 | aromatic | 2d, J=8.8Hz |

EXAMPLE 56

(±)-4R-(1-p-nitrobenzyloxycarbonyl-2-oxo-3R-butyl)-3R-N-phthalimido-azetidin-2-one (18a-trans-βMe)

To a mixture of the carboxylic acid 6-trans-βMe (120.5 mg, 0.418 mmol) in 7.5 ml of acetonitrile was added carbonyldiimidazole (102 mg, 0.629 mmol). After stirring at RT for 2 h, the reaction mixture has become a homogenous solution and anhydrous magnesium p-nitrobenzyl malonate (290 mg, 0.579 mmol) was added. The stirred mixture was heated at 60° C. for 4 h and was then cooled to RT, diluted with EtOAc, and washed successively with 1N HCl, saturated NaHCO$_3$, and brine. Drying (MgSO$_4$) and evaporation gave 240 mg of a tan solid which was purified by flash chromatography through 25 g of silica gel (35:65 EtOAc/CH$_2$Cl$_2$) to yield 115 mg (59%) of the title β-ketoester as a white solid. The $^1$H NMR spectrum showed this material to be partially (approx. 25%) in the enol form. Chemical shifts are given for the keto-form only.

| ¹H NMR (200 MHz, CDCl₃): | | | |
|---|---|---|---|
| δ | 1.30 | CH₃ | d, J=6.99Hz |
|  | 3.02 | CHCH₃ | m |
|  | 3.5–3.7 | CH₂CO₂ | AB |
|  | 4.25 | H₄ | dd, J=2.54, 6.98Hz |
|  | 4.8–5.1 | CH₂O | AB |
|  | 5.07 | H₃ | d, J=2.54Hz |
|  | 6.24 | NH | bs |
|  | 7.5–8.2 | aromatic protons | m |

EXAMPLE 57

(±)-4R-(1-p-nitrobenzyloxycarbonyl-2-oxo-3R-butyl)-3S-N-phthalimido-azetidin-2-one (18a-cis-βMe)

In a manner analogous to that described above, the carboxylic acid 6-cis-βMe (44.3 mg, 0.154 mmol) gave the title β-ketoester (27.0 mg, 38%) as a colorless oil.

| ¹H NMR (200 MHz, CDCl₃): | | | |
|---|---|---|---|
| δ | 1.29 | CH₃ | d, J=7.19Hz |
|  | 3.2 | CHCH₃ | m |
|  | 3.2–3.4 | CH₂CO₂ | AB |
|  | 4.24 | H₄ | dd, J=5.22, 10.15Hz |
|  | 4.84, 4.95 | CH₂O | AB, J=13.4 |
|  | 5.54 | H₃ | dd, J=5.22, 1.55Hz |
|  | 6.15 | NH | bs |
|  | 7.3–8.3 | aromatic protons | m |

EXAMPLE 58

(±)-4R-(1-p-nitrobenzyloxycarbonyl-2-oxo-3S-butyl)-3S-N-phthalimido-azetidin-2-one (18a-cis-αMe)

In an analogous manner to that described above, except that N,N-dimethylformamide was used as a co-solvent for the reaction, the carboxylic acid 6-cis-αMe (38.5 mg, 0.134 mmol) yielded the title β-ketoester (33.5 mg, 54%) as a yellow oil.

| ¹H NMR (200 MHz, CDCl₃): | | | |
|---|---|---|---|
| δ | 0.98 | CH₃ | d, J=7.2Hz |
|  | 3.06 | CHCH₃ | m |
|  | 3.5–3.7 | CH₂CO₂ | AB |
|  | 4.05 | H₄ | dd, J=5.29, 10.37Hz |
|  | 5.29 | CH₂O | s |
|  | 5.49 | H₃ | dd, J=5.29, 1.69Hz |
|  | 6.25 | NH | bs |
|  | 7.55, 8.24 | PNB aromatic | AB, J=8.8Hz |
|  | 7.8–8.0 | phthalimido aromatic | m |

EXAMPLE 59

(±)-3R-p-nitrobenzyloxycarbonylamino-4R-(1-p-nitrobenzyloxycarbonyl-2-oxo-3R-butyl)-azetidin-2-one (18c-trans-βMe)

In an analogous manner to that described above, the carboxylic acid 17b-trans-βMe (91.8 mg, 0.272 mmol) gave the title β-ketoester (79 mg, 57%) as a colorless oil.

| ¹H NMR (200 MHz, CDCl₃): | | | |
|---|---|---|---|
| δ | 1.24 | CH₃ | d, J=6.99Hz |
|  | 3.08 | CHCH₃ | m |
|  | 3.65 | CH₂CO₂ | s |

| ¹H NMR (200 MHz, CDCl₃): -continued | | | |
|---|---|---|---|
|  | 3.88 | H₄ | dd, J=2.54, 5.71Hz |
|  | 4.50 | H₃ | dd, J=2.54, 7.62Hz |
|  | 5.18, 5.26 | 2 CH₂O | 2s |
|  | 5.62 | O₂CNH | broad d, J=7.6Hz |
|  | 6.16 | NH | bs |
|  | 7.5–8.3 | aromatic protons | m, 8H |

IR (CHCl₃): 3440 (NH), 1775 (β-lactam), 1730–1715cm⁻¹ (ketone, ester, carbamate) FAB-MS: M/e=515 (M+H)

EXAMPLE 60

(±)-3S-Azido-4R-(1-p-nitrobenzyloxycarbonyl-2-oxo-3R-butyl)-azetidin-2-one (18b-cis-βMe)

In a manner analogous to that described above, the carboxylic acid 10-cis-βMe (52.3 mg, 0.284 mmol) gave the title β-ketoester (49.0 mg, 47.8%) as an off-white solid.

| ¹H NMR (200 MHz, CDCl₃): | | | |
|---|---|---|---|
| δ | 1.24 | CH₃ | d, J=7.26Hz |
|  | 2.85 | CHCH₃ | m |
|  | 3.68 | CH₂CO₂ | s |
|  | 4.07 | H₄ | dd, J=5.08, 9.31Hz |
|  | 4.81 | H₃ | dd, J=5.08, 2.54Hz |
|  | 5.28 | CH₂O | s |
|  | 5.9 | NH | bs |
|  | 7.52, 8.22 | ArH | 2d, J=8Hz |

EXAMPLE 61

(±)-3S-Azido-4R-(1-p-nitrobenzyloxycarbonyl-2-oxo-3S-butyl)-azetidin-2-one (18b-cis-αMe)

In a manner analogous to that described above, the carboxylic acid 10-cis-αMe (54.1 mg, 0.294 mmol) gave the title β-ketoester (45.4 mg, 42.8%) as a light yellow oil.

| ¹H NMR (200 MHz, CDCl₃): | | | |
|---|---|---|---|
| δ | 1.21 | CH₃ | d, J=7.20Hz |
|  | 2.94 | CHCH₃ | m |
|  | 3.63 | CH₂CO₂ | s |
|  | 3.84 | H₄ | dd, J=5.07, 9.94Hz |
|  | 4.79 | H₃ | dd, J=5.07, 2.69Hz |
|  | 5.26 | CH₂O | s |
|  | 6.06 | NH | bs |
|  | 7.52, 8.24 | ArH | 2d, J=8Hz |

IR (CHCl₃): 3420 (NH), 2120 (azide), 1775 (β-lactam), 1745, 1710cm⁻¹ (β-ketoester)

EXAMPLE 62

(±)-4R-(1-diazo-1-p-nitrobenzyloxycarbonyl-2-oxo-3R-butyl)-3R-N-phthalimido-azetidin-2-one (19a-trans-βMe)

To a mixture of the β-ketoester 18a-trans-βMe (111 mg, 0.238 mmol) in 5 ml of acetonitrile was added a solution of dodecylbenzenesulfonyl azide in hexane (1.1M, 0.28 ml, 0.31 mmol) followed by triethylamine (0.050 ml, 0.36 mmol). The reaction mixture was initially homogenous, but after several minutes began to deposit a white precipitate. After stirring for 2 h at RT, the mixture was evaporated and separated by flash chromatography through 20 g of silica gel (3:1 CH$_2$Cl$_2$/EtOAc) to yield 104 mg (89%) of product as a white solid.

| $^1$H NMR (200 MHz, CDCl$_3$): | | |
|---|---|---|
| δ 1.28 | CH$_3$ | d, J=6.89Hz |
| 3.94 | CHCH$_3$ | m |
| 4.27 | H$_4$ | dd, J=2.7, 6.7Hz |
| 5.20 | H$_3$ | d, J=2.7Hz |
| 5.41 | CH$_2$O | s |
| 6.16 | NH | bs |
| 7.58, 8.29 | PNB aromatic | AB, J=8.8Hz |
| 7.7–7.9 | phthalimido | m |

EXAMPLE 63

(±)-4R-(1-diazo-1-p-nitrobenzyloxycarbonyl-2-oxo-3R-butyl)-3S-N-phthalimido-azetidin-2-one (19a-cis-βMe)

In a manner analogous to that described above, the β-ketoester 18a-cis-βMe (27.0 mg, 0.0581 mmol) gave the title compound (24.3 mg, 85.2%) as a white solid.

| $^1$H NMR (200 MHz, CDCl$_3$): | | |
|---|---|---|
| δ 1.22 | CH$_3$ | d, J=6.91Hz |
| 3.85 | CHCH$_3$ | m |
| 4.37 | B4 | dd, J=5.08, 10.09Hz |
| 4.97, 5.08 | CH$_2$O | Ab, J=13.05Hz |
| 5.43 | H$_3$ | dd, J=5.08, 1.63Hz |
| 6.22 | NH | bs |
| 7.4–8.3 | aromatic protons | m |

EXAMPLE 64

(±)-4R-(1-diazo-1-p-nitrobenzyloxycarbonyl-2-oxo-3S-butyl)-3S-N-phthalimido-azetidin-2-one (19a-cis-αMe)

In a manner analogous to that described above, except that tetrahydrofuran was used as co-solvent in the reaction, the β-ketoester 18a-cis-αMe (30.0 mg, 0.0645 mmol) gave the title compound (21.5 mg, 67.9%) as a colorless oil.

| $^1$H NMR (200 MHz, CDCl$_3$): | | |
|---|---|---|
| δ 0.969 | CH$_3$ | d, J=6.99 |
| 3.75 | CHCH$_3$ | m |
| 4.21 | H$_4$ | dd, J=5.22, 10.44Hz |
| 5.30 | CH$_2$O | s |
| 5.48 | H$_3$ | dd, J=5.22, 1.77Hz |
| 6.15 | NH | bs |
| 7.47, 8.20 | PNB aromatic | AB, J=8.75Hz |
| 7.7–7.9 | phthalimido | m |

EXAMPLE 65

(±)-4R-(1-diazo-1-p-nitrobenzyloxycarbonyl-2-oxo-3S-butyl)-3R-p-nitrobenzyloxycarbonylamino-azetidin-2-one (19c-trans-βMe)

In a manner analogous to that described above, the β-ketoester 18c-trans-βMe (74.0 mg, 0.144 mmol) gave the title compound (63.2 mg, 81.3%) as a colorless oil.

| $^1$H NMR (200 MHz, CDCl$_3$): | | |
|---|---|---|
| δ 1.20 | CH$_3$ | d, J=6.98Hz |
| 3.8–4.0 | H$_4$, CHCH$_3$ | m, 2H |
| 4.57 | H$_3$ | dd, J=2.54, 8.26Hz |
| 5.19, 5.35 | 2CH$_2$O | 2s |
| 5.54 | O$_2$CNH | broad d, J=8.26Hz |
| 6.13 | NH | bs |
| 7.5–8.3 | aromatic protons | m, 8H |

EXAMPLE 66

(±)-3S-Azido-4R-(1-diazo-1-p-nitrobenzyloxycarbonyl-2-oxo-3R-butyl)-azetidin-2-one (19b-cis-βMe)

In a manner analogous to that described above, the β-ketoester 18b-cis-βMe (4.8 mg, 0.013 mmol) gave the title compound (5.0 mg, 97%) as a colorless oil.

| $^1$H NMR (200 MHz, CDCl$_3$): | | |
|---|---|---|
| δ 1.22 | CH$_3$ | d, J=7.05 Bz |
| 3.64 | CHCH$_3$ | m |
| 4.18 | H$_4$ | dd, J=5.08, 9.10Hz |
| 4.79 | H$_3$ | dd, J=5.08, 2.33Hz |
| 5.38 | CH$_2$O | s |
| 5.95 | NH | s |
| 7.55, 8.26 | ArH | 2d, J=8.8Hz |

IR (CHCl$_3$): 3410 (NH), 2145 (diazo), 2120 (azide), 1775 (β-lactam), 1720 cm$^{-1}$ (ketone, ester) FAB-MS: M/e=388 (M+H)

EXAMPLE 67

(±)-3S-Azido-4R-(1-diazo-1-p-nitrobenzyloxycarbonyl-2-oxo-3S-butyl)-azetidin-2-one (19b-cis-αMe)

In a manner analogous to that described above, the β-ketoester 18b-cis-αMe (15.0 mg, 0.0416 mmol) gave the title compound (13.8 mg, 85.8%) as a white solid.

| $^1$H NMR (200 MHz, CDCl$_3$): | | |
|---|---|---|
| δ 1.18 | CH$_3$ | d, J=6.91Hz |
| 3.72 | CHCH$_3$ | m |
| 3.98 | H$_4$ | dd, J=5.08, 10.15Hz |
| 4.80 | H$_3$ | dd, J=5.08, 2.69Hz |
| 5.37 | CH$_2$O | s |
| 5.9 | NH | bs |
| 7.55, 8.26 | ArH | 2d, J=8.6Hz |

IR (CHCl$_3$): 3410 (NH) 2140 (diazo), 2120 (azide), 1775 (β-lactam), 1720 cm$^{-1}$ (ketone, ester) FAB-MS: M/e=388 (M+H)

EXAMPLE 68

(±)-p-Nitrobenzyl-(1S,3R,5R,6S)-1-methyl-6-N-phthalimide-2-oxo-carbapenem-3-carboxylate (20a-cis-αMe)

To a solution of the diazo-β-ketoester 19a-cis-αMe (6.5 mg, 0.013 mmol) in 0.5 ml of benzene was added a catalytic amount of rhodium (II) octanoate. The stirred reaction mixture was heated at 70° C. for 15 minutes and was then cooled to RT and evaporated to yield the title bicyclic β-ketoester (6.2 mg, 100% crude yield) as a colorless oil. This compound displayed low stability on silica gel and was thus used in subsequent reactions without purification.

| $^1$H NMR (200 MHz, CDCl$_3$): | | |
|---|---|---|
| δ 1.16 | CH$_3$ | d, J=7.62Hz |
| 2.82 | H1 | dq, J=7.62, 7.62Hz |
| 4.11 | H5 | dd, J=5.08, 7.62Hz |
| 5.01 | H3 | s |

| ¹H NMR (200 MHz, CDCl₃): | | |
|---|---|---|
| 5.2–5.4 | CH₂O | AB |
| 5.89 | H6 | d, J=5.08Hz |
| 7.56, 8.26 | PNB aromatic | 2d, J=8.89Hz |
| 7.8–8.0 | phthalimido | m |

IR (CHCl₃): 1790 (pthalimide), 1770 (β-lactam), 1740 (ester), 1720 cm⁻¹ (phthalimide, ketone) FAB-MS: M/e=463 (M⁺)

EXAMPLE 69

(±)-p-Nitrobenzyl-(1R,3R,5R,6S)-1-methyl-6-N-Phthalimido-2-oxo-carbapenam-3-carboxylate (20a-cis-βMe)

In a manner analogous to that described above, diazo-β-ketoester 19a-cis-βMe (4.8 mg, 0.0098 mmol) was cyclized in chloroform at 65° C. (50 min) to give the title bicyclic β-ketoester (4.6 mg, 100% crude yield) as an oil. This compound was contaminated with a small amount (approx. 15%) of a by-product but could not be purified due to its instability on silica gel.

| ¹H NMR (200 MHz, CDCl₃): | | |
|---|---|---|
| δ 1.08 | CH₃ | d, J=7.30Hz |
| 2.95 | H1 | m |
| 4.69 | H5 | dd, J=5.71, 10.79Hz |
| 5.05 | H3 | s |
| 5.3–5.4 | CH₂O | m |
| 5.80 | H6 | d, J=5.71Hz |
| 7.5–8.3 | ArH | m, 8H |

IR (CHCl₃): 1790 (phthalimide), 1770 (β-lactam), 1740–1720 cm⁻¹ (ester, phthalimide, ketone)

EXAMPLE 70

(±)-p-Nitrobenzyl-(1R,3R,5R,6R)-1-methyl-6-N-phthalimido-2-oxo-carbapenam-3-carboxylate (20a-trans-βMe)

In a manner analogous to that described above, the diazo-β-ketoester 19a-trans-βMe (6.5 mg, 0.013 mmol) was cyclized in ethyl acetate at 70° C. (30 min.) to give the title compound (6.2 mg, 100% crude yield) as a white solid.

| ¹H NMR (200 MHz, CDCl₃): | | |
|---|---|---|
| δ 1.41 | CH₃ | d, J=8.25Hz |
| 2.84 | H1 | dq, J=8.26, 8.25Hz |
| 4.57 | H5 | dd, J=3.18, 8.26Hz |
| 4.83 | H3 | s |
| 5.2–5.4 | CH₂O | AB |
| 5.43 | H6 | d, J=3.18Hz |
| 7.5–8.3 | ArH | m, 8H |

IR (CHCl₃): 1780 (phthalimide), 1770 (β-lactam), 1725 cm⁻¹ (phthalimide, ester, ketone)

EXAMPLE 71

(±)-p-Nitrobenzyl-(1R,3R,5R,6R)-1-methyl-6-p-nitrobenzyloxycarbonylamino-2-oxo-carbapenam-3-carboxylate (20c-trans-βMe)

In a manner analogous to that described above, the diazo-β-ketoester 19c-trans-βMe (11.0 mg, 0.0204 mmol) was cyclized in benzene at 60° C. for 10 minutes to give the title compound (10.7 mg, 100% crude yield) as an oil.

| ¹H NMR (200 MHz, CDCl₃): | | |
|---|---|---|
| δ 1.32 | CH₃ | d, J=8.25Hz |
| 2.82 | H1 | dq, J=8.25, 8.25Hz |
| 4.22 | H5 | dd, J=2.54, 8.25Hz |
| 4.75 | H3 | s |
| 5.01 | H6 | dd, J=2.54, 8.89Hz |
| 5.23 | NCO₂CH₂Ar | s |
| 5.24, 5.35 | CO₂CH₂Ar | 2d, J=13.9 |
| 5.76 | NH | broad d, J=8.9Hz |
| 7.45–8.3 | ArH | m, 8H |

IR (CHCl₃): 3440 (NH), 1780 (β-lactam), 1740–1720 cm⁻¹ (ester, carbamate, ketone)

EXAMPLE 72

(±)-p-Nitrobenzyl-(1S,3R,5R,6S)-6-azido-1-methyl-2-oxo-carbapenam-3-carboxylate (20b-cis-αMe)

In a manner analogous to that described above, the diazo-β-ketoester 19b-cis-αMe (2.2 mg, 0.0057 mmol) was cyclized in benzene at 50° C. (30 min) to give the title compound (2.0 mg, 100% crude yield) as an oil.

| ¹H NMR (200 MHz, CDCl₃): | | |
|---|---|---|
| δ 1.24 | CH₃ | d, J=6.84Hz |
| 2.65 | H1 | m |
| 3.9 | H5 | dd, J=5, 8Hz |
| 4.96 | H3 | s |
| 5.24 | H6 | d, J=5Hz |
| 5.2–5.4 | CO₂CH₂Ar | AB |
| 7.54, 8.24 | ArH | 2d, J=8Hz |

IR (CHCl₃): 2120 (azide), 1775 (β-lactam), 1740 cm⁻¹ (ester, ketone)

EXAMPLE 73

(±)-p-Nitrobenzyl-(1S,5R,6S)-1-methyl-2-phenylthio-6-phthalimido-carbapen-2-em-3-carboxylate (21a-cis-αMe, SR=phenylthio)

A solution of the crude bicyclic β-ketoester a-cis-αMe (3.3 mg, approx. 0.0071 mmol) in 0.3 ml of acetonitrile was cooled to −20° C. and diisopropylethylamine (0.010 ml, 0.057 mmol) and trifluoromethanesulfonic anhydride (0.0050 ml, 0.030 mmol) were added. After 10 min additional diisopropylethylamine (0.0050 ml, 0.029 mmol) was added followed by thiophenol (0.0030 ml, 0.029 mmol). The reaction mixture was allowed to warm to 0° during 20 min and was then diluted with ethyl ether and washed with pH 7 phosphate buffer and brine. Drying and evaporation gave a brown oil which was separated by preparative TLC on silica gel (1:1 EtOAc/hexane) to yield 1.0 mg (25%) of the title carbapenem as a colorless oil.

| ¹H NMR (200 MHz, CDCl₃): | | |
|---|---|---|
| δ 0.90 | CH₃ | d, J=6.91Hz |
| 3.33 | H1 | dq, J=7.12, 6.91Hz |
| 4.05 | H5 | dd, J=5.85, 7.12Hz |
| 5.35, 5.53 | CH₂O | 2d, J=13.7Hz |
| 5.79 | H6 | d, J=5.85Hz |
| 7.2–8.3 | ArH | m, 13H |

IR (CHCl₃): 1800 (β-lactam), 1780 (phthalimide), 1725 cm⁻¹ (phthalimide, ester)

EXAMPLE 74

(±)-p-Nitrobenzyl-(1S,5R,6S)-1-methyl-2-[2-(p-nitrobenzyloxycarbonylamino)ethylthio]-6-phthalimidocarbapen-2-em-3-carboxylate (21a-cis-αMe, SR=2-p-nitrobenzyloxycarbonylaminoethylthio)

In a manner analogous to that described above, except that N-p-nitrobenzyloxycarbonylcysteamine was used in place of thiophenol, the crude bicyclic β-ketoester 20a-cis-αMe (3.4 mg, approx. 0.0073 mmol) gave the title carbapenem (0.9 mg, 18%) as a colorless oil.

| $^1$H NMR (200 MHz, CDCl$_3$): | | | |
|---|---|---|---|
| δ | 1.29 | CH$_3$ | d, J=7.05Hz |
| | 2.9–3.6 | H1, SCH$_2$CH$_2$N | m, 5H |
| | 4.11 | H5 | dd, J=5.85, 7.27Hz |
| | 5.07 | NCO$_2$CH$_2$Ar | s |
| | 5.37, 5.49 | CO$_2$CH$_2$Ar | 2d, J=13.8Hz |
| | 5.7 | NH | bs |
| | 5.84 | H6 | d, J=5.85Hz |
| | 7.4–8.3 | ArH | m, 12H |

IR (CHCl$_3$): 3440 (NH), 1800 (β-lactam), 1780 (phthalimide) 1720cm$^{-1}$ (phthalimide, ester, carbamate) UV (CH$_3$CN): λmax=268, 310 nm FAB-MS: M/e=702 (M+H)

EXAMPLE 75

(±)-p-Nitrobenzyl-(1R,5R,6R)-1-methyl-2-[2-(p-nitrobenzyloxycarbonylamino)ethylthio]-6-phthalimidocarbapen-2-em-3-carboxylate (21a-trans-βMe, SR=2-p-nitrobenzyloxycarbonylaminoethylthio)

In a manner analogous to that described above, the crude bicyclic β-ketoester 20a-trans-βMe (6.5 mg, 0.0140 mmol) gave the title carbapenem (1.2 mg, 12%) as a colorless oil.

| $^1$H NMR (200 MHz, CDCl$_3$): | | | |
|---|---|---|---|
| δ | 1.44 | CH$_3$ | d, J=7.3Hz |
| | 2.8–3.6 | H1,SCH$_2$CH$_2$N | m, 5H |
| | 4.64 | H5 | dd, J=3.2, 9.5Hz |
| | 5.17 | NCO$_2$CH$_2$Ar | s |
| | 5.29, 5.52 | CO$_2$CH$_2$Ar | 2d, J=13.3Hz |
| | 5.47 | H6 | d, J=3.2Hz |
| | 7.5–8.4 | ArH | m, 12H |

IR (CHCl$_3$): 3470 (NH), 1795 (β-lactam), 1780 (phthalimide) 1730cm$^{-1}$ (ester, phthalimide, carbamate)

EXAMPLE 76

(±)-p-Nitrobenzyl-(1R,5R,6R)-1-methyl-2-phenylthio-6-N-phthalimido-carbapen-2-em-3-carboxylate (21a-trans-βMe, SR=phenylthio)

In a manner analogous to that described in Example 73, the crude bicyclic β-ketoester 20a-trans-βMe is converted to the title carbapenem.

EXAMPLE 77

(±)-p-Nitrobenzyl-(1R,5R,6R)-1-methyl-6-p-nitrobenzyloxycarbonylamino-2-phenylthio-carbapen-2-em-3-carboxylate (21c-trans-βMe, SR=phenylthio)

In a manner analogous to that described above, the crude bicyclic β-ketoester 20c-trans-βMe (7.7 mg, 0.015 mmol) gave the title carbapenem (0.5 mg, 6%) as an oil.

| $^1$H NMR (200 MHz, CDCl$_3$): | | | |
|---|---|---|---|
| δ | 1.07 | CH$_3$ | d, J=7.2Hz |
| | 3.1 | H1 | m |
| | 4.15 | H5 | dd, J=3, 10Hz |
| | 4.9 | H6 | dd, J=3, 8Hz |
| | 5.2–5.6 | NH,2 CO$_2$CH$_2$Ar | m, 5H |
| | 7.3–8.3 | ArH | m, 13H |

UV (CH$_3$CN): λmax=270, 320 nm

EXAMPLE 78

(±)-1-alloxalyl-4R-(1-t-butyldiphenylsilyloxy-2S-propyl)-3R-N-phthalimido-azetidin-2-one(22a-trans-αMe)

A solution of the azetidinone 4-trans-αMe (1.00 g, 1.95 mmol) in 10 ml of methylene chloride was cooled to −30° C. and pyridine (0.47 ml, 5.8 mmol) was added followed by allyloxyoxalyl chloride (0.850 g, 5.74 mmol). The solution was allowed to warm gradually to RT, and the progress of the reaction was monitored by TLC on silica gel. After 3.5 hours the reaction was complete and the solution was diluted with ethyl ether and washed with pH7 phosphate buffer and brine. Drying (MgSO$_4$) and evaporation gave 1.12 g (93%) of the oxalimide as a white foam. This compound was unstable towards chromatography on silica gel and was thus used directly in the next reaction without purification.

| $^1$H NMR (200 MHz, CDCl$_3$): | | | |
|---|---|---|---|
| δ | 0.82 | Sit-Bu | s |
| | 0.91 | CH$_3$ | d, J=6.98Hz |
| | 2.78 | CHCH$_3$ | m |
| | 3.5–3.75 | CH$_2$OSi | m |
| | 4.87 | OCH$_2$C=C | d, J=6.1Hz |
| | 4.99 | H4 | t, J=4.1Hz |
| | 5.3–5.5 | C=CH$_2$ | m |
| | 5.49 | H3 | d, J=4.1Hz |
| | 5.9–6.1 | CH=C | m |
| | 7.3–7.9 | ArH | m, 14H |

IR (CHCl$_3$): 1820, 1780, 1755, 1725, 1710 cm$^{-1}$

EXAMPLE 79

(±)-1-alloxalyl-4R-(1-t-butyldiphenylsilyloxy-2R-propyl)-3R-N-phthalimido-azetidin-2-one (22a-trans-βMe)

In a manner analogous to that described above, the azetidinone 4-trans-βMe (1.00 g, 1.95 mmol) gave the title compound (1.20 g, 98% crude) as a white foam.

| $^1$H NMR (300 MHz, CDCl$_3$): | | | |
|---|---|---|---|
| δ | 1.05 | Sit-Bu | s |
| | 1.14 | CH$_3$ | d, J=7.02Hz |
| | 2.40 | CHCH$_3$ | m |
| | 3.63 | CH$_A$OSi | dd, J=10.9, 3.42Hz |
| | 3.85 | CH$_B$OSi | dd, J=10.9, 3.18Hz |
| | 4.60 | H4 | dd, J=4.16, 5.18Hz |
| | 4.87 | OCH$_2$C=C | d, J=6.05Hz |
| | 5.3–5.5 | C=CH$_2$ | m |
| | 5.9–6.1 | CH=C | m |
| | 6.10 | H3 | d, J=4.16Hz |
| | 7.3–7.9 | ArH | m, 14H |

IR (CHCl$_3$): 1820, 1780, 1755, 1725, 1705 cm$^{-1}$

EXAMPLE 80

(±)-1-alloxalyl-4R-(1-t-butyldiphenylsilyloxy-2S-propyl)-3R-p-nitrobenzylcarbonylamino-azetidin-2-one (22b-trans-αMe)

In a manner analogous to that described above, the azetidinone 15b-trans-αMe (2.85 g, 5.08 mmol) gave the title oxalimide (3.4 g, 99% crude) as a yellow oil.

| $H^1$ NMR (200 MHz, CDCl$_3$): | | | |
|---|---|---|---|
| δ | 0.97 | CH$_3$ | d, J=6.42Hz |
| | 1.04 | Sit-Bu | s |
| | 1.71 | CHCH$_3$ | m |
| | 3.6–3.9 | CH$_2$OSi | m |
| | 4.7–4.9 | H4, OCH$_2$C=C | m, 3H |
| | 5.1–5.25 | OCH$_2$Ar | AB |
| | 5.3–5.55 | H3, C=CH$_2$ | m, 3H |
| | 5.9–6.1 | CH=C | m |
| | 7.3–8.25 | ArH | m, 14H |

IR (CHCl$_3$): 1810, 1755, 1730, 1710 cm$^{-1}$

EXAMPLE 81

(±)-1-alloxalyl-4R-(1-t-butyldiphenylsilyloxy-2R-propyl)-3R-p-nitrobenzylcarbonylamino-azetidin-2-one (22b-trans-βMe)

In a manner analogous to that described above, the azetidinone 15b-trans-βMe (1.68 g, 2.99 mmol) gave the title oxalimide (2.0 g, 99% crude) as a yellow foam.

| $^1$H NMR (200 MHz, CDCl$_3$): | | | |
|---|---|---|---|
| δ | 1.05 | Sit-Bu | s |
| | 1.10 | CH$_3$ | d, J=6.99Hz |
| | 2.35 | CHCH$_3$ | m |
| | 3.5–3.8 | CH$_2$OSi | m |
| | 4.40 | H4 | t, J=5.08Hz |
| | 4.83 | OCH$_2$C=C | d, J=5.47Hz |
| | 5.09 | H3 | dd, J=5.08, 7.7Hz |
| | 5.20 | OCH$_2$Ar | s |
| | 5.2–5.5 | NH, C=CH$_2$ | m, 3H |
| | 5.9–6.1 | CH=C | m |
| | 7.3–8.3 | ArH | m, 14H |

IR (CHCl$_3$): 3450, 1815, 1750, 1730, 1710 cm$^{-1}$

EXAMPLE 82

(±)-1-allyloxycarbonyltriphenylphosphoranylidene)-methyl-4R-(1-t-butylidiphenylsilyloxy-2S-propyl)-3R-N-phthalimido-azetidin-2-one (23a-trans-αMe)

Method A:

To a solution of the oxalimide 22a-trans-βMe (1.10 g, 1.76 mmol) in 10 ml of toluene was added triphenylphosphine (1.84 g, 7.05 mmol) and triethylphosphite (0.302 ml, 1.76 mmol). The reaction mixture was heated at 90° C. for 16 hours and was then cooled to RT and evaporated to give a dark oil. Flash chromatography through 50 g of silica gel (1:1 EtoAc/hexane) yielded 1.22 g (80%) of the title ylide as a white foam.

Method B:

To a solution of the azetidinone 4-trans-αMe (1.00 g, 1.95 mmol) in 10 ml of methylene chloride were added allyl glyoxylate (0.283 g, 2.14 mmol), triethylamine (0.27 ml, 1.9 mmol), and 1.0 g of powdered 3A molecular sieves. The mixture was vigorously stirred at RT for 17 hours and was then filtered and evaporated to give a brown foam. Flash chromatography through 75 g of silica gel (1:2:7 EtoAc/hexane/CH$_2$CH$_2$) gave 0.856 g of a white foam. This hemiaminal intermediate was dissolved in 20 ml of tetrahydrofuran, cooled to −30° C., and 2,6-lutidine (0.19 ml, 1.6 mmol) was added followed by thionyl chloride (0.12 ml, 1.6 mmol). After 40 minutes, the mixture was diluted with ethyl ether, filtered, and evaporated to give the α-chloro-ester intermediate as a yellow oil. This compound was dissolved in N,N-dimethylformamide (15 ml) and triphenylphosphine (0.394 g, 2.05 mmol) and 2,6-lutidine (0.175 ml, 1.50 mmol) were added. The reaction mixture was heated at 80° C. for 24 hours and was then cooled to RT, diluted with ethyl acetate, and washed successively with sat. NaHCO$_3$, water (2×) and brine. Drying (MgSO$_4$) and evaporation gave an oil Which was purified by flash chromatography through 50 g of silica gel (3:7 EtOAc/CH$_2$Cl$_2$) to yield 0.327 g (19.3% overall) of the ylide as a white foam.

IR (CHCl$_3$): 1780 (phthalimide), 1750 (β-lactam), 1720 (ester, phthalimide), 1610 cm$^{-1}$ (ylide) FAB-MS: M/e=871 (M+H)

EXAMPLE 83

(±)-1-allyloxycarbonyltriphenylphosphoranylidene)-methyl-4R-(1-t-butylidiphenylsilyloxy-2R-propyl)-3R-N-phthalimido-azetidin-2-one (23a-trans-βMe)

Method A:

Following Method A as described above, the oxalimide 22a-trans-βMe (1.20 g, 1.92 mmol) gave the above named ylide (1.39 g, 84%) as a yellow oil.

Method B:

Following Method B as described above, the azetidinone 4-trans-βMe (1.00 g, 1.95 mmol) gave the title ylide (0.110 g, 6.5%) as a light yellow foam.

IR (CHCl$_3$): 1780 (phthalimide), 1750 (β-lactam), 1720cm$^{-1}$ (ester, phthalimide) FAB-MS: M/e=871 (M+H)

EXAMPLE 84

(±)-1-allyloxycarbonyltriphenylphosphoranylidene)-methyl-4R-(1-t-butylidiphenylsilyloxy-2S-propyl)-3R-p-nitrobenzyloxycarbonylamino-azetidin-2-one (23b-trans-αMe)

Following Method A as described above, except that the triethylphosphite was added portionwise during 6 h, the crude oxalimide 22b-trans-αMe (3.4 g, 5.08 mmol) gave the title ylide (0.917 g, 19.7% as a yellow oil.

IR (CHCL$_3$): 3410 (NH), 1745 (β-lactam), 1720 (carbamate, ester), 1615 cm$^{-1}$ (ylide). FAB-MS: M/e=920 (M+H)

EXAMPLE 85

(±)-1-(allyloxycarbonyltriphenylphosphoranylidene)-methyl-4R-(1-t-butyldiphenylsilyloxy-2R-propyl)-3R-p-nitrobenzyloxycarbonylamino-azetidin-2-one (23b-trans-βMe)

Following Method A as described above, the crude oxalimide 22b-trans-βMe (2.0 g, 2.99 mmol) gave the title ylide (0.58 g, 22%) as a yellow foam.

IR (CHCl$_3$): 3410 (NH), 1750 (β-lactam), 1725 (carbamate, ester), 1610 cm$^{-1}$ (ylide). FAB-MS: M/e=920 (M+H)

EXAMPLE 86

(±)-1-(allyloxycarbonyltriphenylphosphoranylidene)-methyl-4R-(1-hydroxy-2S-propyl)-3R-N-phthalimido-azetidin-2-one (24a-trans-αMe)

To a solution of the silyl ether 23a-trans-αMe (0.337 g, 0.375 mmol) in 2 ml of tetrahydrofuran was added acetic acid (0.22 ml, 3.8 mmol) followed by a solution of tetrabutylammonium fluoride in tetrahydrofuran (1.0M, 1.13 ml, 1.13 mmol). The reaction mixture was heated at 50° C. for 48 hours and was then cooled to RT and evaporated in vacuo. The resulting oil was purified by flash chromatography through 25 g of silica gel (1:1 EtOAc/$CH_2Cl_2$) to yield 0.163 g (69%) of the title alcohol as a white foam.

IR ($CHCl_3$): 1780 (phthalimide), 1755 ($\beta$-lactam), 1715 (phthalimide, ester), 1615 $cm^{-1}$ (ylide). FAB-MS: M/e=633 (M+H)

EXAMPLE 87

(±)-1-(allyloxycarbonyltriphenylphosphoranylidene)-methyl-4R-(1-hydroxy-2R-propyl)-3R-N-phthalimido-azetidin-2-one (24a-trans-$\beta$Me)

In a manner analogous to that described above, the silyl ether 23a-trans-$\beta$Me (1.39 g, 1.60 mmol) gave the title alcohol (0.730 g, 74%) as a pale yellow foam.

IR ($CHCl_3$): 1780 (phthalimide), 1750 ($\beta$-lactam), 1720 (phthalimide, ester), 1615 $cm^{-1}$ (ylide). FAB-MS: M/e=633 (M+H)

EXAMPLE 88

(±)-1-(allyloxycarbonyltriphenylphosphoranylidene)-methyl-4R-(1-hydroxy-2S-propyl)-3R-p-nitrobenzyloxycarbonylamino-azetidin-2-one (24b-trans-αMe)

In an analogous manner to that described above, the silyl ether 23b-trans-αMe (0.917 g, 0.997 mmol) gave the above named alcohol (0.160 g, 20%) as a light yellow foam.

IR ($CHCl_3$): 3600–3200 (OH), 3420 (NH), 1755 ($\beta$-lactam), 1725 (ester, carbamate, phthalimide), 1615 $cm^{-1}$ (ylide). FAB-MS: M/e=682 (M+H)

EXAMPLE 89

(±)-1-(allyloxycarbonyltriphenylphosphoranylidene)-methyl-4R-(1-hydroxy-2R-propyl)-3R-p-nitrobenzyloxycarbonylamino-azetidin-2-one (24b-trans-$\beta$Me)

In a manner analogous to that described above, the silyl ether 23b-trans-$\beta$Me (0.580 g, 0.631 mmol) gave the title alcohol (0.248 g, 49%) as a white solid.

IR ($CHCl_3$): 3600–3200 (OH), 3430 (NH), 1755 ($\beta$-lactam), 1725 (carbamate, phthalimide ester), 1615 $cm^{-1}$ (ylide). FAB-MS: M/e=682 (M+H)

EXAMPLE 90

(±)-Allyl-(1R, 5R, 6R)-1-methyl-6-phthalimidocarbapen-2-em-3-carboxylate (25a-trans-αMe)

To a solution of the ylide 24a-trans-αMe (0.120 g, 0.189 mmol) in 2.25 ml of dimethylsulfoxide at RT was added 2.25 ml of acetic anhydride. After 16 hours the reaction mixture was heated to 50° C. for 2 hours and then cooled to RT and evaporated under high vacuum. The residual oil was purified by preparative TLC on silica gel (35:65 EtOAc/$CH_2Cl_2$) to yield 38.1 mg (57%) of the title carbapenem as a colorless oil.

| $^1$H NMR (200 MHz, $CDCl_3$): | | | |
|---|---|---|---|
| $\delta$ | 1.29 | $CH_3$ | d, J=7.3Hz |
| | 3.43 | H1 | m |
| | 4.19 | H5 | dd, J=3.49, 6.66Hz |
| | 4.76 | $OCH_2C\!=\!C$ | m |
| | 5.32 | H6 | d, J=3.49Hz |
| | 5.25–5.5 | $C\!=\!CH_2$ | m |
| | 5.9–6.1 | $CH\!=\!C$ | m |
| | 6.36 | H2 | d, J=2.54 |
| | 7.75–8.0 | ArH | m |

IR ($CHCl_3$): 1795 ($\beta$-lactam), 1780 (phthalimide), 1725 $cm^{-1}$ (phthalimide, ester) FAB-MS: M/e=353 (M+H)

EXAMPLE 91

(±)-Allyl-(1S, 5R, 6R)-1-methyl-6-phthalimidocarbapen-2-em-3-carboxylate (25a-trans-$\beta$Me)

In a manner analogous to that described above, the ylide 24a-trans-$\beta$Me (0.730 g, 1.16 mmol) was cyclized to give the title carbapenem (0.225 g, as a yellow oil.

| $^1$H NMR (200 MHz, $CDCl_3$): | | | |
|---|---|---|---|
| $\delta$ | 1.33 | $CH_3$ | d, J=7.69Hz |
| | 3.34 | H1 | m |
| | 4.71 | H5 | dd, J=3.78, 10.5Hz |
| | 4.6–4.9 | $OCH_2C\!=\!C$ | m |
| | 5.25–5.5 | $C\!=\!CH_2$ | m |
| | 5.50 | H6 | d, J=3.78Hz |
| | 5.9–6.1 | $CH\!=\!C$ | m |
| | 6.32 | H2 | d, J=2.54Hz |
| | 7.7–7.9 | ArH | m |

IR ($CHCl_3$): 1795 ($\beta$-lactam), 1780 (phthalimide), 1725 $cm^{-1}$ (phthalimide, ester) UV ($CH_3CN$): $\lambda$max=274 nm FAB-MS: M/e=353 (M+H)

EXAMPLE 92

(±)-Allyl-(1R, 5R, 6R)-1-methyl-6-(p-nitrobenzyloxycarbonylamino)-carbapen-2-em-3-carboxylate (25b-trans-αMe)

To a solution of the ylide 24-trans-αMe (0.140 g, 0.174 mmol) in 0.6 ml of dimethylsulfoxide was added 0.6 ml of acetic anhydride. After stirring at RT for 9 hours, the reaction mixture was diluted with ethyl ether and washed with sat. $NaHCO_3$, water (2×) and brine. Drying ($MgSO_4$) and evaporation gave an oil which was purified by flash chromatography through 10 g of silica gel (1:1 EtOAc/$CH_2Cl_2$) to yield 25 mg (37%) of the title carbapenem as a white foam.

| $^1$H NMR (200 MHz, $CDCl_3$): | | | |
|---|---|---|---|
| $\delta$ | 1.32 | $CH_3$ | d, J=7.3Hz |
| | 3.38 | H1 | m |
| | 3.81 | H5 | dd, J=3.2, 7.3Hz |
| | 4.73 | $OCH_2C\!=\!C$ | m |
| | 4.84 | H6 | dd, J=3.2, 8.3Hz |
| | 5.23 | $OCH_2Ar$ | s |
| | 5.2–5.5 | $C\!=\!CH_2$ | m |
| | 5.66 | NH | broad d, J=8.3Hz |
| | 5.8–6.05 | $CH\!=\!C$ | m |
| | 6.34 | H2 | d, J=1.91Hz |
| | 7.52, 8.23 | ArH | 2d, J=8.9Hz |

IR ($CHCl_3$): 3440 (NH), 1785 ($\beta$-lactam), 1730$cm^{-1}$ (carbamate, ester) FAB-MS: M/e=402 (M+H)

EXAMPLE 93

(±)-Allyl-(1S, 5R, 6R)-1-methyl-6-(p-nitrobenzyloxycarbonylamino)-carbapen-2-em-3-carboxylate (25b-trans-βMe)

In a manner analogous to that described above, the ylide 24b-trans-βMe (0.220 g, 0.273 mmol) was cyclized to give the title carbapenem (0.055 g, 51%) as a colorless oil.

| $^1$H NMR (300 MHz, CDCl$_3$): | | | |
|---|---|---|---|
| δ | 1.25 | CH$_3$ | d, J=7.15Hz |
| | 3.24 | H1 | m |
| | 4.27 | H5 | dd, J=3.54, 10.6Hz |
| | 4.69 | OCH$_2$C=C | m |
| | 5.02 | H6 | dd, J=3.54, 8.24Hz |
| | 5.15–5.3 | OCH$_2$Ar | AB |
| | 5.2–5.45 | C=CH$_2$ | m |
| | 5.65 | NH | d, J=8.24Hz |
| | 5.85–6.0 | CH=C | m |
| | 6.29 | H2 | d, J=2.87Hz |
| | 7.49, 8.19 | ArH | 2d, J=8.9Hz |

IR (CHCl$_3$): 3440 (NH), 1785 (β-lactam), 1725 cm$^{-1}$ (carbamate, ester) UV (CH$_3$CN): λmax=273 nm FAB-MS: M/e=402 (M+H)

EXAMPLE 94

(±)-4R-[1R-(phenylthiocarbonyl)ethyl]-3S-N-phthalimido-azetidin-2one (26a-cis-βMe, SR$^1$)

To a solution of the carboxylic acid 6-cis-βMe (50.0 mg, 0.173 mmol) in 1.5 ml of acetonitrile and 1.3 ml of DMF were added thiophenol (0.045 ml, 0.44 mmol), dimethylaminopyridine (5 mg, 0.04 mmol) and a solution of dicyclohexylcarbodiimide in acetonitrile (0.87M, 0.30 ml 0.26 mmol). The reaction was monitored by TLC (silica gel, 3:1 EtOAc/THF +0.5% HOAc) and after 3 hours additional thiophenol (0.015 ml, 0.15 mmol) and dicyclohexylcarbodiimide-acetonitrile (0.87M, 0.10 ml, 0.087 mmol) were added. After 5 hours the reaction was complete and the mixture was filtered and evaporated to leave a solid which was extracted with CH$_2$Cl$_2$ and filtered. Purification of the filtrate by preparative TLC on silica gel (two separations: first 7:3 EtOAc/hexane, then 1:1:1 EtOAc/hexane/CH$_2$Cl$_2$) yielded 47 mg (71%) of the title thioester as a white solid.

| $^1$H NMR (200 MHz, CDCl$_3$): | | | |
|---|---|---|---|
| δ | 1.37 | CH$_3$ | d, J=6.99Hz |
| | 3.2 | CHCH$_3$ | m |
| | 4.24 | H4 | dd, J=5.08, 9.95Hz |
| | 5.49 | H3 | dd, J=5.08, 1.45Hz |
| | 6.77 | NH | bs |
| | 6.85–7.4 | SPh | m |
| | 7.7–7.95 | phthalimido | m |

IR (CHCl$_3$): 3430 (NH), 1790 (phthalimido) 1775 (β-lactam) 1725 (phthalimido) 1700 cm$^{-1}$ (thioester) FAB-MS: M/e=381 (M+H)

EXAMPLE 95

(±)-4R-[1S-(phenylthio)carbonylethyl]-3S-N-phthalimido-azetidin-2-one (26a-cis-αMe, SR$^1$)

In a analogous manner to that described above, 50.0 mg (0.173 mmol) of acid 6-cis-αMe gave 29.2 mg (44%) of the title thioester as a white solid.

| $^1$H NMR (200 MHz, CDCl$_3$): | | | |
|---|---|---|---|
| δ | 1.16 | CH$_3$ | d, J=7.48Hz |
| | 3.2 | CHCH$_3$ | m |
| | 4.08 | H4 | dd, J=5.01, 10.48Hz |
| | 5.47 | H3 | dd, J=5.01, 1.7Hz |
| | 6.39 | NH | bs |
| | 7.35–7.45 | SPh | bs |
| | 7.75–7.95 | phthalimido | m |

IR (CHCl$_3$): 3430 (NH), 1785 (phthalimido) 1770 (β-lactam) 1730 (phthalimido) 1700 cm$^{-1}$ (thioester) FAB-MS: M/e=381 (M+H)

EXAMPLE 96

(±)-4R-[1S-(2-cyanoethylthio)carbonylethyl]-3S-N-phthalimido-azetidin-2-one (26a-cis-αMe,SR$^2$)

In a manner analogous to that described above, using 3-mercaptopropionitrile in place of thiophenol, 58 mg (0.20 mmol) of carboxylic acid 6-cis-αMe gave 40.0 mg (56%) of the title thioester as a white solid.

| $^1$H NMR (200 MHz, CDCl$_3$): | | | |
|---|---|---|---|
| δ | 1.03 | CH$_3$ | d, J=6.91Hz |
| | 2.68 | CH$_2$CN | t, J=6.7Hz |
| | 3.0–3.3 | CHCH$_3$, CH$_2$S | m, 3H |
| | 4.08 | H4 | dd, J=5.65, 10.52Hz |
| | 5.48 | H3 | dd, J=5.65, 1.73Hz |
| | 6.69 | NH | bs |
| | 7.7–7.9 | phthalimido | m |

IR (CHCl$_3$): 3420 (NH), 1785 (phthalimido) 1770 (β-lactam) 1725 (phthalimido) 1685 cm$^{-1}$ (thioester) FAB-MS: M/e=358 (M+H)

EXAMPLE 97

(±)-4R-[1R-(phenylthio)carbonylethyl]-3R-N-phthalimido-azetidin-2-one (26a-trans-βMe,SR$^1$)

In a manner analogous to that described above, carboxylic acid 6-trans-βMe (11.0 mg, 0.0382 mmol) yielded 9.6 mg (66%) of the title thioester as a colorless oil.

| $^1$H NMR (200 MHz, CDCl$_3$): | | | |
|---|---|---|---|
| δ | 1.41 | CH$_3$ | d, J=6.98Hz |
| | 3.1 | CCH$_3$ | m |
| | 4.32 | H4 | dd, J=2.85, 6.66Hz |
| | 5.29 | H3 | d, J=2.85Hz |
| | 6.23 | NH | bs |
| | 7.4 | SPh | bs |
| | 7.75–7.95 | phthalimido | m |

IR (CHCl$_3$): 3440 (NH), 1790 (phthalimido) 1775 (β-lactam) 1720 (phthalimido) 1695 cm$^{-1}$ (thioester) FAB-MS: M/e=381 (M+H)

EXAMPLE 98

(±)-4R-[1R-(2-cyanoethylthio)carbonylethyl]-3R-phthalimido-azetidin-2-one (26a-trans-βMe,SR$^2$)

In a manner analogous to that described above, but using 3-mercaptopropionitrile in place of thiophenol, the carboxylic acid 6-trans-βMe (21.0 mg, 0.0729 mmol) produced 18.0 mg (69%) of the title thioester as a white solid.

| $^1$H NMR (200 MHz, CDCl$_3$): | | |
|---|---|---|
| δ 1.36 | CH$_3$ | d, J=7.55Hz |
| 2.65 | CH$_2$CN | t, J=7.05Hz |
| 3.0–3.2 | CHCH$_3$, CH$_2$S | m, 3H |
| 4.23 | H4 | dd, J=2.90, 7.35Hz |
| 5.20 | H3 | d, J=2.90Hz |
| 6.52 | NH | bs |
| 7.75–7.95 | phthalimido | m |

IR (CHCl$_3$): 3420 (NH), 1790, 1720 (phthalimido) 1770 (β-lactam) 1685 cm$^{-1}$ (thioester) FAB-MS: M/e=358 (M+H)

EXAMPLE 99

(±)-4R-[1R-(2-(p-nitrobenzyloxycarbonylamino)ethylthio)carbonylethyl]-3R-phthalimido-azetidin-2-one (26a-trans-βMe,SR$^3$)

In a manner analogous to that described above, but using N-(p-nitrobenzyloxycarbonyl)cysteamine in place of thiophenol, the carboxylic acid 6-trans-βMe (19.2 mg, 0.0667 mmol) gave 20.3 mg (58%) of the title thioester as a colorless oil.

| $^1$H NMR (200 MHz, CDCl$_3$): | | |
|---|---|---|
| δ 1.35 | CH$_3$ | d, J=6.98Hz |
| 3.0–3.5 | CHCH$_3$, SCH$_2$CH$_2$N | m, 5H |
| 4.24 | H4 | dd, J=2.85, 7.61Hz |
| 5.18 | CH$_2$O | AB |
| 5.25 | H3 | d, J=2.85Hz |
| 5.6–5.7 | NHCO$_2$PNB | br t |
| 6.8 | NH | |
| 7.5–8.3 | aromatic protons | m, 8H |

IR (CHCl$_3$): 3420 (NH), 1785, 1720 (phthalimido) 1770 (β-lactam) 1720 (carbamate), 1680 cm$^{-1}$ (thioester) FAB-MS: M/e=527 (M+H)

EXAMPLE 100

(±)-4R-[1S-(phenylthio)carbonylethyl]-3R-phthalimido-azetidin-2-one (26a-trans-αMe,SR$^1$)

In a analogous manner to that described above, the carboxylic acid 6-trans-αMe (26.2 mg, 0.0910 mmol) yielded the title thioester (19.2 mg, 56%) as a white solid.

| $^1$H NMR (200 MHz, CDCl$_3$): | | |
|---|---|---|
| δ 1.37 | CH$_3$ | d, J=7.45Hz |
| 3.0 | CHCH$_3$ | m |
| 4.13 | H4 | dd, J=2.36, 9.49Hz |
| 5.06 | H3 | d, J=2.36Hz |
| 6.40 | NH | bs |
| 7.35–7.45 | SPh | m |
| 7.7–7.9 | phthalimido | m |

IR (CHCl$_3$): 3430 (NH), 1790, 1720 (phthalimido) 1775 (β-lactam) 1695 cm$^{-1}$ (thioester) FAB-MS: M/e=381 (M+H)

EXAMPLE 101

(±)-4R-[1R-(phenylthio)carbonylethyl]-3R-nitrobenzyloxycarbonylamino-azetidin-2-one (26c-trans-βMe, SR$^1$)

To a solution of the carboxylic acid 17b-trans-βMe (77.9 g, 0.231 mmol) in 2 ml of acetonitrile and 1 ml of tetrahydrofuran were added thiophenol (0.036 ml, 0.35 mmol), dimethylaminopyridine (3.0 mg, 0.024 mmol) and a solution of dicyclohexylcarbodiimide in acetonitrile (0.46M, 0.6 ml, 0.28 mmol). After stirring at RT for 16 hours the reaction mixture was filtered and evaporated to leave 167 mg of an oil. Flash chromatography through 17 g of silica gel (65:35 EtOAc/hexane) gave 77.1 mg of a white solid which was contaminated with a small amount of dicyclohexylurea. Further purification by preparative TLC on silica gel (2:2:1 EtOAc/CH$_2$Cl$_2$/hexane) yielded 69.5 mg (70.1%) of the title thioester as a white solid.

| $^1$H NMR (200 MNz, CDCl$_3$): | | |
|---|---|---|
| δ 1.36 | CH$_3$ | d, J=6.98 Hz |
| 3.1 | CHCH$_3$ | m |
| 3.93 | H4 | dd, J=2.65, 4.74 Hz |
| 4.60 | H3 | dd, J=2.65, 7.55 Hz |
| 5.2 | CO$_2$CH$_2$ | s |
| 5.56 | —O$_2$CNH | broad d, J=7.55 HzM |
| 6.13 | NH | bs |
| 7.4 | SPh | bs |
| 7.47, 8.18 | PNB aromatic | 2d, J=8.4 Hz |

EXAMPLE 102

(±)-3R-allyloxycarbonylamino-4R-[1R-(phenylthio)-carbonylethyl]-azetidin-2-one (26b-trans-βMe,SR$^1$)

In a analogous manner to that described above, the carboxylic acid 17a-trans-βMe (63.8 mg, 0.264 mmol) gave the above named thioester (59.9 mg, 68%) as a colorless oil.

| $^1$H NMR (200 MHz, CDCl$_3$): | | |
|---|---|---|
| δ 1.33 | CH$_3$ | d, J=6.98 Hz |
| 3.1 | CHCH$_3$ | m |
| 3.91 | H4 | dd, J=1.90, 5.08 Hz |
| 4.5–4.6 | H3, CH$_2$C=C | m, 3H |
| 5.15–5.35 | C=CH$_2$ | m |
| 5.63 | —O$_2$CNH | d, J=7.48 Hz |
| 6.40 | NH | s |
| 7.40 | SPh | bs |

EXAMPLE 103

(±)-4R-[1R-(2-cyanoethylthio)carbonylethyl]-3R-p-nitrobenzyloxycarbonylamino-azetidin-2-one (26c-trans-βMe,SR$^2$)

In a manner analogous to that described above, except that the water soluble 1-ethyl-3-(3-dimethylamino)propylcarbodiimide was used in place of dicyclohexylcarbodiimide, the carboxylic acid b-trans-βMe (64.5 mg, 0.191 mmol) was condensed with 3-mercaptopropionitrile to yield the title thioester. The use of the water soluble carbodiimide allowed the urea by product to be removed by an aqueous work-up and the crude product could be purified by a single chromatography. Thus the crude reaction mixture was diluted with ethyl acetate and washed successively with 1N HCl, sat. NaHCO$_3$ and brine. Drying (MgSO$_4$) and evaporation gave a white solid which was purified by flash chromatography through 6 g of silica gel, (10:7:3 CH$_2$Cl$_2$/EtOAc/THF) to yield 58.0 mg (75%) of the thioester as a white solid.

| $^1$H NMR (200 MHz, d$_6$-acetone): | | |
|---|---|---|
| δ 1.30 | CH$_3$ | d, J=6.98 Hz |
| 2.7–3.15 | —SCHCH$_2$CN | m |
| 3.1 | CHCH$_3$ | m |

-continued

| ¹H NMR (200 MHz, d₆-acetone): | | |
|---|---|---|
| 3.85 | H4 | dd, J=2.54, 7.62 Hz |
| 4.67 | H3 | dd, J=2.54, 8.89 Hz |
| 5.26 | CO₂CH₂ | s |
| 7.28 | CO₂NH | broad d, J=8.9 Hz |
| 7.56 | NH | bs |
| 7.66, 8.26 | aromatic | 2d, J=8.6 Hz |

IR (CHCl₃): 3430 (NH), 1780 (β-lactam) 1730 (carbamate), 1695 cm⁻¹ (thioester) FAB-MS: M/e=407 (M+H)

EXAMPLE 104

(±)-3R-allyloxycarbonylamino-4R-[1R-(2-cyanoethylthio)carbonylethyl]-azetidin-2-one (26b-trans-βMe, SR²)

In a analogous manner to that described above, the carboxylic acid 17a-trans-βMe (41.2 mg, 0.170 mmol) was condensed with 3-mercaptopropionitrile to give the title thioester (39 mg, 74%) as colorless oil.

| ¹H NMR (200 MHz, CDCl₃): | | |
|---|---|---|
| δ 1.28 | CH₃ | d, J=6.98 Hz |
| 2.67 | —CH₂CN | t, J=7.5 Hz |
| 2.9-3.3 | CHCH₃, —SCH₂— | m, 3H |
| 3.86 | H4 | dd, J=1.84, 6.74 Hz |
| 4.45-4.65 | H3, CH₂C=C | m, 3H |
| 5.15-5.40 | C=CH₂ | m |
| 5.8-6.0 | CH=C | m |
| 5.95 | —O₂CNH | d, J=7.93 Hz |
| 6.83 | NH | bs |

IR (CHCl₃): 3430 (NH), 1780 (β-lactam) 1725 (carbamate), 1695cm⁻¹ (thioester) FAB-MS: M/e=312 (M+H)

EXAMPLE 105

(±)-4R-[1R-(phenylthio)carbonylethyl]-3R-phenoxyacetamido-azetidin-2-one (26d-trans-βMe, SR¹)

In a manner analogous to that described above, the crude acid 17c-trans-βMe (33.5 mg, approximately 0.115 mmol) gave the above named thioester (10.3 mg, 23%) as a white solid.

| ¹H NMR (200 MHz, CDCl₃): | | |
|---|---|---|
| δ 1.37 | CH₃ | d, J=6.98 Hz |
| 3.2 | CHCH₃ | m |
| 3.97 | H4 | dd, J=2.08, 4.55 Hz |
| 4.50 | CH₂O | s |
| 4.84 | H3 | dd, J=2.08, 7.72 Hz |
| 6.24 | NH | |
| 6.85-7.45 | —O₂CNH, ArH | m, 11H |

IR (CHCl₃): 3430 (NH), 1775 (β-lactam) 1690 cm⁻¹ (amide, thioester) FAB-MS: M/e=385 (M+H)

EXAMPLE 106

(±)-4R-[1S-(phenylthio)carbonylethyl]-3R-p-nitrobenzyloxycarbonylamino-azetidin-2-one (26c-trans-αMe, SR¹)

In a manner analogous to that described above, the carboxylic acid 17b-trans-αMe (30.9 mg, 0.0917 mmol) was condensed with thiophenol using 1-ethyl-3-(3-dimethylamino)propylcarbodiimide, to give the title thioester (21.8 mg, 55%) as colorless oil.

| ¹H NMR (200 MHz, CDCl₃): | | |
|---|---|---|
| δ 1.41 | CH₃ | d, J=7.37 Hz |
| 2.9 | CHCH₃ | m |
| 3.69 | H4 | dd, J=2.15, 9.66 Hz |
| 4.54 | H3 | dd, J=2.15, 8.49 Hz |
| 5.18 | CO₂CH₂ | s |
| 5.98 | —O₂CNH | d, J=8.49 H |
| 6.49 | NH | bs |
| 7.3-7.45 | SPh | m |
| 7.45, 8.17 | PNB aromatic | 2d, J=8.88 Hz |

IR (CHCl₃): 3430 (NH), 1775 (β-lactam) 1730 (carbamate), 1695 cm⁻¹ (thioester) FAB-MS: M/e=430 (M+H)

EXAMPLE 107

(±)-4R-[1S-(phenylthio)carbonylethyl]-3S-p-nitrobenzyloxycarbonylamino-azetidin-2-one (26c-cis-αMe,SR¹)

In a manner analogous to that described above, the acid 17b-cis-αMe (57.0 mg, 0.169 mmol) gave-the title thioester (46.0 mg, 63.47%) as a colorless oil.

| ¹H NMR (200 MHz, CDCl₃): | | |
|---|---|---|
| δ 1.24 | CH₃ | d, J=6.92 |
| 2.9 | CHCH₃ | m |
| 3.90 | H4 | dd, J=4.74, 9.96 Hz |
| 5.1-5.3 | H3, —CO₂CH₂ | m, 3H |
| 6.08 | O₂CNH | d, J=9.0 Hz |
| 6.3 | NH | bs |
| 7.3-7.45 | SPh | m |
| 7.50, 8.21 | PNB aromatic | 2d, J=8.5 Hz |

IR (CHCl₃): 3420 (NH), 1775 (β-lactam) 1730 (carbamate), 1695cm⁻¹ (thioester) FAB-MS: M/e=430 (M+H)

EXAMPLE 108

(±)-4R-[1S-(2-cyanoethylthio)carbonylethyl]-3S-p-nitro-benzyloxycarbonylamino-azetidin-2-one (26c-cis-αMe, SR²)

In a manner analogous to that described above, the acid 17b-cis-αMe (58.0 mg, 0.172 mmol) was condensed with 3-mercaptopropionitrile to give the title compound (32.3 mg, 46.2%) as a colorless oil.

| ¹H NMR (200 MHz, CDCl₃): | | |
|---|---|---|
| δ 1.12 | CH₃ | d, J=7.02 Hz |
| 2.65-2.75 | CH₂CN | m |
| 2.9 | CHCH₃ | m |
| 2.0-2.4 | SCH₂ | m |
| 3.87 | H4 | dd, J=4.80, 10.34 Hz |
| 5.1-5.3 | H3, CO₂CH₂ | m, 3H |
| 6.49 | O₂CNH | d, J=9.28 Hz |
| 6.74 | NH | bs |
| 7.50, 8.19 | aromatic | 2d, J=9.0 Hz |

IR (CHCl₃): 3430 (NH), 1775 (β-lactam) 1730 (carbamate), 1695 cm⁻¹ (thioester) FAB-MS: M/e=407 (M+H)

EXAMPLE 109

(±)-1-alloxalyl-4R-[1S-(phenylthio)carbonylethyl]-3S-N-phthalimido-azetidin-2-one (27a-cis-αMe,SR¹)

A solution of the azetidinone 26a-cis-αMe,SR¹ (16.9 mg, 0.0444 mmol) in 0.5 ml of methylene chloride was cooled to 0° C. and pyridine (0.011 ml, 0.14 mmol) was added followed by allyloxyoxalyl chloride (19 mg, 0.13 mmol). The solution was allowed to warm gradually to RT, and the progress of the reaction was monitored by TLC on silica gel (1:1 EtOAc/hexane). After 2 hours, additional pyridine (0.011 ml, 0.14 mmol) and allyloxyoxalyl chloride (19 mg, 0.13 mmol) were added. After 3 hours more, the reaction was complete and the solution was diluted with ethyl ether and washed with pH 7 phosphate buffer and brine. Drying (MgSO$_4$) and evaporation gave 25 mg (>100% yield) of the title oxalimide as a pale yellow oil. This compound was unstable towards chromatography on silica gel and was thus used directly in the next reaction without purification.

| $^1$H NMR (200 MHz, CDCl$_3$): | | |
|---|---|---|
| δ 1.07 | CH$_3$ | d, J=7.16 Hz |
| 3.25 | CHCH$_3$ | m |
| 4.73 | H4 | dd, J=6.14, 10.55 Hz |
| 4.85 | CH$_2$C=C | m |
| 5.3–5.5 | C=CH$_2$ | m |
| 5.70 | H3 | d, J=6.14 Hz |
| 5.9–6.1 | CH=C | m |
| 7.3–7.5 | SPh | m |
| 7.8–8.0 | phthalimide | m |

IR (CHCl$_3$): 1820, 1785, 1755, 1720, 1700 cm$^{-1}$

EXAMPLE 110

(±)-1-alloxalyl-4R-[1S-(2-cyanoethylthio)carbonylethyl]-3S-N-phthalimido-azetidin-2-one (27a-cis-αMe,SR$^2$)

In an analogous manner to that described above, the thioester 26a-cis-αMe,SR$^2$ (20.3 mg, 0.0568 mmol) gave the title oxalimide (27.7 mg, >100% crude yield) as a white solid.

| $^1$H NMR (200 MHz, CDCl$_3$): | | |
|---|---|---|
| δ 1.03 | CH$_3$ | d, J=6.60 Hz |
| 2.5–3.3 | CHCH$_3$, SCH$_2$CH$_2$CN | m, 5H |
| 4.65 | H4 | dd, J=6.74, 10.48 Hz |
| 4.8–4.9 | CH$_2$C=C | m |
| 5.3–5.5 | C=CH$_2$ | m |
| 5.68 | H3 | d, J=6.74 Hz |
| 5.9–6.1 | CH=C | m |
| 7.75–7.95 | aromatic | m |

IR (CHCl$_3$): 1820, 1785, 1755, 1730, 1695 cm$^{-1}$

EXAMPLE 111

(±)-1-alloxalyl-4R-[1R-(phenylthio)carbonylethyl]-3R-N-phthalimido-azetidin-2-one (27a-trans-βMe,SR$^1$)

In a manner analogous to that described above, the thioester 26a-trans-βMe,SR$^1$ (12.6 mg, 0.0331 mmol) gave the title oxalimide (17.4 mg, >100% crude yield) as a pale yellow oil.

| $^1$H NMR (200 MHz, CDCl$_3$): | | |
|---|---|---|
| δ 1.40 | CH$_3$ | d, J=6.98 Hz |
| 3.74 | CHCH$_3$ | m |
| 4.59 | H4 | dd, J=4.13, 5.40 Hz |
| 4.8–4.9 | CH$_2$C=C | m |
| 5.3–5.5 | C=CH$_2$ | m |
| 5.95 | H3 | d, J=4.13 Hz |
| 7.43 | SPh | bs |
| 7.7–7.9 | phthalimide | m |

IR (CHCl$_3$): 1820, 1780, 1755, 1725, 1690 cm$^{-1}$

EXAMPLE 112

(±)-1-alloxalyl-4R-[1R-(2-cyanoethylthio)carbonylethyl]-3R-N-phthalimido-azetidin-2-one (27a-trans-βMe,SR$^2$)

In a manner analogous to that described above, the thioester 26a-trans-βMe,SR$^2$ (10.0 mg, 0.0280 mmol) provided the title oxalimide (12.4 mg, 94.4% crude yield) as a colorless oil.

| $^1$H NMR (200 MHz, CDCl$_3$): | | |
|---|---|---|
| δ 1.38 | CH$_3$ | d, J=7.43 Hz |
| 2.6–2.8 | CH$_2$CN | m |
| 3.0–3.3 | SCH$_2$ | m |
| 3.58 | CHCH$_3$ | dq, J=5.78, 7.43 Hz |
| 4.56 | H4 | dd, J=3.60, 5.78 Hz |
| 4.8–4.9 | CH$_2$C=C | m |
| 5.3–5.5 | C=CH$_2$ | m |
| 5.81 | H3 | d, J=3.60 Hz |
| 5.9–6.1 | CH=C | m |
| 7.7–7.9 | phthalimide | m |

IR (CHCl$_3$): 1820, 1780, 1755, 1725, 1710, 1690 cm$^{-1}$

EXAMPLE 113

(±)-1-Alloxalyl-4R-[1R-(2-(p-nitrobenzyloxycarbonylamino)ethylthio)-carbonylethyl]-3R-phthalimido-azetidin-2-one (27a-trans-βMe,SR$^3$)

In a manner analogous to that described above, except that diisopropylethylamine was used in place of pyridine, the thioester 26a-trans-βMe,SR$^3$ (8.3 mg, 0.016 mmol) gave the oxalimide (10.3 mg, >100% crude yield) as a colorless oil.

| $^1$H NMR (200 MHz, CDCl$_3$): | | |
|---|---|---|
| δ 1.40 | CH$_3$ | d, J=5.39 Hz |
| 2.8–3.45 | SCH$_2$CH$_2$N | m |
| 3.6 | CHCH$_3$ | m |
| 4.54 | H4 | t, J=4.0 Hz |
| 4.85 | OCH$_2$C=C | d, J=6.0 Hz |
| 5.21 | NCO$_2$CH$_2$ | s |
| 5.3–5.5 | C=CH$_2$ | m |
| 5.7 | NH | bs |
| 5.86 | H3 | d, J=4.0 Hz |
| 5.9–6.1 | CH=C | m |
| 7.5–8.3 | ArH | m, 8H |

EXAMPLE 114

(±)-1-alloxalyl-4R-[1S-(phenylthio)carbonylethyl]-3R-N-phthalimido-azetidin-2-one (27a-trans-αMe,SR$^1$)

In a manner analogous to that described above, the thioester 26a-trans-αMe,SR$^1$ (14.0 mg, 0.0368 mmol) gave the oxalimide (20.2 mg, >100% crude yield) as a colorless oil.

| $^1$H NMR (200 MHz, CDCl$_3$): | | |
|---|---|---|
| δ 1.46 | CH$_3$ | d, J=7.37 Hz |
| 3.66 | CHCH$_3$ | dq, J=5.11, 7.37 Hz |
| 4.7–4.9 | CH$_2$C=C | m |
| 4.92 | H4 | dd, J=3.98, 5.11 Hz |
| 5.3–5.5 | C=CH$_2$ | m |
| 5.45 | H3 | d, J=3.99 Hz |
| 5.9–6.1 | CH=C | m |
| 7.38 | SPh | bs |
| 7.7–7.9 | phthalimido | m |

IR (CHCl$_3$): 1820, 1780, 1750, 1720, 1700 cm$^{-1}$

EXAMPLE 113

(±)-1-alloxalyl-4R-[1R-(phenylthio)carbonylethyl]-3S-N-phthalimido-azetidin-2-one (27a-cis-βMe,SR¹)

In a manner analogous to that described above, the thioester 26a-cis-βMe,SR¹ (10.0 mg, 0.0263 mmol) gave the oxalimide (12.5 mg, 96.6% crude yield) as a white solid.

| ¹H NMR (200 MHz, CDCl₃): | | |
|---|---|---|
| δ 1.57 | CH₃ | d, J=6.95 Hz |
| 3.35 | CHCH₃ | m |
| 4.7–4.9 | H4, CH₂C=C | m, 3H |
| 5.3–5.5 | C=CH₂ | m |
| 5.67 | H3 | d, J=6.66 Hz |
| 5.9–6.1 | CH=C | m |
| 6.7–8.0 | aromatic | m, 9H |

IR (CHCl₃): 1820, 1785, 1750, 1730, 1705 cm⁻¹

EXAMPLE 116

(±)-1-alloxalyl-3R-allyloxycarbonylamino-4R-[1R-(phenylthio)carbonylethyl]-azetidin-2-one (27b-trans-βMe,SR¹)

A solution of the azetidinone 26b-trans-βMe,SR¹ (37.0 mg, 0.111 mmol) in 1.1 ml of methylene chloride was cooled to 0° C. and pyridine (0.027 ml, 0.35 mmol) was added followed by allyloxyoxalyl chloride (49 mg, 0.33 mmol). After 45 minutes, the solution was diluted with ethyl ether and washed with pH 7 phosphate buffer and bine. Drying (MgSO₄) and evaporation gave 48.6 mg (98.4%) of the title oxalimide as a colorless oil. This compound was unstable towards chromatography on silica gel and was thus used directly in the next reaction without purification.

| ¹H NMR (200 MHz, CDCl₃): | | |
|---|---|---|
| δ 1.38 | CH₃ | d, J=6.91 Hz |
| 3.7 | CHCH₃ | m |
| 4.47 | H4 | broad t, J=3.8 Hz |
| 4.57 | NCO₂CH₂ | d, J=5.72 Hz |
| 4.83 | CO₂CH₂ | d, J=5.99 Hz |
| 5.02 | H3 | dd, J=3.8, 8.0 Hz |
| 5.1–5.5 | NH, 2 C=CH₂ | m, 5H |
| 5.75–6.05 | 2 CH=C | m, 2H |
| 7.3–7.45 | SPh | m |

IR (CHCl₃): 3470 (NH), 1820, 1755, 1710, 1695 cm⁻¹

EXAMPLE 117

(±)-1-alloxalyl-3R-allyloxycarbonylamino-4R-[1R-(2-cyanoethylthio)carbonylethyl]-azetidin-2-one (27b-trans-βMe,SR²)

In a manner analogous to that described above, the thioester 26b-trans-βMe,SR² (19.7 mg, 0.0633 mmol) gave the title oxalimide (27.6 mg, >100% crude yield) as a colorless oil.

| ¹H NMR (200 MHz, CDCl₃): | | |
|---|---|---|
| δ 1.38 | CH₃ | d, J=6.99 Hz |
| 2.65 | CH₂CN | t, J = 6.8 Hz |
| 2.95–3.30 | SCH₂ | m |
| 3.52 | CHCH₃ | dq, J=4.2, 6.99 Hz |
| 4.45 | H4 | broad t, J=4.2 Hz |
| 4.57 | NCO₂CH₂ | d, J=5.75 Hz |
| 4.7–4.85 | CO₂CH₂ | m |
| 4.96 | H3 | dd, J=4.2, 8.9 Hz |
| 5.2–5.5 | 2 C=CH₂ | m, 4H |
| 5.65 | NH | broad d, J=8.9 Hz |
| 5.8–6.1 | 2 CH=C | m, 2H |

IR (CHCl₃): 3450 (NH), 1820, 1755, 1725, 1710, 1690 cm⁻¹

EXAMPLE 118

(±)-1-alloxalyl-3R-p-nitrobenzyloxycarbonylamino-4R-]1R-(phenylthio)carbonylethyl]-azetidin-2-one (27c-trans-βMe,SR¹)

In a manner analogous to that described above, the thioester 26c-trans-βMe,SR¹ (15.0 mg, 0.0349 mmol) gave the title oxalimide (21.5 mg, >100% crude yield) as a colorless oil.

| ¹H NMR (200 MHz, CDCl₃): | | |
|---|---|---|
| δ 1.39 | CH₃ | d, J=6.99 Hz |
| 3.70 | CHCH₃ | m |
| 4.46 | H4 | broad t, J=3,8 Hz |
| 4.82 | CH₂C=C | d, J=3.8, 8.0 Hz |
| 5.08 | H3 | dd, J=3.8, 8.0 Hz |
| 5.19 | NCO₂CH₂ | s |
| 5.2–5.5 | C=CH₂ | m |
| 5.59 | NH | broad d, J=8.0 Hz |
| 5.9–6.1 | CH=C | m |
| 7.3–8.3 | ArH | m, 9H |

IR (CHCl₃): 3450 (NH), 1820, 1750, 1730, 1710, 1690 cm⁻¹

EXAMPLE 119

(±)-1-alloxalyl-4R-[1R-(2-cyanoethylthio)carbonylethyl]-3R-p-nitrobenzyloxycarbonylamino-azetidin-2-one (27c-trans-βMe,SR²)

In a manner analogous to that described above, except that tetrahydrofuran was used as a co-solvent due to the low solubility of the starting material in methylene chloride, the thioester 26c-trans-βMe,SR² (26.3 mg, 0.0647 mmol) gave the title oxalimide (23.3 mg, 69.4% crude yield) as a yellow oil.

| ¹H NMR (200 MHz, CDCl₃): | | |
|---|---|---|
| δ 1.42 | CH₃ | d, J=7.20 Hz |
| 2.60–2.75 | CH₂CN | m |
| 2.95–3.35 | SCH₂ | m |
| 3.50 | CHCH₃ | dq, J=5.37, 7.2 Hz |
| 4.49 | H4 | dd, J=3.72, 5.37 Hz |
| 4.8–4.9 | CH₂C=C | m |
| 4.94 | H3 | dd, J=3.73, 7.64 Hz |
| 5.22 | NCO₂CH₂ | s |
| 5.2–5.5 | C=CH₂ | m |
| 5.82 | NH | d, J=7.64 Hz |
| 5.85–6.05 | CH=C | m |
| 7.49–8.22 | ArH | 2 s, J=7.9 Hz |

IR (CHCl₃): 3440 (NH), 1820, 1750, 1725, 1710, 1690 cm⁻¹

EXAMPLE 120

(±)-1-alloxalyl-3R-phenoxyacetamido-4R-[1R-(phenylthio)carbonylethyl]-azetidin,2-one (27d-trans-βMe,SR¹

In a manner analogous to that described above, the thioester 26d-trans-βMe,SR¹ (10.1 mg, 0.0263 mmol) gave the title oxalimide (13.9 mg, >100% crude yield) as a colorless oil.

| ¹H NMR (200 MHz, CDCl₃): | | |
|---|---|---|
| δ 1.36 | CH₃ | d, J=7.44 Hz |
| 3.71 | CHCH₃ | m |
| 4.4–4.6 | H4, CH₂OPh | m, 3H |
| 4.7–4.9 | OCH₂C=C | m |
| 5.22 | H3 | dd, J=4.13, 7.94 |
| 5.2–5.5 | C=CH₂ | m |
| 5.9–6.1 | CH=C | m |
| 6.8–7.5 | ArH | m, 10 H |
| 7.29 | NH | broad d, J=7.9 Hz |

IR (CHCl₃): 3430 (NH), 1820, 1750, 1700 cm⁻¹

EXAMPLE 121

(±)-1-alloxalyl-3R-p-nitrobenzyloxycarbonylamino-4R-]1S-(phenylthio)carbonylethyl]-azetidin-2-one(27c-trans-αMe,SR¹)

In a manner analogous to that described above, the thioester 26c-trans-αMe,SR¹ (10.6 mg, 0.0247 mmol) gave the title oxalimide (13.2 mg, 98.8% crude yield) as a colorless oil.

| ¹H NMR (200 MHz, CDCl₃): | | |
|---|---|---|
| δ 1.34 | CH₃ | d, J = 6.91 Hz |
| 3.7 | CHCH₃ | m |
| 4.6–4.85 | H4, OCH₂C=C | m, 3H |
| 5.19 | NCO₂CH₂ | s |
| 5.2–5.5 | H3, C=CH₂ | m, 3H |
| 5.54 | NH | broad d, J=6.6 Hz |
| 5.85–6.05 | CH=C | m |
| 7.3–8.2 | ArH | m, 9H |

IR (CHCl₃): 3450 (NH), 1820, 1755, 1725, 1705, 1695 cm⁻¹

EXAMPLE 122

(±)-1-alloxalyl-3S-p-nitrobenzyloxycarbonylamino-4R-]1S-(phenylthio)carbonylethyl]-azetidin-2-one(27c-cis-αMe,SR¹)

In an analogous manner to that described above, the thioester 26c-cis-αMe,SR¹ (14.6 mg, 0.0340 mmol) gave the oxalimide (18.0 mg, 97.8% crude yield) as a colorless oil.

| ¹H NMR (200 MHz, CDCl₃): | | |
|---|---|---|
| δ 1.73 | CH₃ | d, J=7.16 Hz |
| 3.16 | CHCH₃ | dq, J=2.12, 7.16 Hz |
| 4.51 | H4 | dd, J=6.95, 2.12 Hz |
| 4.75–4.9 | OCH₂C=C | m |
| 5.19 | NCO₂CH₂ | s |
| 5.3–5.5 | C=CH₂ | m |
| 5.53 | H3 | dd, J=6.95, 9.74 Hz |
| 5.9–6.05 | CH=C | m |
| 6.37 | NH | d, J=9.74 Hz |
| 7.3–8.25 | ArH | m, 9H |

IR (CHCl₃): 3400, 1820, 1750, 1725, 1710 cm⁻¹

EXAMPLE 123

(±)-1-alloxalyl-4R-[1S-(2-cyanoethylthio)carbonylethyl]-3S-p-nitrobenzyloxycarbonylamino-azetidin-2-one (27c-cis-αMe,SR²)

In an analogous manner to that described above, the thioester 26c-cis-αMe,SR² (11.1 mg, 0.0273 mmol) gave the title oxalimide (14.8 mg, >100% crude yield) as a colorless oil.

| ¹H NMR (200 MHz, CDCl₃): | | |
|---|---|---|
| δ 1.59 | CH₃ | d, J=7.30 Hz |
| 2.55–2.75 | CH₂CN | m |
| 3.0–3.2 | CHCH₃, SCH₂ | m, 3H |
| 4.45 | H4 | dd, J=3.66, 7.05 Hz |
| 4.75–4.85 | OCH₂C=C | m |
| 5.23 | NCO₂CH₂ | s |
| 5.3–5.5 | C=CH₂ | m |
| 5.51 | H3 | dd, J=3.66, 9.7 Hz |
| 5.9–6.05 | CH=C | m |
| 6.22 | NH | d, J=9.7 Hz |
| 7.51, 8.22 | ArH | 2 d, J=8.9 Hz |

IR (CHCl₃): 3420, 1820, 1755, 1725, 1715 cm⁻¹

EXAMPLE 124

(±)-Allyl-(1S, 5R, 6S)-1-methyl-2-phenylthio-6-phthalimido-carbapen-2-em-3-carboxyate (29a-cis-αMe,SR²

To a solution of the oxalimide 27a-cis-αMe, SR¹ (25 mg crude, approx. 0.0444 mmol) in 0.4 ml of toluene was added excess triethyl phosphite (0.076 ml, 0.44 mmol) and the reaction mixture was heated to 90° C. After 2.5 hours, the solution was cooled to RT and evaporated under high vacuum to give 29.3 mg of a yellow oil. Conversion to the phosphorane 28a was evident from the infrared spectrum which showed disappearance of the high energy oxalimide carbonyl stretch at 1820 cm⁻¹ and the appearance of a characteristic absorbance at 1620–1640 cm⁻¹. The phosphorane was dissolved in 1.5 ml of p-xylene, a crystal of hydroquinone was added, and the solution was heated to reflux (138° C.). The progress of the cyclization was monitored by TLC on silica gel (1:1 EtOAc/hexane) and the reaction was judged to be complete after 2 hours. After cooling to RT, the solution was evaporated to leave a yellow oil. Purification by preparative TLC on silica gel (1:1 EtOAc/hexane) yielded 12.9 mg (63.1%) of the title carbapenem as a white solid.

| ¹H NMR (200 MHz, CDCl₃): | | |
|---|---|---|
| δ 0.90 | CH₃ | d, J=6.98Hz |
| 3.31 | H1 | dq, J=6.74, 6.98Hz |
| 4.03 | H5 | dd, J=5.61, 6.74Hz |
| 4.7–4.9 | CH₂C=C | m |
| 5.2–5.6 | C=CH₂ | m |
| 5.76 | H6 | d, J=5.61Hz |
| 5.9–6.1 | CH=C | m |
| 7.2–7.6 | SPh | m |
| 7.75–7.95 | phthalimido | m |

IR (CHCl₃): 1800 (β-lactam), 1780 (phthalimide), 1725 cm⁻¹ (phthalimide, ester) UV (EtOH): λmax=325 nm (ε=9,780) FAB-MS: m/e=461 (M+H)

EXAMPLE 125

(±)-Allyl-(1S, 5R, 6S)-2-(2-cyanoethylthio)-1-methyl-6-phthalimido-carbapen-2-em-3-carboxylate 29a-cis-αMe,SR²)

In a manner analogous to that described above, 27.7 mg (approx. 0.0568 mmol) of crude oxalimide 27a-cis-αMe,SR² was cyclized to give 14.8 mg (59.6%) of the title carbapenem as a colorless oil.

| ¹H NMR (300 MHz, CDCl₃): | | |
|---|---|---|
| δ 1.28 | CH₃ | d, J=7.20Hz |
| 2.7–3.5 | H1, SCH₂CH₂CN | m, 5H |

-continued

| ¹H NMR (300 MHz, CDCl₃): | | |
|---|---|---|
| 4.10 | H5 | dd, J=6.10, 8.91Hz |
| 4.7–4.9 | CH₂C=C | m |
| 5.25–5.50 | C=CH₂ | m |
| 5.83 | H6 | d, J=6.10Hz |
| 5.95–6.10 | CH=C | m |
| 7.75–7.95 | aromatic | m |

IR (CHCl₃): 1805 (β-lactam), 1780 (phthalimide), 1725 cm⁻¹ (phthalimide, ester) UV (CH₃CN): ), λmax=306 nm (ε=7500)

EXAMPLE 126

(±)-Allyl-(1R, 5R, 6R)-1-methyl-2-phenylthio-6-N-phthalimido-carbapen-2-em-3-carboxylate (29a-trans-βMe,SR¹)

In a manner analogous to that described above, 17.4 mg (approx. 0.0331 mmol) of crude oxalimide 27a-trans-βMe,SR¹ was cyclized to give 9.2 mg (60.3%) of the title carbapenem as a colorless oil. The reaction times were 5 hours (90° C.) for phosphorane formation and 12 hours (138° C.) for cyclization.

| ¹H NMR (200 MHz, CDCl₃): | | |
|---|---|---|
| δ 1.14 | CH₃ | d, J=7.30Hz |
| 3.09 | H1 | dq, J=9.88, 7.30Hz |
| 4.55 | H5 | dd, J=3.14, 9.88Hz |
| 4.7–4.9 | CH₂C=C | m |
| 5.2–5.6 | C=CH₂ | m |
| 5.38 | H6 | d, J=3.14 |
| 5.9–6.1 | CH=C | m |
| 7.3–7.55 | SPh | m |
| 7.7–7.9 | phthalimido | m |

IR (CHCl₃): 1780 (phthalimide, β-lactam), 1720 cm⁻¹ (phthalimide, ester) UV (CH₃CN): λmax=322 nm (ε=12,700) FAB-MS: M/e=461 (M+H)

EXAMPLE 127

(±)-Allyl-(1R, 5R, 6R)-2-(2-cyanoethylthio)-1-methyl-6-phthalimido-carbapen-2-em-3-carboxylate (29α-trans-βMe,SR²):

In a manner analogous to that described above, 12.4 mg (0.0264 mmol) of crude oxalimide a-trans-βMe,SR² was cyclized to give 7.3 mg (63.2%) of the title carbapenem as a colorless oil. The reaction times were 2 hours (90° C.) for phosphorane formation and 9.5 hours (138° C.) for cyclization.

| ¹H NMR (200 MHz, CDCl₃): | | |
|---|---|---|
| δ 1.45 | CH₃ | d, J=7.17Hz |
| 2.6–2.8 | CH₂CN | m |
| 2.95–3.25 | SCH₂ | m |
| 3.41 | CHCH₃ | dq, J=9.91, 7.17Hz |
| 4.65 | H5 | dd, J=3.10, 9.91Hz |
| 4.7–4.9 | CH₂C=C | m |
| 5.2–5.6 | C=CH₂ | m |
| 5.45 | H6 | d, J=3.10Hz |
| 5.9–6.1 | CH=C | m |
| 7.7–7.9 | phthalimido | m |

IR (CHCl₃): 1785 (phthalimido, β-lactam), 1725 cm⁻¹ (phthalimido, ester) UV (CH₃CN): λmax=313 nm (ε=9750) FAB-MS: M/e=438 (M+H)

EXAMPLE 128

(±)-Allyl-(1R, 5R, 6R)-1-methyl-2-[p-nitrobenzyloxycarbonylamino)ethylthio]-6-phthalimido-carbapen-2-em-3-carboxylate (29a-trans-βMe,SR³)

In a manner analogous to that described above, 10.3 mg (approx. 0.016 mmol) of crude oxalimide 27a-trans-βMe,SR³ was cyclized to give 1.7 mg (18%) of the title carbapenem as a colorless oil. The reaction times were 7.5 hours (90° C.) for cyclization.

| ¹H NMR (200 MHz, CDCl₃): | | |
|---|---|---|
| δ 1.47 | CH₃ | d, J=7.3Hz |
| 2.8–3.6 | H1, SCH₂CH₂N | m, 5H |
| 4.64 | H5 | dd, J=3.2, 9.5Hz |
| 4.7–4.9 | OCH₂C=C | m |
| 5.18 | NCO₂CH₂ | s |
| 5.2–5.6 | C=CH₂ | m |
| 5.43 | H6 | d, J=3.2Hz |
| 5.9–6.1 | CH=C | m |
| 7.7,8.2 | PNB aromatic | 2 d, J=8.9Hz |
| 7.75–8.0 | phthalimido | m |

IR (CHCl₃): 3460 (NH), 1780 (β-lactam), 1725 cm⁻¹ (ester, carbamate)

EXAMPLE 129

(±)-Allyl-(1S, 5R, 6R)-1-methyl-2-phenylthio-6-N-phthalimido-carbapen-2-em-3-carboxylate (29a-trans-αMe,SR¹)

In a manner analogous to that described above, 20.2 mg (approx. 0.0368 mmol) of crude oxalimide 27a-trans-αMe,SR¹ was cyclized to give 5.3 mg (29.2%) of the title carbapenem as a colorless oil. The reaction times were 2.5 hours (90° C.) for phosphorane formation and 1 hour (120° C.) for cyclization.

| ¹H NMR (200 MHz, CDCl₃): | | |
|---|---|---|
| δ 0.94 | CH₃ | d, J=6.94Hz |
| 3.40 | H1 | dq, J=6.38, 6.94Hz |
| 4.10 | H5 | dd, J=3.46, 6.38Hz |
| 4.7–4.9 | CH₂C=C | m |
| 5.2–5.6 | C=CH₂ | m |
| 5.29 | H6 | d, J=3.46Hz |
| 5.9–6.1 | CH=C | m |
| 7.35–7.55 | SPh | m |
| 7.7–7.9 | phthalimido | m |

IR (CHCl₃): 1795 (β-lactam), 1780 (phthalimide), 1725 cm⁻¹ (phthalimide, ester) UV (EtOH): λmax=326 nm (ε=9,980) FAB-MS: M/e=461 (M+H)

EXAMPLE 130

(±)-Allyl-(1R, 5R, 6R)-6-allyloxycarbonylamino-1-methyl-2-phenylthio-carbapen-2-em-3-carboxylate (29b-trans-βMe,SR¹)

To a solution of the crude oxalimide 27b-trans-βMe,SR¹ (48.6 mg, 0.109 mmol) in 0.9 ml of toluene was added excess triethyl phosphite (0.190 ml, 1.11 mmol) and the reaction mixture was heated to 90° C. After 3 hours, the solution was cooled to RT and evaporated under high vacuum to give 63.3 mg of a yellow oil. Conversion to the phosphorane 28b was evident from the infrared spectrum which showed disappearance of the high energy oxalimide carbonyl stretch at 1820 cm⁻¹ and the appearance of a characteristic absorbance at 1620–1640 cm$^{-1}$. The phosphorane was dissolved in 3 ml of p-xylene along with a crystal of hydroquinone, and the solution was heated to reflux (138° C.). The progress of the cyclization was monitored by TLC on silica gel (1:1 EtOAc/hexane) and the reaction was judged to be complete after 4 hours. After cooling to RT, the solution was evaporated to leave a yellow oil. Separation by flash chromatography on 5 g of silica gel (3:7 EtOAc/hexane) gave 10.0 mg (22.2%) of the title carbapenem as a colorless oil.

| $^1$H NMR (200 MHz, CDCl$_3$): | | |
|---|---|---|
| δ 1.06 | CH$_3$ | d, J=7.30Hz |
| 3.09 | H1 | dq, J=9.46, 7.30Hz |
| 4.09 | H5 | dd, J=2.44, 9.46Hz |
| 4.54 | NCO$_2$CH$_2$ | d, J=5.8Hz |
| 4.65–4.95 | CO$_2$CH$_2$ | m |
| 4.92 | H6 | dd, J=2.44, 8.0Hz |
| 5.1–5.5 | NH, 2 C=CH$_2$ | m, 5H |
| 5.75–6.1 | 2 CH=C | m, 2H |
| 7.3–7.5 | SPh | m |

IR (CHCl$_3$): 3440 (NH), 1780 (β-lactam), 1720 cm$^{-1}$ (ester, carbamate) UV (EtOH): λmax=321 FAB-MS: M/e=415 (M+H), 273 (M−OCCNHCO$_2$C$_3$H$_5$)

EXAMPLE 131

(±)-Allyl-(1R, 5R, 6R)-6-allyloxycarbonylamino-2-(2-cyanoethylthio)-1-methyl-carbapen-2-em-3-carboxylate (29b-trans-βMe,SR$^2$)

To a manner analogous to that described above, 27.6 mg (approx. 0.0633 mmol) of crude oxalimide 27b-trans-βMe,SR$^2$ was cyclized to give 3.0 mg (12.1%) of the title carbapenem as a pale yellow oil. The reaction times were 1.5 hours (90° C.) for phosphorane formation and 6 hours (138° C.) for cyclization.

| $^1$H NMR (200 MHz, CDCl$_3$): | | |
|---|---|---|
| δ 1.38 | CH$_3$ | d, J=7.83Hz |
| 2.6–2.8 | CH$_2$CN | m |
| 2.9–3.3 | SCH$_2$ | m |
| 3.43 | H1 | dq, J=9.48, 7.83Hz |
| 4.22 | H5 | dd, J=2.39, 9.48Hz |
| 4.60 | NCO$_2$CH$_2$ | d, J=5.7Hz |
| 4.6–4.9 | CO$_2$CH$_2$ | m |
| 5.02 | H6 | broad d, J=8Hz |
| 5.2–5.5 | NH, 2 C=CH$_2$ | m, 5H |
| 5.8–6.05 | 2 CH=C | m, 2H |

IR (CHCl$_3$): 3440 (NH), 1780 (β-lactam), 1720 cm$^{-1}$ (ester, carbamate) UV (EtOH): λmax=315 nm (ε=7,400) FAB-MS: M/e=392 (M+H)

EXAMPLE 132

(±)-Allyl-(1R, 5R, 6R)-1-methyl-6-p-nitrobenzyloxycarbonylamino-2-phenylthio-carbapen-2-em-3-carboxylate (29c-trans-βMe,SR$^1$)

To a manner analogous to that described above, 21.5 mg (approx. 0.0349 mmol) of crude oxalimide 27c-trans-βMe,SR$^1$ was cyclized to give 3.2 mg (18%) of the title carbapenem as a light yellow oil. The reaction times were 1.5 hours (90° C.) for phosphorane formation and 4 hours (138° C.) for cyclization.

| $^1$NMR (300 MHz, CDCl$_3$): | | |
|---|---|---|
| δ 1.07 | CH$_3$ | d, J=6.96Hz |
| 3.10 | H1 | m |
| 4.11 | H5 | dd, J=2.9, 10.2Hz |
| 4.65–4.95 | CH$_2$C=C | m |
| 4.93 | H6 | dd, J=2.9, 8.3Hz |
| 5.18 | NCO$_2$CH$_2$ | s |
| 5.2–5.6 | NH, C=CH$_2$ | m, 3H |
| 5.9–6.1 | CH=C | m |
| 7.3–8.3 | ArH | m, 9H |

IR (CHCl$_3$): 3440 (NH), 1780 (β-lactam), 1725 cm$^{-1}$ (ester, carbamate) UV (EtOH): λmax=322 nm (ε=7,550) FAB-MS: M/e=510 (M+H), 274 (M+H−OCCNHCO$_2$PNB)

EXAMPLE 133

(±)-Allyl-(1R, 5R, 6R)-2-(2-cyanoethylthio)-1-methyl-6-p-nitrobenzyloxycarbonylamino-carbapen-2-em-3-carboxylate (29c-trans-βMe,SR$^2$)

To a manner analogous to that described above, 23.3 mg (0.0449 mmol) of crude oxalimide 27c-trans-βMe,SR$^2$ was cyclized to give 1.5 mg (6.9%) of the title carbapenem as a pale yellow oil. The reaction times were 2 hours (90° C.) for phosphorane formation and 8 hours (138° C.) for cyclization.

| $^1$H NMR (300 MHz, CDCl$_3$): | | |
|---|---|---|
| δ 1.39 | CH$_3$ | d, J=7.02Hz |
| 2.6–2.8 | CH$_2$CN | m |
| 2.95–3.25 | SCH$_2$ | m |
| 3.45 | H1 | m |
| 4.25 | H5 | dd, J=2.8, 10.0Hz |
| 4.6–4.9 | OCH$_2$C=C | m |
| 5.04 | H6 | dd, J=2.8, 8.2Hz |
| 5.23 | NCO$_2$CH$_2$ | s |
| 5.2–5.6 | NH, C=CH$_2$ | m, 3H |
| 5.9–6.1 | CR=C | m |
| 7.52,8.24 | ArH | 2 d, J=9.0Hz |

IR (CHCl$_3$): 3440 (NH), 1780 (β-lactam), 1725 cm$^{-1}$ (ester, carbamate) UV (CH$_3$CN): λmax=267,315 nm (ε=5,000)

EXAMPLE 134

(±)-Allyl-(1R, 5R, 6R)-1-methyl-6-phenoxyacetamido-2-phenylthio-carbapen-2-em-3-carboxylate (29d-trans-βMe,SR$^1$)

To a manner analogous to that described above, 13.9 mg (approx. 0.0263 mmol) of crude oxalimide 27d-trans-βMe,SR$^1$ was cyclized to give 1.0 mg (8.2%) of the title amidocarbapenem as a colorless oil. The reaction times were 1.5 hours (90° C.) for phosphorane formation and 3 hours (138° C.) for cyclization.

| $^1$H NMR (200 MHz, CDCl$_3$): | | |
|---|---|---|
| δ 1.12 | CH$_3$ | d, J=7.90Hz |
| 3.11 | H1 | dq, J=9.60, 7.90Hz |
| 4.07 | H5 | dd, J=2.61, 9.60Hz |
| 4.46 | CH$_2$OPh | s |
| 4.65–4.95 | OCH$_2$C=C | m |
| 5.2–5.6 | H6, C=CH$_2$ | m, 3H |
| 5.9–6.1 | CH=C | m |
| 6.8–7.5 | NH, ArH | M, 11H |

IR (CHCl$_3$): 3430 (NH), 1780 ($\beta$-lactam), 1715 (ester), 1690 cm$^{-1}$ (amide) UV (EtOH): $\lambda$max=321 nm ($\epsilon$=5,900) FAB-MS: M/e=465 (M+H), 274 (M+H−OCCNHCOCH$_2$OPh)

EXAMPLE 135

($\pm$)-Potassium-(1S, 5R, 6S)-1-methyl-2-phenylthio-6-N-phthalimido-carbapen-2-em-3-carboxylate (30a-cis-$\alpha$Me,SR$^1$)

To a solution of the carbapenem 29a-cis-$\alpha$Me,SR$^1$ (10.4 mg, 0.0226 mmol) in ethyl acetate (0.3 mol)-methylene chloride (0.2 ml) at 0° C. were added in sequence a solution of triphenylphosphine in ethyl acetate (0.2M, 0.034 ml, 0.0068 mmol), a solution of potassium 2-ethylhexanoate in ethyl acetate (0.50M, 0.050 ml, 0.025 mmol) and a solution of tetrakis(triphenylphosphine)palladium in methylene chloride (0.05M, 0.045 ml, 0.0023 mmol). A tan precipitate began depositing almost immediately, and after 30 minutes, the reaction mixture was evaporated to dryness ill vacuo. The residue was partioned between ethyl ether and water and the aqueous phase was separated by reverse phase preparative TLC at 0° C. (elution with 3:1 H$_2$O/THF) to yield, after lyophilization, 3.2 mg (31%) of the title carbapenem as a pale yellow solid.

Method B:

A solution of the carbapenem 21a-cis-$\alpha$Me and potassium bicarbonate (1 eq) in tetrahydrofuran-ethanol-water (1:1:1) is hydrogenated at 1 atm. over 10% palladium on carbon (1 wt. eq.). After 3 hours the mixture is filtered through Celite and partitioned between ethyl acetate and water. The aqueous phase is lyophilized to give the crude product which is purified as described above to give the title carbapenem.

| $^1$H NMR (200 MHz, D$_2$O): | | |
|---|---|---|
| $\delta$ 0.92 | CH$_3$ | d, J=6.60Hz |
| 3.1–3.3 | H1 | m |
| 4.20 | H5 | dd, J=5.8, 5.8Hz |
| 5.94 | H6 | d, J=5.8Hz |
| 7.3–8.1 | ArH | m, 9H |

UV (H$_2$O): $\lambda$max=305 nm ($\epsilon$=6,600)

EXAMPLE 136

($\pm$)-Potassium-(1S, 5R, 6R)-1-methyl-2-phenylthio-6-N-phthalimido-carbapen-2-em-3-carboxylate (30a-trans-$\alpha$Me,SR$^1$)

In a manner analogous to that described above, the carbapenem 29a-trans-$\alpha$Me,SR$^1$ (5.5 mg, 0.012 mmol) gave the title compound (1.8 mg, 33%) as a pale yellow lyophilized solid.

| $^1$H NMR (300 MHz, D$_2$O): | | |
|---|---|---|
| $\delta$ 1.00 | CH$_3$ | d, J=7.39Hz |
| 3.57 | H1 | dq, J=6.47, 7.39Hz |
| 4.21 | H5 | dd, J=3.42, 6.47Hz |
| 5.60 | H6 | d, J=3.42Hz |
| 7.4–8.0 | ArH | m, 9H |

UV (H$_2$O): $\lambda$max=305 nm ($\epsilon$=9,270)

EXAMPLE 137

($\pm$)-Potassium-(1R, 5R, 6R)-1-methyl-2-phenylthio-6-N-phthalimido-carbapen-2-em-3-carboxylate (30a-trans-$\beta$Me,SR$^1$)

Method A:

In a manner analogous to that described above, the carbapenem 29a-trans-$\beta$Me,SR$^1$ (1.9 mg, 0.0041 mmol) gave the title compound (1.1 mg, 58%) as an off-white lyophilized solid.

Method B:

A solution of the carbapenem 21a-trans-$\beta$Me and potassium bicarbonate (1 eq.) in tetrahydrofuran-ethanol-water (1:1:1) is hydrogenated at 1 atm. over 10% palladium on carbon (1 weight equiv.). After 3 hours the mixture is filtered through Celite and partitioned between ethyl acetate and water. The aqueous phase is lyophilized to give the crude product which is purified as described above to give the title carbapenem.

| $^1$H NMR (200 MHz, D$_2$O): | | |
|---|---|---|
| $\delta$ 1.21 | CH$_3$ | d, J=7.23Hz |
| 3.2 | H1 | m |
| 4.60 | H5 | dd, J=3.3, 9.4Hz |
| 5.57 | H6 | d, J=3.3Hz |
| 7.5–8.0 | ArH | m, 9H |

UV (H$_2$O): $\lambda$max=306 nm ($\epsilon$=9,800)

EXAMPLE 138

($\pm$)-Potassium-(1S, 5R, 6S)-2-(cyanoethylthio)-1-methyl-6-N-phthalimido-carbapen-2-em-3-carboxylate (30a-cis-$\alpha$Me,SR$^2$)

In a manner analogous to that described above, the carbapenem 29a-cis-$\alpha$Me,SR$^2$ (14.6 mg, 0.0333 mmol) gave the title compound (9.0 mg, 62%) as an off-white lyophilized solid.

| $^1$H NMR (300 MHz, D$_2$O): | | |
|---|---|---|
| $\delta$ 1.23 | CH$_3$ | d, J=7.32Hz |
| 2.7–3.2 | SCH$_2$CH$_2$CN | m |
| 3.33 | H1 | dq, J=8.0, 7.32Hz |
| 4.18 | H5 | dd, J=5.4, 8.0Hz |
| 5.91 | H6 | d, J=5.4Hz |
| 7.8–8.0 | aromatic | m |

UV (H$_2$O): $\lambda$max=299 nm ($\epsilon$=6,300)

EXAMPLE 139

($\pm$)-Potassium-(1R, 5R, 6R)-2-(cyanoethylthio)-1-methyl-6-N-phthalimido-carbapen-2-em-3-carboxylate (30a-cis-$\beta$Me,SR$^2$)

In a manner analogous to that described above, the carbapenem 29a-trans-$\beta$Me,SR$^2$ (5.0 mg, 0.011 mmol) gave the title compound (3.4 mg, 71%) as an off-white lyophilized solid.

| $^1$H NMR (300 MHz, D$_2$O): | | |
|---|---|---|
| $\delta$ 1.42 | CH$_3$ | d, J=7.32Hz |
| 2.8–2.9 | CH$_2$CN | m |
| 2.9–3.65 | SCH$_2$ | m |
| 3.25 | H1 | m |
| 4.64 | H5 | dd, J=2.2, 8.9Hz |
| 5.58 | H6 | d, J=2.2Hz |
| 7.8–8.0 | ArH | m |

UV (H$_2$O): $\lambda$max=300 nm($\epsilon$=11,300)

EXAMPLE 140

(±)-Potassium-(1R, 5R, 6R)-1-methyl-6-p-nitrobenzyloxycarbonylamino-2-phenylthio-carbapen-2-em-3-carboxylate (30c-trans-βMe-SR¹)

In a manner analogous to that described above, the carbapenem 29c-trans-βMe,SR¹ (3.0 mg, 0.0059 mmol) gave the title compound (0.6 mg, 20%) as an off-white lyophilized solid.

| ¹H NMR (300 MHz, D₂O): | | |
|---|---|---|
| δ 1.07 | CH₃ | d, J=6.6Hz |
| 3.1 | H1 | m |
| 4.27 | H5 | dd, J=2.0, 8.8Hz |
| 4.9 | H6 | obscured by HOD |
| 5.30 | CH₂O | s |
| 7.4–8.4 | ArH | m, 9H |

UV (H₂O): λmax=270 nm (ε=13,000), 300 nm (ε=12,000)

EXAMPLE 141

(±)-Potassium-(1R, 5R, 6R)-2-(2-cyanoethylthio)-1-methyl-6-p-nitrobenzyloxycarbonylamino-carbapen-2-em-3-carboxylate (30c-transβMe,SR²)

In a manner analogous to that described above, the carbapenem 29c-trans-βMe,SR² (1.0 mg, 0.0021 mmol) gave the title compound (0.3 mg, 30%) as an off-white lyophilized solid.

| ¹H NMR (300 MHz, D₂O): | | |
|---|---|---|
| δ 1.26 | CH₃ | d, J=6.7Hz |
| 2.75–2.85 | CH₂CN | m |
| 2.9–3.1 | SCH₂ | m |
| 3.4 | H1 | m |
| 4.30 | H5 | dd, J=2.0, 9.1Hz |
| 4.8–4.9 | H6 | obscured by HOD |
| 5.27 | CH₂ | s |
| 7.60, 8.26 | ArH | 2 d, J=7.8Hz |

UV (H₂O): λmax=275 nm (ε=12,000)

EXAMPLE 142

(±)-Potassium-(1S, 5R, 6R)-1-methyl-6-N-phthalimidocarbapen-2-em-3-carboxylate (31a-trans-βMe)

In a manner analogous to that described above, allyl ester 25a-trans-βMe (13.0 mg, 0.0369 mmol) gave the title carbapenem (7.5 mg, 58%) as an off-white lyophilized solid.

| ¹H NMR (300 MHz, D₂O): | | |
|---|---|---|
| δ 1.27 | CH₃ | d, J=7.08Hz |
| 3.29 | H1 | m |
| 4.64 | H5 | dd, J=2.56, 9.82Hz |
| 5.55 | H6 | d, J=2.56Hz |
| 6.15 | H2 | d, J=2.08Hz |
| 7.75–7.95 | ArH | m |

What is claimed is:

1. A compound of the structure:

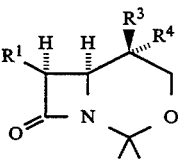

wherein R¹ is H₂N—,

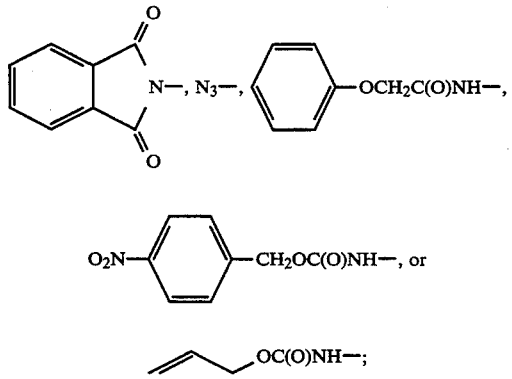

and R³/R⁴ is CH₃/H or H/CH₃.

2. A compound of the structure:

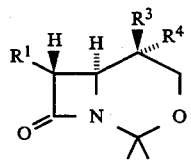

wherein R¹ H₂N—,

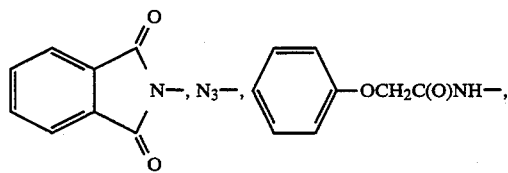

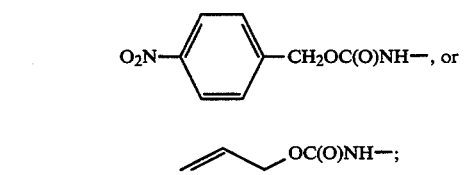

and R³/R⁴ is CH₃/H or H/CH₃.

3. A compound of the formula:

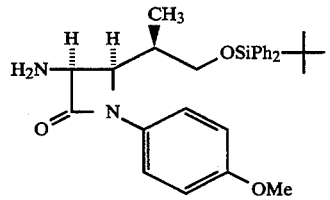

-continued
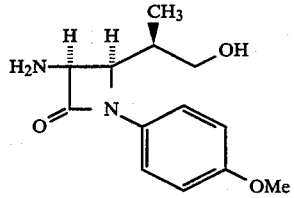
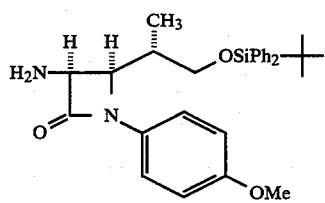
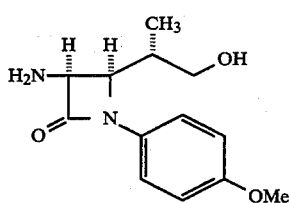
-continued
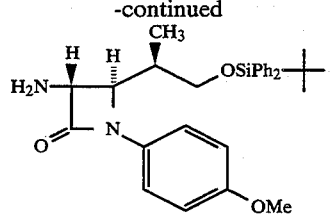
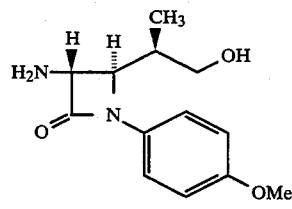
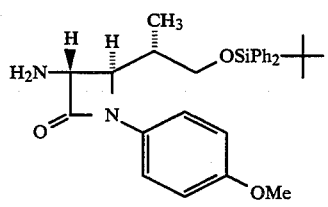
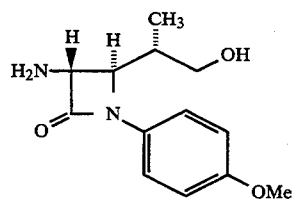
* * * * *